United States Patent
Yamaguchi et al.

(10) Patent No.: US 10,907,179 B2
(45) Date of Patent: *Feb. 2, 2021

(54) PRODUCTION METHOD FOR POLYISOPRENOID, VECTOR, TRANSGENIC PLANT, PRODUCTION METHOD FOR PNEUMATIC TIRE, AND PRODUCTION METHOD FOR RUBBER PRODUCT

(71) Applicants: SUMITOMO RUBBER INDUSTRIES, LTD., Kobe (JP); TOHOKU UNIVERSITY, Sendai (JP)

(72) Inventors: Haruhiko Yamaguchi, Kobe (JP); Yukino Inoue, Kobe (JP); Kazuhisa Fushihara, Kobe (JP); Seiji Takahashi, Sendai (JP); Satoshi Yamashita, Sendai (JP); Toru Nakayama, Sendai (JP)

(73) Assignees: SUMITOMO RUBBER INDUSTRIES, LTD., Kobe (JP); TOHOKU UNIVERSITY, Sendai (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/579,434
(22) PCT Filed: Jun. 28, 2016
(86) PCT No.: PCT/JP2016/069172
§ 371 (c)(1),
(2) Date: Dec. 4, 2017
(87) PCT Pub. No.: WO2017/002818
PCT Pub. Date: Jan. 5, 2017

(65) Prior Publication Data
US 2018/0171364 A1 Jun. 21, 2018

(30) Foreign Application Priority Data

Jun. 30, 2015 (JP) .................................. 2015-131024
Mar. 17, 2016 (JP) .................................. 2016-054541

(51) Int. Cl.
*C12P 5/00* (2006.01)
*C12P 5/02* (2006.01)
(Continued)

(52) U.S. Cl.
CPC ................ *C12P 5/026* (2013.01); *A01H 5/02* (2013.01); *B60C 1/00* (2013.01); *C07K 14/415* (2013.01);
(Continued)

(58) Field of Classification Search
None
See application file for complete search history.

(56) References Cited

U.S. PATENT DOCUMENTS 10,000,774 B2 * 6/2018 Yamaguchi .......... C07K 14/705
10,385,362 B2 * 8/2019 Inoue ..................... B29D 30/08
(Continued)

FOREIGN PATENT DOCUMENTS

CN 104684987 A 6/2015
EP 3 097 775 A1 11/2016
(Continued)

OTHER PUBLICATIONS

Madin et al., "A highly efficient and robust cell-free protein synthesis system prepared from wheat embryos: Plants apparently contain a suicide system directed at ribosomes", Proceedings of the National Academy of Sciences USA, vol. 97, No. 2, pp. 559-564, 2000 (Year: 2000).*

(Continued)

*Primary Examiner* — Richard C Ekstrom
(74) *Attorney, Agent, or Firm* — Birch, Stewart, Kolasch & Birch, LLP

(57) ABSTRACT

The present invention provides a method for producing a polyisoprenoid with which it is possible to enhance the rubber synthesis activity of rubber particles to increase natural rubber production. The present invention relates to a method for producing a polyisoprenoid in vitro, which involves the use of a gene coding for a cis-prenyltransferase (CPT) family protein and a gene coding for a Nogo-B (Continued)

receptor (NgBR) family protein, and further involves the use of rubber particles bound to proteins encoded by these genes; or a method for producing a polyisoprenoid, which includes introducing into a plant a vector in which a promoter having a promoter activity that drives laticifer-specific gene expression is linked to a gene coding for a CPT family protein and a gene coding for a NgBR family protein, to express proteins encoded by the genes specifically in laticifers.

14 Claims, 4 Drawing Sheets

Specification includes a Sequence Listing.

(51) Int. Cl.
| | |
|---|---|
| B60C 1/00 | (2006.01) |
| C12N 15/09 | (2006.01) |
| C07K 14/415 | (2006.01) |
| C12N 15/82 | (2006.01) |
| C12N 9/10 | (2006.01) |
| A01H 5/02 | (2018.01) |
| C08F 136/08 | (2006.01) |
| C08L 47/00 | (2006.01) |

(52) U.S. Cl.
CPC .......... C08F 136/08 (2013.01); C08L 47/00 (2013.01); C12N 9/1085 (2013.01); C12N 15/09 (2013.01); C12N 15/82 (2013.01); C12N 15/8223 (2013.01); C12N 15/8243 (2013.01); C12P 5/007 (2013.01); C12P 5/02 (2013.01); C08F 2810/20 (2013.01); C12Y 504/99 (2013.01)

(56) References Cited

U.S. PATENT DOCUMENTS

| | | | |
|---|---|---|---|
| 2015/0266988 A1 | 9/2015 | Kojima et al. | |
| 2017/0051313 A1* | 2/2017 | Inoue | C12P 5/007 |
| 2018/0171364 A1* | 6/2018 | Yamaguchi | B60C 1/00 |

FOREIGN PATENT DOCUMENTS

| | | |
|---|---|---|
| JP | 2003-18999 A | 1/2003 |
| JP | 2003-310295 A | 11/2003 |
| JP | 2005-500840 A | 1/2005 |
| JP | 2005-225796 A | 8/2005 |
| JP | 2005-308412 A | 11/2005 |
| JP | 2005-312436 A | 11/2005 |
| JP | 2009-221306 A | 10/2009 |
| JP | 2010-119373 A | 6/2010 |
| JP | 2010-132594 A | 6/2010 |
| JP | 2011-52146 A | 3/2011 |
| JP | 2011-188776 A | 9/2011 |
| JP | 5035871 B2 | 9/2012 |
| JP | 2014-11972 A | 1/2014 |
| JP | 5383197 B2 | 1/2014 |
| JP | 2014-227487 A | 12/2014 |
| JP | 2015-136296 A | 7/2015 |
| JP | 2016-93186 A | 5/2016 |
| JP | 2016-149973 A | 8/2016 |
| JP | 2016-154458 A | 9/2016 |
| WO | WO 03/010294 A2 | 2/2003 |

OTHER PUBLICATIONS

Epping et al., "A rubber transferase activator is necessary for natural rubber biosynthesis in dandelion"; Nature Plants; published Apr. 27, 2015, Article No. 15048, pp. 1-9.

Asawatreratanakul et al., "Molecular Cloning, Expression and Characterization of cDNA Encoding cis-Prenyltransferases from Hevea brasiliensis," Eur. J. Biochem., vol. 270, 2003, pp. 4671-4680.

Brasher et al., "A Two-Component Enzyme Complex is Required for Dolichol Biosynthesis in Tomato," The Plant Journal, vol. 82, 2015 (published online Apr. 21, 2015), pp. 903-914.

Harrison et al., "Nogo-B Receptor is Necessary for Cellular Dolichol Biosynthesis and Protein N-glycosylation," The EMBO Journal, vol. 30, No. 12, 2011 (published online May 13, 2011), pp. 2490-2500.

Hillebrand et al., "Down-Regulation of Small Rubber Particle Protein Expression Affects Integrity of Rubber Particles and Rubber Content in Taraxacum brevicorniculatum," PLoS One, vol. 7, No. 7, e41874, Jul. 23, 2012, pp. 1-9.

International Search Report (Form PCT/ISA/210) for International Application No. PCT/JP2016/069172, dated Sep. 6, 2016, with English translation.

Post et al., "Laticifer-Specific cis-Prenyltransferase Silencing Affects the Rubber, Triterpene, and Inulin Content of Taraxacum brevicorniculatum," Plant Physiology, vol. 158, Mar. 2012, pp. 1406-1417 (15 pages total).

Priya et al., "Differential Expression Pattern of Rubber Elongation Factor (REF) mRNA Transcripts from High and Low Yielding Clones of Rubber Tree (Hevea brasiliensis Muell. Arg.)," Plant Cell Rep, vol. 26, 2007 (published online Jul. 14, 2007), pp. 1833-1838.

Priya et al., "Molecular Cloning and Characterization of the Rubber Elongation Factor Gene and its Promoter Sequence from Rubber Tree (Hevea brasiliensis): A Gene Involved in Rubber Biosynthesis," Plant Science, vol. 171, 2006 (published online Jun. 13, 2006), pp. 470-480.

Qu et al., "A Lettuce (Lactuca sativa) Homolog of Human Nogo-B Receptor Interacts with cis-Prenyltransferase and Is Necessary for Natural Rubber Biosynthesis," J. Biol. Chem., vol. 290, No. 4, Jan. 23, 2015 (published online Dec. 4, 2014), pp. 1898-1914 (18 pages total).

Rahman et al., "Draft Genome Sequence of the Rubber Tree Hevea brasiliensis," BMC Genomics, vol. 14, No. 75, 2013, pp. 1-15.

Tata et al., "Laticifer Tissue-Specific Activation of the Hevea SRPP Promoter in Taraxacum brevicorniculatum and its Regulation by Light, Tapping and Cold Stress," Industrial Crops and Products, vol. 40, 2012, pp. 219-224.

Aoki et al., "Identification of Laticifer-specific Genes and their Promoter Regions from a Natural Rubber Producing Plant Hevea brasiliensis," Plant Science, vol. 225, 2014 (Available online May 12, 2014), pp. 1-8.

Berthelot et al., "Hevea brasiliensis REF (Hev b 1) and SRPP (Hev b 3): An Overview on Rubber Particle Proteins," Biochimie, vol. 106, 2014 (Available online Jul. 11, 2014), pp. 1-9.

Branden et al., "Introduction to Protein Structure," Garland Publishing Inc., New York, 1991, p. 247 (3 pages total).

Dai et al., "In-depth proteome analysis of the rubber particle of Hevea brasiliensis (para rubber tree)," Plant Molecular Biology, vol. 82, 2013 (published online Apr. 4, 2013), pp. 155-168.

Goodman, "Polymer biosynthesis: Rubber ramps up," Nature Chemical Biology, vol. 11, No. 7, Jul. 2015, p. 448, XP055373184.

Hofmann et al., "The Who, What, and Where of Plant Polyprenol Biosynthesis Point to Thylakoid Membranes and Photosynthetic Performance," The Plant Cell, vol. 29, Jul. 2019, pp. 1552-1553.

Laibach et al., "Identification of a Taraxacum Brevicorniculatum Rubber Elongation Factor Protein that is Localized on Rubber Particles and Promotes Rubber Biosynthesis," The Plant Journal, vol. 82, 2015 (published online Mar. 24, 2015), pp. 609-620.

Nguyen et al., "cis-Prenyltransferase Interacts with a Nogo-B Receptor Homolog for Dolichol Biosynthesis in Panax ginseng Meyer," Journal of Ginseng Research, vol. 41, 2017 (Available online Jan. 27, 2017), pp. 403-410.

Ohya et al., "Biosynthesis of Natural Rubber and Other Natural Polyisoprenoids," Biopolymers Online, Published online Jan. 15, 2005, 43 pages.

Park et al., "Mutation of Nogo-B receptor, a subunit of cis-prenyltransferase, causes a congenital disorder of glycosylation," Cell Metabolism, vol. 20, Sep. 2, 2014 (published Jul. 24, 2014), pp. 448-457.

(56) References Cited

OTHER PUBLICATIONS

Rahman et al., "TSA: *Hevea brasiliensis* contig33814, mRNA sequence," Database GenBank [online], Accession No. JT945746, Feb. 5, 2013, pp. 1-2.

Rojruthai et al., "In vitro Synthesis of High Molecular Weight Rubber by Hevea Small Rubber Particles," Journal of Bioscience and Bioengineering, vol. 109, No. 2, 2010 (Available online Sep. 18, 2009), pp. 107-114.

Surmacz et al., "cis-Prenyltransferase AtCPT6 produces a family of very short-chain polyisoprenoids in planta," Biochimica et Biophysica Acta, vol. 1841, 2014 (available online Dec. 1, 2013), pp. 240-250.

Takahashi et al., "Characterization of cis-prenyltransferases from the rubber producing plant *Hevea brasiliensis* heterologously expressed in yeast and plant cells," Plant Biotechnology, vol. 29, Oct. 20, 2012 (published online Aug. 30, 2012), pp. 411-417 (8 pages total).

Xiang et al., "Proteome Analysis of the Large and the Small Rubber Particles of *Hevea brasiliensis* Using 2D-DIGE," Plant Physiology and Biochemistry, vol. 60, 2012 (Available online Sep. 5, 2012), pp. 207-213.

International Preliminary Report on Patentability and Written Opinion of the International Searching Authority for International Application No. PCT/JP2017/041732, dated Jun. 25, 2019.

International Search Report for International Application No. PCT/JP2016/065942, dated Jun. 28, 2016.

International Search Report for International Application No. PCT/JP2017/041732, dated Feb. 20, 2018.

Phatthiya et al., "Cloning and Expression of the Gene Encoding Solanesyl Diphosphate Synthase from *Hevea Brasiliensis*", Plant Science, vol. 172, 2007, pp. 824-831.

Takahashi et al., "Molecular Insights of Natural Rubber Biosynthesis—An Approach from Prenyltransferase Gene Analysis", The Society of Rubber Science and Technology, vol. 76, No. 12, 2003, pp. 446-452, with 1 page abstract.

Yamashita et al., "Identification and Reconstitution of the Rubber Biosynthetic Machinery on Rubber Particles from *Hevea Brasiliensis*", eLife, vol. 5, No. 19022, Oct. 28, 2016, pp. 1-28.

Yokoyama, "Development of Membrane Protein-synthesizing System Without Using Cells", NPG Nature Asia-Pacific, vol. 7, No. 4-5, 2010, pp. 28-29, with English translation.

\* cited by examiner (a)

(b)

(c)

PRODUCTION METHOD FOR POLYISOPRENOID, VECTOR, TRANSGENIC PLANT, PRODUCTION METHOD FOR PNEUMATIC TIRE, AND PRODUCTION METHOD FOR RUBBER PRODUCT

TECHNICAL FIELD

The present invention relates to a method for producing a polyisoprenoid, a vector, a transgenic plant, a method for producing a pneumatic tire, and a method for producing a rubber product.

BACKGROUND ART

Nowadays natural rubber (one example of polyisoprenoids) for use in industrial rubber products is obtained by cultivating rubber-producing plants, such as para rubber tree (*Hevea brasiliensis*) belonging to the family Euphorbiaceae or Indian rubber tree (*Ficus elastica*) belonging to the family Moraceae, whose laticifer cells biosynthesize natural rubber, and manually harvesting the natural rubber from the plants.

At present, *Hevea brasiliensis* is virtually the only source for the natural rubber used in industrial rubber products. *Hevea brasiliensis* is a plant that can only be grown in certain regions, including Southeast Asia and South America. Moreover, *Hevea brasiliensis* trees take about seven years from planting to grow mature enough to yield rubber, and they yield natural rubber only for a period of 20 to 30 years. Demand for natural rubber is expected to grow in the future, especially in developing countries, but for the reasons discussed above it is difficult to greatly increase natural rubber production from *Hevea brasiliensis*. There is therefore concern that natural rubber sources will dry up, and needs exist to develop stable natural rubber sources other than mature *Hevea brasiliensis* trees and to improve productivity of natural rubber from *Hevea brasiliensis*.

Natural rubber has a cis-1,4-polyisoprene structure formed mainly of isopentenyl diphosphate (IPP) units, and the nature of this structure suggests that cis-prenyltransferase (CPT) is involved in natural rubber biosynthesis. For example, several CPTs are found in *Hevea brasiliensis*, including *Hevea* rubber transferase 1 (HRT1) and *Hevea* rubber transferase 2 (HRT2) (see, for example, Non Patent Literatures 1 and 2). It is also known that rubber synthesis can be reduced in the dandelion species *Taraxacum brevicorniculatum* by suppressing CPT expression (see, for example, Non Patent Literature 3).

Previous studies of proteins associated with natural rubber biosynthesis have focused on rubber elongation factor (REF) and small rubber particle protein (SRPP) (see, for example, Non Patent Literatures 4 and 5). However, the associations between these proteins and CPT are not completely understood.

It has also been suggested that Nogo-B receptor (NgBR) is involved in dolichol biosynthesis by a human CPT (see, for example, Non Patent Literature 6).

Along with the recent development in gene engineering, it is now possible to transform natural plants by introducing desired exogenous genes into the natural plants. For example, Patent Literature 1 reports that a transgenic plant produced by introducing a gene coding for a prenyltransferase of *Hevea brasiliensis* into a plant can be expected to obtain improved rubber productivity.

However, if the expression of an exogenous gene introduced into a plant is driven in sites other than laticifers, a certain load may be imposed on the metabolism or latex production in the plant, thereby causing adverse effects. In order to solve this problem, promoters that drive gene expression specifically in laticifers are being sought (see, for example, Patent Literature 2 and Non Patent Literatures 7 and 8).

CITATION LIST

Patent Literature

Patent Literature 1: JP 5035871 B
Patent Literature 2: JP 2010-119373 A

Non Patent Literature

Non Patent Literature 1: Rahman et al., BMC Genomics, 2013, vol. 14
Non Patent Literature 2: Asawatreratanakul et al, European Journal of Biochemistry, 2003, vol. 270, pp. 4671-4680
Non Patent Literature 3: Post et al., Plant Physiology, 2012, vol. 158, pp. 1406-1417
Non Patent Literature 4: Hillebrand et al., PLoS ONE, 2012, vol. 7
Non Patent Literature 5: Priya et al., Plant Cell Reports, 2007, vol. 26, pp. 1833-1838
Non Patent Literature 6: K. D. Harrison et al., The EMBO Journal, 2011, vol. 30, pp. 2490-2500
Non Patent Literature 7: P. Priya et al., Plant Science, 2006, vol. 171, pp. 470-480
Non Patent Literature 8: Sandeep Kumar Tata et al., Industrial Crops and Products, 2012, vol. 40, pp. 219-224

SUMMARY OF INVENTION

Technical Problem

As discussed above, needs exist to develop stable natural rubber sources other than mature *Hevea brasiliensis* trees and to improve productivity of natural rubber from *Hevea brasiliensis*. Also, some attempts have been made to develop genetic recombination techniques for enhancing natural rubber production. At present, however, the biosynthesis mechanism of natural rubber and particularly the regulatory mechanism remain largely unclear. Thus, there is still much room for improvement to greatly increase natural rubber production. In this context, one possible approach to solving these problems is to stabilize and increase the activity of CPT in natural rubber biosynthesis in order to increase natural rubber production.

The present invention aims to solve the above problems and provide a method for producing a polyisoprenoid with which it is possible to enhance the rubber synthesis activity of rubber particles to increase natural rubber production.

The present invention also aims to solve the above problems and provide a vector that can be introduced into a plant using genetic recombination techniques to enhance polyisoprenoid production. Further objects are to provide a transgenic plant into which the vector is introduced and to provide a method for enhancing production of cis-isoprenoids or polyisoprenoids in a plant by introducing the vector into the plant.

Solution to Problem

The present invention relates to a method for producing a polyisoprenoid, the method including the step of binding a protein expressed by a gene coding for a cis-prenyltransferase (CPT) family protein and a protein expressed by a gene coding for a Nogo-B receptor (NgBR) family protein to rubber particles in vitro. This invention is hereinafter called the first aspect of the present invention, and is also referred to as the first invention.

The cis-prenyltransferase (CPT) family protein preferably contains:

an aspartic acid residue at position 41 in the amino acid sequence of HRT1 from *Hevea brasiliensis* represented by SEQ ID NO:2 or at a corresponding position;

a glycine residue at position 42 in the amino acid sequence of HRT1 from *Hevea brasiliensis* represented by SEQ ID NO:2 or at a corresponding position;

an arginine residue at position 45 in the amino acid sequence of HRT1 from *Hevea brasiliensis* represented by SEQ ID NO:2 or at a corresponding position; and an asparagine residue at position 89 in the amino acid sequence of HRT1 from *Hevea brasiliensis* represented by SEQ ID NO:2 or at a corresponding position.

The cis-prenyltransferase (CPT) family protein preferably contains, at positions 41 to 49 in the amino acid sequence of HRT1 from *Hevea brasiliensis* represented by SEQ ID NO:2 or at corresponding positions, The following amino acid sequence (A):

$$DGNX_1RX_2AKK \quad (A)$$

wherein $X_1$ and $X_2$ are the same as or different from each other and each represent any amino acid residue, or an amino acid sequence having a sequence identity such that it is identical to at least five out of the seven amino acid residues other than $X_1$ and $X_2$ of the amino acid sequence (A).

The cis-prenyltransferase (CPT) family protein preferably contains, at positions 81 to 97 in the amino acid sequence of HRT1 from *Hevea brasiliensis* represented by SEQ ID NO:2 or at corresponding positions, The following amino acid sequence (B):

$$TX_{11}X_{12}AFSX_{13}X_{14}NX_{15}X_{16}RX_{17}X_{18}X_{19}EV \quad (B)$$

wherein $X_{11}$ to $X_{19}$ are the same as or different from each other and each represent any amino acid residue, or an amino acid sequence having a sequence identity such that it is identical to at least five out of the eight amino acid residues other than $X_{11}$ to $X_{19}$ of the amino acid sequence (B).

Preferably, at least one selected from the group consisting of the gene coding for a cis-prenyltransferase (CPT) family protein and the gene coding for a Nogo-B receptor (NgBR) family protein is derived from a plant.

Preferably, at least one selected from the group consisting of the gene coding for a cis-prenyltransferase (CPT) family protein and the gene coding for a Nogo-B receptor (NgBR) family protein is derived from *Hevea brasiliensis*.

The binding step preferably includes performing protein synthesis in the presence of both rubber particles and a cell-free protein synthesis solution containing an mRNA coding for a cis-prenyltransferase (CPT) family protein and an mRNA coding for a Nogo-B receptor (NgBR) family protein to bind the CPT family protein and the NgBR family protein to the rubber particles.

The cell-free protein synthesis solution preferably contains a germ extract.

The germ extract is preferably derived from wheat.

The rubber particles are preferably present in the cell-free protein synthesis solution at a concentration of 5 to 50 g/L.

The first invention also relates to a method for producing a pneumatic tire, the method including the steps of: kneading a polyisoprenoid produced by the method for producing a polyisoprenoid of the first invention with an additive to obtain a kneaded mixture; building a green tire from the kneaded mixture; and vulcanizing the green tire.

The first invention also relates to a method for producing a rubber product, the method including the steps of: kneading a polyisoprenoid produced by the method for producing a polyisoprenoid of the first invention with an additive to obtain a kneaded mixture; forming a raw rubber product from the kneaded mixture; and vulcanizing the raw rubber product.

The present invention also relates to a vector, including: a promoter having a promoter activity that drives laticifer-specific gene expression; and a gene coding for a Nogo-B receptor (NgBR) family protein functionally linked to the promoter. This invention is hereinafter called the second aspect of the present invention, and is also referred to as the second invention.

The second invention also relates to a vector, including: a promoter having a promoter activity that drives laticifer-specific gene expression; and a gene coding for a cis-prenyltransferase (CPT) family protein functionally linked to the promoter and a gene coding for a Nogo-B receptor (NgBR) family protein functionally linked to the promoter.

The promoter having a promoter activity that drives laticifer-specific gene expression is preferably at least one selected from the group consisting of a promoter of a gene coding for rubber elongation factor (REF), a promoter of a gene coding for small rubber particle protein (SRPP), a promoter of a gene coding for Hevein 2.1 (HEV2.1), and a promoter of a gene coding for MYC1 transcription factor (MYC1).

The second invention also relates to a transgenic plant into which any one of the above-described vectors is introduced.

The second invention also relates to a method for enhancing cis-isoprenoid production in a plant by introducing any of the above-described vectors into the plant.

The second invention also relates to a method for enhancing polyisoprenoid production in a plant by introducing any of the above-described vectors into the plant.

The second invention also relates to a method for producing a pneumatic tire, the method including the steps of: kneading a polyisoprenoid produced by a transgenic plant with an additive to obtain a kneaded mixture, the transgenic plant being produced by introducing any of the above-described vectors into a plant; building a green tire from the kneaded mixture; and vulcanizing the green tire.

The second invention also relates to a method for producing a rubber product, the method including the steps of: kneading a polyisoprenoid produced by a transgenic plant with an additive to obtain a kneaded mixture, the transgenic plant being produced by introducing any of the above-described vectors into a plant; forming a raw rubber product from the kneaded mixture; and vulcanizing the raw rubber product.

Advantageous Effects of Invention

The method for producing a polyisoprenoid of the first invention includes the step of binding a protein expressed by a gene coding for a cis-prenyltransferase (CPT) family protein and a protein expressed by a gene coding for a Nogo-B receptor (NgBR) family protein to rubber particles in vitro. Binding the CPT family protein and NgBR family protein to rubber particles is expected to stabilize and increase the activity of the CPT family protein. It is therefore possible to increase the rubber synthesis activity of the rubber particles, thereby allowing for more efficient rubber production in reaction vessels (e.g. test tubes, industrial plants).

The method for producing a pneumatic tire of the first invention includes the steps of: kneading a polyisoprenoid produced by the method for producing a polyisoprenoid of the first invention with an additive to obtain a kneaded mixture; building a green tire from the kneaded mixture; and vulcanizing the green tire. With this method, pneumatic tires are produced from a polyisoprenoid produced by a method that produces a polyisoprenoid with high productivity. Thus, it is possible to use plant resources effectively to produce environmentally friendly pneumatic tires.

The method for producing a rubber product of the first invention includes the steps of: kneading a polyisoprenoid produced by the method for producing a polyisoprenoid of the first invention with an additive to obtain a kneaded mixture; forming a raw rubber product from the kneaded mixture; and vulcanizing the raw rubber product. With this method, rubber products are produced from a polyisoprenoid produced by a method that produces a polyisoprenoid with high productivity. Thus, it is possible to use plant resources effectively to produce environmentally friendly rubber products.

The vector of the second invention includes: a promoter having a promoter activity that drives laticifer-specific gene expression; and a gene coding for a Nogo-B receptor (NgBR) family protein functionally linked to the promoter. The further vector of the second invention includes: a promoter having a promoter activity that drives laticifer-specific gene expression; and a gene coding for a cis-prenyltransferase (CPT) family protein functionally linked to the promoter and a gene coding for a Nogo-B receptor (NgBR) family protein functionally linked to the promoter. By introducing such a vector into a plant, the gene coding for a protein involved in polyisoprenoid biosynthesis in the vector is expressed specifically in laticifers, thereby enhancing cis-isoprenoid or polyisoprenoid production in the plant.

The method for producing a pneumatic tire of the second invention includes the steps of: kneading a polyisoprenoid produced by a transgenic plant with an additive to obtain a kneaded mixture, wherein the transgenic plant is produced by introducing the vector of the second invention into a plant; building a green tire from the kneaded mixture; and vulcanizing the green tire. With this method, pneumatic tires are produced from a polyisoprenoid produced by a transgenic plant with an enhanced polyisoprenoid production. Thus, it is possible to use plant resources effectively to produce environmentally friendly pneumatic tires.

The method for producing a rubber product of the second invention includes the steps of: kneading a polyisoprenoid produced by a transgenic plant with an additive to obtain a kneaded mixture, wherein the transgenic plant is produced by introducing the vector of the second invention into a plant; forming a raw rubber product from the kneaded mixture; and vulcanizing the raw rubber product. With this method, pneumatic tires are produced from a polyisoprenoid produced by a transgenic plant with an enhanced polyisoprenoid production. Thus, it is possible to use plant resources effectively to produce environmentally friendly rubber products.

DESCRIPTION OF EMBODIMENTS

Herein, the first invention and the second invention are also referred to collectively as the present invention. The first invention will be first explained and later the second invention will be explained.

First Invention

The method for producing a polyisoprenoid of the first invention includes the step of binding a protein expressed by a gene coding for a cis-prenyltransferase (CPT) family protein and a protein expressed by a gene coding for a Nogo-B receptor (NgBR) family protein to rubber particles in vitro.

Figure 1:
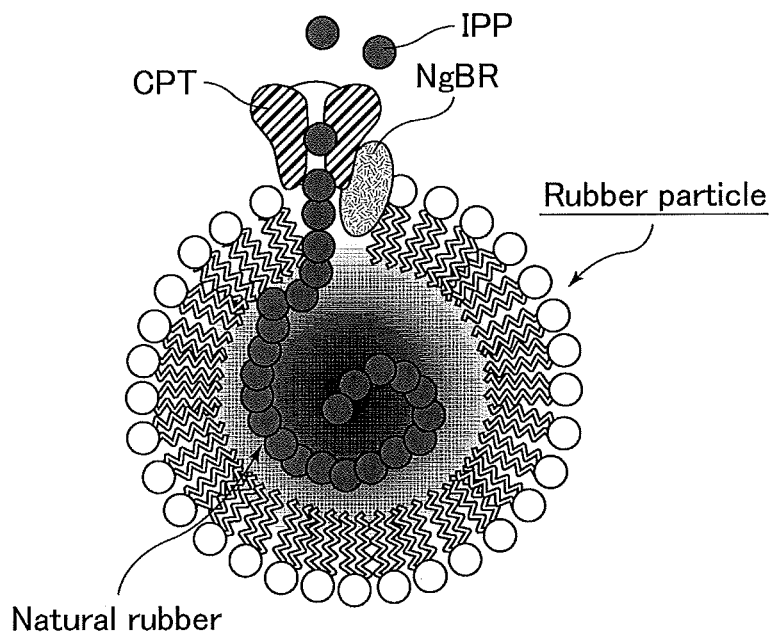
FIG. 1 is a presumptive diagram illustrating rubber synthesis by CPT and NgBR on a rubber particle.

The inventors were the first to discover that the rubber synthesis of rubber particles is activated by binding a CPT family protein and a NgBR family protein to rubber particles in vitro. The inventors have also discovered here for the first time that the combination of a CPT family protein and a NgBR family protein is directly involved in rubber synthesis. It is presumed that the CPT family protein and NgBR family protein are disposed on rubber particles to perform rubber synthesis as shown in FIG. 1. FIG. 1 schematically illustrates an example of rubber synthesis in which CPT and NgBR are shown as the CPT family protein and NgBR family protein, respectively, and the isopentenyl diphosphate (IPP) substrate is polymerized by CPT to synthesize natural rubber within a rubber particle.

Hence, the rubber synthesis activity of rubber particles can be increased by binding a CPT family protein and a NgBR family protein to rubber particles in vitro, for example in reaction vessels (e.g. test tubes, industrial plants) as in the production method of the first invention. Thus, it is possible to produce rubber more efficiently in reaction vessels (e.g. test tubes, industrial plants).

The production method of the first invention may include any other step as long as it involves the above binding step, and each step may be performed once or repeated multiple times.

The amounts of the CPT family protein and NgBR family protein to be bound to the rubber particles are not particularly limited in the first invention.

Herein, binding of a CPT family protein and a NgBR family protein to rubber particles means, for example, the CPT family protein and NgBR family protein are fully or partially incorporated into the rubber particles or inserted into the membrane structure of the rubber particles. It is not limited to these embodiments and also includes embodiments in which, for example, the proteins are localized on the surface or inside of the rubber particles. Moreover, the concept of binding to rubber particles also includes embodiments in which the CPT family protein and NgBR family protein form a complex with another protein bound to the rubber particles as described above so as to be present in the form of the complex on the rubber particles.

The origin of the rubber particles is not particularly limited. For example, the rubber particles may be derived from the latex of a rubber-producing plant such as *Hevea brasiliensis, Taraxacum kok-saghyz, Parthenium argentatum, Sonchus oleraceus,* or *Ficus elastica*.

The particle size of the rubber particles is also not particularly limited. Rubber particles having a predetermined particle size may be sorted out and used, or a mixture of rubber particles having different particle sizes may be used. When rubber particles having a predetermined particle size are sorted out and used, the rubber particles may be either small rubber particles (SRP) having a small particle size or large rubber particles (LRP) having a large particle size.

Commonly used methods may be employed for sorting out the rubber particles having a predetermined particle size, including, for example, methods involving centrifugation, preferably multistage centrifugation. A specific method includes centrifugation at 500-1,500×g, centrifugation at 1,700-2,500×g, centrifugation at 7,000-9,000×g, centrifugation at 15,000-25,000×g, and centrifugation at 40,000-60,000×g, carried out in that order. The duration of each centrifugation treatment is preferably at least 20 minutes, more preferably at least 30 minutes, still more preferably at least 40 minutes, but preferably 120 minutes or less, more preferably 90 minutes or less. The temperature for each centrifugation treatment is preferably 0° C. to 10° C., more preferably 2° C. to 8° C., particularly preferably 4° C.

In the binding step, a protein expressed by a gene coding for a cis-prenyltransferase (CPT) family protein and a protein expressed by a gene coding for a Nogo-B receptor (NgBR) family protein are bound to rubber particles in vitro.

The origins of the gene coding for a cis-prenyltransferase (CPT) family protein and the gene coding for a Nogo-B receptor (NgBR) family protein are not particularly limited. They may be derived from microorganisms, animals, or plants, preferably plants, more preferably at least one selected from the group consisting of plants of the genera *Hevea, Sonchus, Taraxacum,* and *Parthenium*. Among these, they are still more preferably derived from at least one species of plant selected from the group consisting of *Hevea brasiliensis, Sonchus oleraceus, Parthenium argentatum,* and *Taraxacum kok-saghyz*, particularly preferably *Hevea brasiliensis*. Most preferably, they are both derived from *Hevea brasiliensis*. In another suitable embodiment, the gene coding for a cis-prenyltransferase (CPT) family protein and the gene coding for a Nogo-B receptor (NgBR) family protein are derived from the same species.

The plant is not particularly limited, and examples include *Hevea* species such as *Hevea brasiliensis; Sonchus* species such as *Sonchus oleraceus, Sonchus asper,* and *Sonchus brachyotus; Solidago* species such as *Solidago altissima, Solidago virgaurea* subsp. *asiatica, Solidago virgaurea* subsp. *leipcarpa, Solidago virgaurea* subsp. *leipcarpa* f. *paludosa, Solidago virgaurea* subsp. *gigantea,* and *Solidago gigantea* Ait. var. *leiophylla Fernald; Helianthus* species such as *Helianthus annus, Helianthus argophyllus, Helianthus atrorubens, Helianthus debilis, Helianthus decapetalus,* and *Helianthus giganteus; Taraxacum* species such as dandelion (*Taraxacum*), *Taraxacum venustum* H. *Koidz, Taraxacum hondoense Nakai, Taraxacum platycarpum Dahlst, Taraxacum japonicum, Taraxacum officinale Weber, Taraxacum kok-saghyz,* and *Taraxacum brevicorniculatum; Ficus* species such as *Ficus carica, Ficus elastica, Ficus pumila* L., *Ficus erecta* Thumb., *Ficus ampelas* Burm. f., *Ficus benguetensis* Merr., *Ficus irisana* Elm., *Ficus microcarpa* L. f., *Ficus septica* Burm. f., and *Ficus benghalensis; Parthenium* species such as *Parthenium argentatum, Parthenium hysterophorus,* and *Ambrosia artemisiifolia* (*Parthenium hysterophorus*); lettuce (*Lactuca sativa*); *Ficus benghalensis;* and *Arabidopsis thaliana*.

Figure 2:
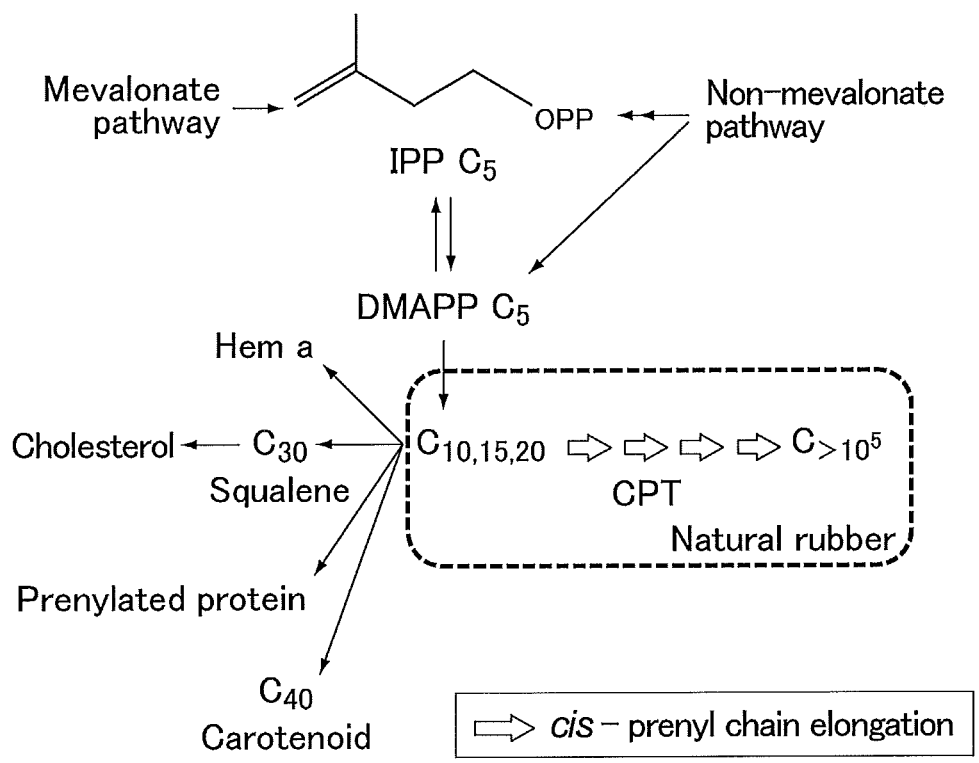
FIG. 2 is a schematic diagram illustrating part of a polyisoprenoid biosynthesis pathway.

Herein, the term "cis-prenyltransferase (CPT) family protein" refers to an enzyme that catalyzes a reaction of cis-chain elongation of an isoprenoid compound. Specifically, in plants, for example, polyisoprenoids are biosynthesized via polyisoprenoid biosynthesis pathways as shown in FIG. 2, in which the CPT family proteins are considered to be enzymes that catalyze the reactions enclosed by the dotted frame in FIG. 2. The CPT family proteins are characterized by having an amino acid sequence contained in the cis-IPPS domain (NCBI accession No. cd00475).

Herein, the term "isoprenoid compound" refers to a compound containing an isoprene unit ($C_5H_8$). Also, the term "cis-isoprenoid" refers to a compound including an isoprenoid compound in which isoprene units are cis-bonded, and examples include cis-farnesyl diphosphate, undecaprenyl diphosphate, and natural rubber.

Figure 5:
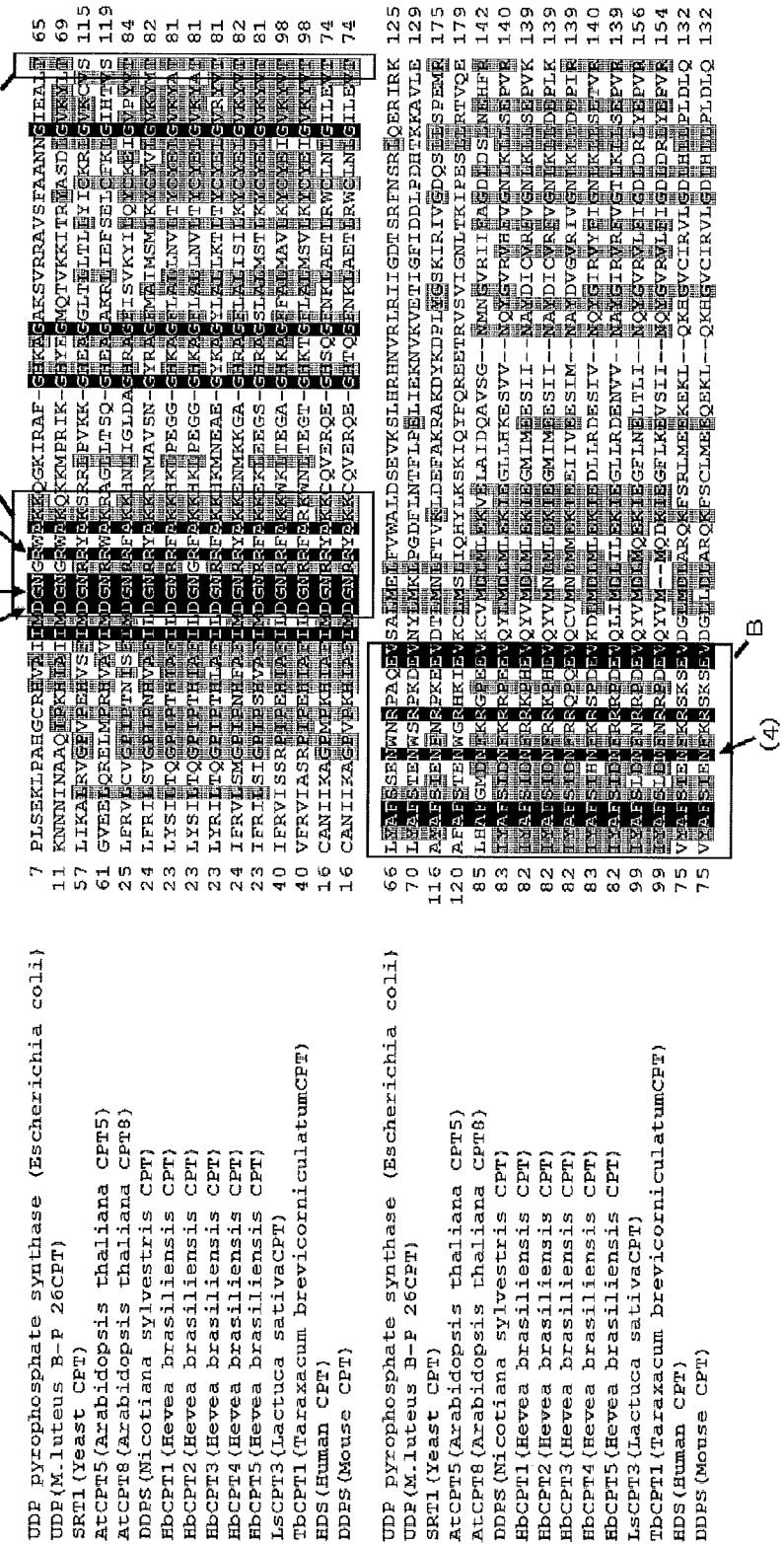
FIG. 5 is an outline diagram illustrating the results of multiple sequence alignment of CPT family proteins derived from various organisms.

FIG. 5 is an outline diagram illustrating the results of multiple sequence alignment of CPT family proteins derived from various organisms. According to literatures such as Shota Endo et. al., Biochimica et Biophysica Acta, No. 1625 (2003), pp. 291-295 and Masahiro Fujihashi et. al., PNAS, Vol. 98, No. 8 (2001), pp. 4337-4342, box A (corresponding to positions 41 to 49 of HRT1 from *Hevea brasiliensis* represented by SEQ ID NO:2) and box B (corresponding to positions 81 to 97 of HRT1 from *Hevea brasiliensis* represented by SEQ ID NO:2) in FIG. 5 are parts of highly conserved regions of CPT family proteins derived from various organisms. The term "conserved region" refers to a site having a similar sequence (structure) which is presumed to have a similar protein function. In particular, it is considered that an aspartic acid residue conserved at a position corresponding to position 41 of HRT1 from *Hevea brasiliensis* represented by SEQ ID NO:2 ((1) in FIG. 5), a glycine residue conserved at a position corresponding to position 42 of HRT1 from *Hevea brasiliensis* represented by SEQ ID NO:2 ((2) in FIG. 5), an arginine residue conserved at a position corresponding to position 45 of HRT1 from *Hevea brasiliensis* represented by SEQ ID NO:2 ((3) in FIG. 5), and an asparagine residue conserved at a position corresponding to position 89 of HRT1 from *Hevea brasiliensis* represented by SEQ ID NO:2 ((4) in FIG. 5) are essential amino acids for the enzymatic reactions of CPT family proteins, so that proteins having these amino acids at the respective positions have the functions of CPT family proteins.

The multiple sequence alignment can be carried out as described later in Examples.

Specifically, the CPT family protein preferably contains: an aspartic acid residue at position 41 in the amino acid sequence of HRT1 from *Hevea brasiliensis* represented by SEQ ID NO:2 or at a corresponding position; a glycine residue at position 42 in the amino acid sequence of HRT1 from *Hevea brasiliensis* represented by SEQ ID NO:2 or at a corresponding position; an arginine residue at position 45 in the amino acid sequence of HRT1 from *Hevea brasiliensis* represented by SEQ ID NO:2 or at a corresponding position; and an asparagine residue at position 89 in the amino acid sequence of HRT1 from *Hevea brasiliensis* represented by SEQ ID NO:2 or at a corresponding position. As described above, the CPT family protein having such a sequence is considered to have the functions of CPT family proteins, including the function as an enzyme that catalyzes a reaction of cis-chain elongation of an isoprenoid compound. Hence, by binding this CPT family protein and a NgBR family protein to rubber particles, it is possible to increase the rubber synthesis activity of the rubber particles to synthesize natural rubber in the rubber particles.

More preferably, the CPT family protein contains, at positions 41 to 49 in the amino acid sequence of HRT1 from *Hevea brasiliensis* represented by SEQ ID NO:2 or at corresponding positions, the following amino acid sequence (A):

$$DGNX_1RX_2AKK \quad (A)$$

wherein $X_1$ and $X_2$ are the same as or different from each other and each represent any amino acid residue, or an amino acid sequence having a sequence identity such that it is identical to at least five out of the seven amino acid residues other than $X_1$ and $X_2$ of the amino acid sequence (A). Still more preferably, in the amino acid sequence (A), $X_1$ represents H, G, or R, and $X_2$ represents W, F, or Y.

The amino acid sequence having a sequence identity such that it is identical to at least five out of the seven amino acid residues other than $X_1$ and $X_2$ of the amino acid sequence (A) is more preferably identical to at least six out of the seven amino acid residues other than $X_1$ and $X_2$.

Also more preferably, the CPT family protein contains, at positions 81 to 97 in the amino acid sequence of HRT1 from *Hevea brasiliensis* represented by SEQ ID NO:2 or at corresponding positions, the following amino acid sequence (B):

$$TX_{11}X_{12}AFSX_{13}X_{14}NX_{15}X_{16}RX_{17}X_{18}X_{19}EV \quad (B)$$

wherein $X_{11}$ to $X_{19}$ are the same as or different from each other and each represent any amino acid residue, or an amino acid sequence having a sequence identity such that it is identical to at least five out of the eight amino acid residues other than $X_{11}$ to $X_{19}$ of the amino acid sequence (B).

Still more preferably, in the amino acid sequence (B), $X_{11}$ represents L, V, A, or I; $X_{12}$ represents Y, F, or H; $X_{13}$ represents S, T, I, M, or L; $X_{14}$ represents E, D, or H; $X_{15}$ represents W or F; $X_{16}$ represents N, S, K, G, or R; $X_{17}$ represents P, S, H, G, R, K, or Q; $X_{18}$ represents A, K, S, or P; and $X_{19}$ represents Q, D, R, I, E, H, or S.

The amino acid sequence having a sequence identity such that it is identical to at least five out of the eight amino acid residues other than $X_{11}$ to $X_{19}$ of the amino acid sequence (B) is more preferably identical to at least six, still more preferably at least seven, out of the eight amino acid residues other than $X_{11}$ to $X_{19}$.

Further, the CPT family protein particularly preferably contains, at positions 41 to 49 in the amino acid sequence of HRT1 from *Hevea brasiliensis* represented by SEQ ID NO:2 or at corresponding positions, an amino acid sequence having a sequence identity such that it is identical to at least six out of the nine amino acid residues (DGNRRFAKK, SEQ ID NO:51) at positions 41 to 49 in the amino acid sequence of HRT1 from *Hevea brasiliensis* represented by SEQ ID NO:2. The sequence identity is more preferably such that the amino acid sequence is identical to at least seven, still more preferably at least eight, out of the nine amino acid residues.

Further, the CPT family protein particularly preferably contains, at positions 81 to 97 in the amino acid sequence of HRT1 from *Hevea brasiliensis* represented by SEQ ID NO:2 or at corresponding positions, an amino acid sequence having a sequence identity such that it is identical to at least 14 out of the 17 amino acid residues (TIYAFSIDN-FRRKPHEV, SEQ ID NO:52) at positions 81 to 97 in the amino acid sequence of HRT1 from *Hevea brasiliensis* represented by SEQ ID NO:2. The sequence identity is more preferably such that the amino acid sequence is identical to at least 15, still more preferably at least 16, out of the 17 amino acid residues.

Specifically, the conserved region corresponding to positions 41 to 49 in the amino acid sequence of HRT1 from *Hevea brasiliensis* represented by SEQ ID NO:2 corresponds to, for example:
   positions 25 to 33 for undecaprenyl pyrophosphate synthase (UPPS) from *Escherichia coli* represented by SEQ ID NO:45;
   positions 29 to 37 for undecaprenyl diphosphate synthase (UPS) from *Micrococcus* represented by SEQ ID NO:46;
   positions 75 to 83 for SRT1 from yeast represented by SEQ ID NO:47;
   positions 79 to 87 for AtCPT5 from *Arabidopsis thaliana* represented by SEQ ID NO:44;
   positions 43 to 51 for AtCPT8 from *Arabidopsis thaliana* represented by SEQ ID NO:22;
   positions 42 to 50 for DDPS from tobacco represented by SEQ ID NO:48;
   positions 41 to 49 for HRT2 from *Hevea brasiliensis* represented by SEQ ID NO:32;
   positions 41 to 49 for CPT3 from *Hevea brasiliensis* represented by SEQ ID NO:36;
   positions 42 to 50 for CPT4 from *Hevea brasiliensis* represented by SEQ ID NO:37;
   positions 41 to 49 for CPT5 from *Hevea brasiliensis* represented by SEQ ID NO:41;
   positions 58 to 66 for LsCPT3 from *Lactuca sativa* represented by SEQ ID NO:14;
   positions 58 to 66 for TbCPT1 from *Taraxacum brevicorniculatum* represented by SEQ ID NO:43;
   positions 34 to 42 for DDPS from mouse represented by SEQ ID NO:49; and
   positions 34 to 42 for HDS from human represented by SEQ ID NO:50.

The conserved region corresponding to positions 81 to 97 in the amino acid sequence of HRT1 from *Hevea brasiliensis* represented by SEQ ID NO:2 corresponds to, for example:
   positions 65 to 81 for undecaprenyl pyrophosphate synthase (UPPS) from *Escherichia coli* represented by SEQ ID NO:45;
   positions 69 to 85 for undecaprenyl diphosphate synthase (UPS) from *Micrococcus* represented by SEQ ID NO:46;
   positions 115 to 131 for SRT1 from yeast represented by SEQ ID NO:47;
   positions 119 to 135 for AtCPT5 from *Arabidopsis thaliana* represented by SEQ ID NO:44;
   positions 84 to 100 for AtCPT8 from *Arabidopsis thaliana* represented by SEQ ID NO:22;
   positions 82 to 98 for DDPS from tobacco represented by SEQ ID NO:48;
   positions 81 to 97 for HRT2 from *Hevea brasiliensis* represented by SEQ ID NO:32;
   positions 81 to 97 for CPT3 from *Hevea brasiliensis* represented by SEQ ID NO:36;
   positions 82 to 98 for CPT4 from *Hevea brasiliensis* represented by SEQ ID NO:37;
   positions 81 to 97 for CPT5 from *Hevea brasiliensis* represented by SEQ ID NO:41;
   positions 98 to 114 for LsCPT3 from *Lactuca sativa* represented by SEQ ID NO:14;

positions 98 to 114 for TbCPT1 from *Taraxacum brevicorniculatum* represented by SEQ ID NO:43;

positions 74 to 90 for DDPS from mouse represented by SEQ ID NO:49; and positions 74 to 90 for HDS from human represented by SEQ ID NO:50.

The aspartic acid residue corresponding to position 41 in the amino acid sequence of HRT1 from *Hevea brasiliensis* represented by SEQ ID NO:2 corresponds to, for example:

an aspartic acid residue at position 25 for undecaprenyl pyrophosphate synthase (UPPS) from *Escherichia coli* represented by SEQ ID NO:45;

an aspartic acid residue at position 29 for undecaprenyl diphosphate synthase (UPS) from *Micrococcus* represented by SEQ ID NO:46;

an aspartic acid residue at position 75 for SRT1 from yeast represented by SEQ ID NO:47;

an aspartic acid residue at position 79 for AtCPT5 from *Arabidopsis thaliana* represented by SEQ ID NO:44;

an aspartic acid residue at position 43 for AtCPT8 from *Arabidopsis thaliana* represented by SEQ ID NO:22;

an aspartic acid residue at position 42 for DDPS from tobacco represented by SEQ ID NO:48;

an aspartic acid residue at position 41 for HRT2 from *Hevea brasiliensis* represented by SEQ ID NO:32;

an aspartic acid residue at position 41 for CPT3 from *Hevea brasiliensis* represented by SEQ ID NO:36;

an aspartic acid residue at position 42 for CPT4 from *Hevea brasiliensis* represented by SEQ ID NO:37;

an aspartic acid residue at position 41 for OPTS from *Hevea brasiliensis* represented by SEQ ID NO:41;

an aspartic acid residue at position 58 for LsCPT3 from *Lactuca sativa* represented by SEQ ID NO:14;

an aspartic acid residue at position 58 for TbCPT1 from *Taraxacum brevicorniculatum* represented by SEQ ID NO:43;

an aspartic acid residue at position 34 for DDPS from mouse represented by SEQ ID NO:49; and an aspartic acid residue at position 34 for HDS from human represented by SEQ ID NO:50.

The glycine residue corresponding to position 42 in the amino acid sequence of HRT1 from *Hevea brasiliensis* represented by SEQ ID NO:2 corresponds to, for example:

a glycine residue at position 26 for undecaprenyl pyrophosphate synthase (UPPS) from *Escherichia coli* represented by SEQ ID NO:45;

a glycine residue at position 30 for undecaprenyl diphosphate synthase (UPS) from *Micrococcus* represented by SEQ ID NO:46;

a glycine residue at position 76 for SRT1 from yeast represented by SEQ ID NO:47;

a glycine residue at position 80 for AtCPT5 from *Arabidopsis thaliana* represented by SEQ ID NO:44;

a glycine residue at position 44 for AtCPT8 from *Arabidopsis thaliana* represented by SEQ ID NO:22;

a glycine residue at position 43 for DDPS from tobacco represented by SEQ ID NO:48;

a glycine residue at position 42 for HRT2 from *Hevea brasiliensis* represented by SEQ ID NO:32;

a glycine residue at position 42 for CPT3 from *Hevea brasiliensis* represented by SEQ ID NO:36;

a glycine residue at position 43 for CPT4 from *Hevea brasiliensis* represented by SEQ ID NO:37;

a glycine residue at position 42 for CPT5 from *Hevea brasiliensis* represented by SEQ ID NO:41;

a glycine residue at position 59 for LsCPT3 from *Lactuca sativa* represented by SEQ ID NO:14;

a glycine residue at position 59 for TbCPT1 from *Taraxacum brevicorniculatum* represented by SEQ ID NO:43;

a glycine residue at position 35 for DDPS from mouse represented by SEQ ID NO:49; and a glycine residue at position 35 for HDS from human represented by SEQ ID NO:50.

The arginine residue corresponding to position 45 in the amino acid sequence of HRT1 from *Hevea brasiliensis* represented by SEQ ID NO:2 corresponds to, for example:

an arginine residue at position 29 for undecaprenyl pyrophosphate synthase (UPPS) from *Escherichia coli* represented by SEQ ID NO:45;

an arginine residue at position 33 for undecaprenyl diphosphate synthase (UPS) from *Micrococcus* represented by SEQ ID NO:46;

an arginine residue at position 79 for SRT1 from yeast represented by SEQ ID NO:47;

an arginine residue at position 83 for AtCPT5 from *Arabidopsis thaliana* represented by SEQ ID NO:44;

an arginine residue at position 47 for AtCPT8 from *Arabidopsis thaliana* represented by SEQ ID NO:22;

an arginine residue at position 46 for DDPS from tobacco represented by SEQ ID NO:48;

an arginine residue at position 45 for HRT2 from *Hevea brasiliensis* represented by SEQ ID NO:32;

an arginine residue at position 45 for CPT3 from *Hevea brasiliensis* represented by SEQ ID NO:36;

an arginine residue at position 46 for CPT4 from *Hevea brasiliensis* represented by SEQ ID NO:37;

an arginine residue at position 45 for OPTS from *Hevea brasiliensis* represented by SEQ ID NO:41;

an arginine residue at position 62 for LsCPT3 from *Lactuca sativa* represented by SEQ ID NO:14;

an arginine residue at position 62 for TbCPT1 from *Taraxacum brevicorniculatum* represented by SEQ ID NO:43;

an arginine residue at position 38 for DDPS from mouse represented by SEQ ID NO:49; and an arginine residue at position 38 for HDS from human represented by SEQ ID NO:50.

The asparagine residue corresponding to position 89 in the amino acid sequence of HRT1 from *Hevea brasiliensis* represented by SEQ ID NO:2 corresponds to, for example:

an asparagine residue at position 73 for undecaprenyl pyrophosphate synthase (UPPS) from *Escherichia coli* represented by SEQ ID NO:45;

an asparagine residue at position 77 for undecaprenyl diphosphate synthase (UPS) from *Micrococcus* represented by SEQ ID NO:46;

an asparagine residue at position 123 for SRT1 from yeast represented by SEQ ID NO:47;

an asparagine residue at position 127 for AtCPT5 from *Arabidopsis thaliana* represented by SEQ ID NO:44;

an asparagine residue at position 92 for AtCPT8 from *Arabidopsis thaliana* represented by SEQ ID NO:22;

an asparagine residue at position 90 for DDPS from tobacco represented by SEQ ID NO:48;

an asparagine residue at position 89 for HRT2 from *Hevea brasiliensis* represented by SEQ ID NO:32;

an asparagine residue at position 89 for CPT3 from *Hevea brasiliensis* represented by SEQ ID NO:36;

an asparagine residue at position 90 for CPT4 from *Hevea brasiliensis* represented by SEQ ID NO:37;

an asparagine residue at position 89 for CPT5 from *Hevea brasiliensis* represented by SEQ ID NO:41;

an asparagine residue at position 106 for LsCPT3 from *Lactuca sativa* represented by SEQ ID NO:14;

an asparagine residue at position 106 for TbCPT1 from *Taraxacum brevicorniculatum* represented by SEQ ID NO:43;

an asparagine residue at position 82 for DDPS from mouse represented by SEQ ID NO:49; and an asparagine residue at position 82 for HDS from human represented by SEQ ID NO:50.

Examples of the CPT family protein include CPT from *Hevea brasiliensis* (HRT1, HRT2, CPT3 to CPT5), AtCPT1 to AtCPT9 from *Arabidopsis thaliana*, CPT1 to CPT3 from *Lactuca sativa*, CPT1 to CPT3 from *Taraxacum brevicorniculatum*, undecaprenyl pyrophosphate synthase (UPPS) from *Escherichia coli*, undecaprenyl diphosphate synthase (UPS) from *Micrococcus*, SRT1 from yeast, DDPS from tobacco, DDPS from mouse, and HDS from human.

Not only rubber-producing plants which produce rubber but other organisms such as plants, animals, and microorganisms as well have genes coding for the CPT family proteins. Of course the CPT family proteins from these organisms are not involved in rubber synthesis in nature. Despite this fact, in the present invention, by binding any CPT family protein, regardless of the origin, type, and other factors of the protein, to rubber particles, it is possible to increase the rubber synthesis activity of the rubber particles to synthesize natural rubber in the rubber particles. Moreover, the rubber synthesis activity of rubber particles can be expected to be further increased by binding the CPT family protein and a NgBR family protein to the rubber particles. This is probably due to the interaction between the CPT family protein and NgBR family protein.

Thus, according to the present invention, surprisingly the use of any CPT family protein can increase the rubber synthesis activity of rubber particles to synthesize natural rubber in the rubber particles, for example, regardless of whether the gene coding for the CPT family protein is derived from a rubber-producing plant or any other organism, or whether it is involved in rubber synthesis in nature. The present inventors consider that the host into which the gene is introduced, or in other words the environment in which the CPT family protein is expressed is more important for the rubber synthesis activity than the origin or type of the CPT family protein.

In this regard, the present inventors assume the following mechanism.

That is, they suppose that the chain length of a product to be synthesized by a CPT family protein depends on the hydrophobicity and space of the site where the synthesized product accumulates.

Specifically, in prokaryotes such as *Escherichia coli*, the CPT family proteins show an activity that produces no detectable reaction product, or even if they show activity to synthesize products, the products have chains extended only to a length receivable within the hydrophobic cleft structures of the CPT family proteins.

In eukaryotes such as yeasts, the products synthesized by the CPT family proteins transfer from the hydrophobic cleft structures of the CPT family proteins into the lipid bilayers of cells, for example into the endoplasmic reticulum lumen, and accumulate in the lipid bilayers whose environment is hydrophobic but whose space is not very large, and therefore the products have limited chain lengths.

Also in non rubber-producing plants such as *Arabidopsis thaliana*, similarly as in yeasts, the products synthesized by the CPT family proteins accumulate in the lipid bilayers of cells whose space is not very large, and thus the synthesized products also have limited chain lengths.

In contrast, when a CPT family protein is bound to rubber particles, a product synthesized by the CPT family protein accumulates in the rubber particles whose environment is hydrophobic and whose space is much larger than that in the lipid bilayers of cells, as illustrated in FIG. 1. Thus, the chain length of the product is sufficiently extended in such a hydrophobic environment with few spatial restrictions, so that a very long chain polyisoprenoid (natural rubber) can be synthesized.

According to this principle, the CPT family protein used in the present invention desirably has a transmembrane domain on the N-terminal side to have a higher affinity for rubber particles. In the case of a wild type having no transmembrane domain, a transmembrane domain may be artificially fused to the N-terminal side of the CPT family protein. The transmembrane domain to be fused may have any amino acid sequence, desirably an amino acid sequence of the transmembrane domain of a protein inherently bound to rubber particles in nature.

Nogo-B receptor (NgBR) family proteins are proteins having the function of binding to a membrane via one or more transmembrane domains on the N-terminal side of the proteins, and interacting with CPT family proteins or other proteins on the C-terminal side thereof, and assist the function of the CPT family proteins by holding the CPT family proteins on the membrane. The NgBR family proteins are characterized by having a transmembrane domain on the N-terminal side and an amino acid sequence contained in the cis-IPPS superfamily domain (NCBI accession No. COG0020) on the C-terminal side.

Examples of the NgBR family protein used include NgBR from *Hevea brasiliensis* (HRTBP), AtLEW1 from *Arabidopsis thaliana*, LsCPTL1 to LsCPTL2 from *Lactuca sativa*, and TbRTA from *Taraxacum*.

Specific examples of the CPT family protein used include the following protein [1]:

[1] a protein having the amino acid sequence represented by SEQ ID NO:2.

It is known that proteins having one or more amino acid substitutions, deletions, insertions, or additions relative to the original amino acid sequence can have the inherent function. Thus, another specific example of the CPT family protein is the following protein [2]:

[2] a protein having an amino acid sequence containing one or more amino acid substitutions, deletions, insertions, and/or additions relative to the amino acid sequence represented by SEQ ID NO:2, and having an enzyme activity that catalyzes a reaction of cis-chain elongation of an isoprenoid compound.

In order to maintain the function of the CPT family protein, it preferably has an amino acid sequence containing one or more, more preferably 1 to 58, still more preferably 1 to 44, further more preferably 1 to 29, particularly preferably 1 to 15, most preferably 1 to 6, yet most preferably 1 to 3 amino acid substitutions, deletions, insertions, and/or additions relative to the amino acid sequence represented by SEQ ID NO:2.

Among other amino acid substitutions, conservative substitutions are preferred. Specific examples include substitutions within each of the following groups in the parentheses: (glycine, alanine), (valine, isoleucine, leucine), (aspartic acid, glutamic acid), (asparagine, glutamine), (serine, threonine), (lysine, arginine), and (phenylalanine, tyrosine).

It is also known that proteins with amino acid sequences having high sequence identity to the original amino acid sequence can also have similar functions. Thus, another specific example of the CPT family protein is the following protein [3]:

[3] a protein having an amino acid sequence with at least 80% sequence identity to the amino acid sequence represented by SEQ ID NO: 2, and having an enzyme activity that catalyzes a reaction of cis-chain elongation of an isoprenoid compound.

In order to maintain the function of the CPT family protein, the sequence identity to the amino acid sequence represented by SEQ ID NO:2 is preferably at least 85%, more preferably at least 90%, still more preferably at least 95%, particularly preferably at least 98%, most preferably at least 99%.

Specific examples of the CPT family protein also include the following protein [11]:

[11] a protein having the amino acid sequence represented by SEQ ID NO:32, 36, 41, 22, 14, 43, 47, or 50.

It is also known that proteins with amino acid sequences having high sequence identity to the original amino acid sequence can also have similar functions. Thus, another specific example of the CPT family protein is the following protein [12]:

[12] a protein having an amino acid sequence with at least 80% sequence identity to the amino acid sequence represented by SEQ ID NO:32, 36, 41, 22, 14, 43, 47, or 50, and having an enzyme activity that catalyzes a reaction of cis-chain elongation of an isoprenoid compound.

In order to maintain the function of the CPT family protein, the sequence identity to the amino acid sequence represented by SEQ ID NO:32, 36, 41, 22, 14, 43, 47, or 50 is preferably at least 85%, more preferably at least 90%, still more preferably at least 95%, particularly preferably at least 98%, most preferably at least 99%.

Herein, the sequence identity between amino acid sequences or nucleotide sequences may be determined using the algorithm BLAST [Pro. Natl. Acad. Sci. USA, 90, 5873 (1993)] developed by Karlin and Altschul or FASTA [Methods Enzymol., 183, 63 (1990)].

Whether it is a protein having the above enzyme activity may be determined by conventional techniques, such as by expressing a target protein in a transformant produced by introducing a gene coding for the target protein into *Escherichia coli* or other host organisms, and determining the presence or absence of the function of the target protein by the corresponding activity measuring method.

Specific examples of the NgBR family protein include the following protein [4]:

[4] a protein having the amino acid sequence represented by SEQ ID NO:4.

It is known that proteins having one or more amino acid substitutions, deletions, insertions, or additions relative to the original amino acid sequence can have the inherent function. Thus, another specific example of the NgBR family protein is the following protein [5]:

[5] a protein having an amino acid sequence containing one or more amino acid substitutions, deletions, insertions, and/or additions relative to the amino acid sequence represented by SEQ ID NO:4, and having the function of binding to a membrane via one or more transmembrane domains on the N-terminal side of the protein, and interacting with another protein on the C-terminal side thereof.

In order to maintain the function of the NgBR family protein, it preferably has an amino acid sequence containing one or more, more preferably 1 to 52, still more preferably 1 to 39, further more preferably 1 to 26, particularly preferably 1 to 13, most preferably 1 to 6, yet most preferably 1 to 3 amino acid substitutions, deletions, insertions, and/or additions relative to the amino acid sequence represented by SEQ ID NO:

Among other amino acid substitutions, conservative substitutions are preferred. Specific examples include substitutions within each of the following groups in the parentheses: (glycine, alanine), (valine, isoleucine, leucine), (aspartic acid, glutamic acid), (asparagine, glutamine), (serine, threonine), (lysine, arginine), and (phenylalanine, tyrosine).

As described above, it is also known that proteins with amino acid sequences having high sequence identity to the original amino acid sequence can also have similar functions. Thus, another specific example of the NgBR family protein is the following protein [6]:

[6] a protein having an amino acid sequence with at least 80% sequence identity to the amino acid sequence represented by SEQ ID NO:4, and having the function of binding to a membrane via one or more transmembrane domains on the N-terminal side of the protein, and interacting with another protein on the C-terminal side thereof.

In order to maintain the function of the NgBR family protein, the sequence identity to the amino acid sequence represented by SEQ ID NO:4 is preferably at least 85%, more preferably at least 90%, still more preferably at least 95%, particularly preferably at least 98%, most preferably at least 99%.

Specific examples of the NgBR family protein also include the following protein [14]:

[14] a protein having the amino acid sequence represented by SEQ ID NO:24 or 16.

As described above, it is also known that proteins with amino acid sequences having high sequence identity to the original amino acid sequence can also have similar functions. Thus, another specific example of the NgBR family protein is the following protein [15]:

[15] a protein having an amino acid sequence with at least 80% sequence identity to the amino acid sequence represented by SEQ ID NO: 24 or 16, and having the function of binding to a membrane via one or more transmembrane domains on the N-terminal side of the protein, and interacting with another protein on the C-terminal side thereof.

In order to maintain the function of the NgBR family protein, the sequence identity to the amino acid sequence represented by SEQ ID NO:24 or 16 is preferably at least 85%, more preferably at least 90%, still more preferably at least 95%, particularly preferably at least 98%, most preferably at least 99%.

Whether it is a NgBR family protein described above may be determined by conventional techniques, such as by identifying the amino acid sequence and then determining whether it has an amino acid sequence contained in the cis-IPPS superfamily domain (NCBI accession No. COG0020).

The gene coding for the CPT family protein is not particularly limited as long as it codes for the CPT family protein to express and produce the CPT family protein. Specific examples of the gene include the following DNAs [1] and [2]:

[1] a DNA having the nucleotide sequence represented by SEQ ID NO:1; and

[2] a DNA which hybridizes under stringent conditions to a DNA having a nucleotide sequence complementary to the nucleotide sequence represented by SEQ ID NO:1, and which codes for a protein having an enzyme activity that catalyzes a reaction of cis-chain elongation of an isoprenoid compound.

As used herein, the term "hybridize" means a process in which a DNA hybridizes to a DNA having a specific nucleotide sequence or a part of the DNA. Accordingly, the DNA having a specific nucleotide sequence or part of the DNA may have a nucleotide sequence long enough to be usable as a probe in Northern or Southern blot analysis or as an oligonucleotide primer in polymerase chain reaction (PCR) analysis. The DNA used as a probe may have a length of at least 100 bases, preferably at least 200 bases, more preferably at least 500 bases although it may be a DNA of at least 10 bases, preferably of at least 15 bases in length.

Techniques to perform DNA hybridization experiments are well known. The hybridization conditions under which experiments are carried out may be determined according to, for example, Molecular Cloning, 2nd ed. and 3rd ed. (2001), Methods for General and Molecular Bacteriology, ASM Press (1994), Immunology methods manual, Academic press (Molecular), and many other standard textbooks.

The stringent conditions may include, for example, an overnight incubation at 42° C. of a DNA-immobilized filter and a DNA probe in a solution containing 50% formamide, 5×SSC (750 mM sodium chloride, 75 mM sodium citrate), 50 mM sodium phosphate (pH 7.6), 5×Denhardt's solution, 10% dextran sulfate, and 20 μg/L denatured salmon sperm DNA, followed by washing the filter for example in a 0.2×SSC solution at approximately 65° C. Less stringent conditions may also be used. Changes in the stringency may be accomplished through the manipulation of formamide concentration (lower percentages of formamide result in lower stringency), salt concentrations or temperature. For example, low stringent conditions include an overnight incubation at 37° C. in a solution containing 6×SSCE (20×SSCE: 3 mol/L sodium chloride, 0.2 mol/L sodium dihydrogen phosphate, 0.02 mol/L EDTA, pH 7.4), 0.5% SDS, 30% formamide, and 100 μg/L denatured salmon sperm DNA, followed by washing in a 1×SSC solution containing 0.1% SDS at 50° C. In addition, to achieve even lower stringency, washes performed following hybridization may be done at higher salt concentrations (e.g. 5×SSC) in the above-mentioned low stringent conditions.

Variations in the above various conditions may be accomplished through the inclusion or substitution of blocking reagents used to suppress background in hybridization experiments. The inclusion of blocking reagents may require modification of the hybridization conditions for compatibility.

The DNA capable of hybridization under stringent conditions as described above may have a nucleotide sequence with at least 80%, preferably at least 90%, more preferably at least 95%, still more preferably at least 98%, particularly preferably at least 99% sequence identity to the nucleotide sequence represented by SEQ ID NO:1 as calculated using a program such as BLAST or FASTA with the parameters mentioned above.

Specific examples of the gene coding for the CPT family protein also include the following DNAs [11] and [12]:
[11] a DNA having the nucleotide sequence represented by SEQ ID NO:31, 35, 40, 21, 13, 42, 63, or 64; and
[12] a DNA which hybridizes under stringent conditions to a DNA having a nucleotide sequence complementary to the nucleotide sequence represented by SEQ ID NO:31, 35, 40, 21, 13, 42, 63, or 64, and which codes for a protein having an enzyme activity that catalyzes a reaction of cis-chain elongation of an isoprenoid compound.

As used here, the term "hybridize" is as described above. Also, the stringent conditions are as described above.

The DNA capable of hybridization under stringent conditions as described above may have a nucleotide sequence with at least 80%, preferably at least 90%, more preferably at least 95%, still more preferably at least 98%, particularly preferably at least 99% sequence identity to the nucleotide sequence represented by SEQ ID NO:31, 35, 40, 21, 13, 42, 63, or 64 as calculated using a program such as BLAST or FASTA with the parameters mentioned above.

Whether the DNA which hybridizes to the aforementioned DNA under stringent conditions codes for a protein having a predetermined enzyme activity may be determined by conventional techniques, such as by expressing a target protein in a transformant produced by introducing a gene coding for the target protein into *Escherichia coli* or other host organisms, and determining the presence or absence of the function of the target protein by the corresponding activity measuring method.

Specific examples of the gene coding for the NgBR family protein include the following DNAs [3] and [4]:
[3] a DNA having the nucleotide sequence represented by SEQ ID NO:3; and
[4] a DNA which hybridizes under stringent conditions to a DNA having a nucleotide sequence complementary to the nucleotide sequence represented by SEQ ID NO:3, and which codes for a protein having the function of binding to a membrane via one or more transmembrane domains on the N-terminal side of the protein, and interacting with another protein on the C-terminal side thereof.

As used here, the term "hybridize" is as described above. Also, the stringent conditions are as described above.

The DNA capable of hybridization under stringent conditions as described above may have a nucleotide sequence with at least 80%, preferably at least 90%, more preferably at least 95%, still more preferably at least 98%, particularly preferably at least 99% sequence identity to the nucleotide sequence represented by SEQ ID NO:3 as calculated using a program such as BLAST or FASTA with the parameters mentioned above.

Specific examples of the gene coding for the NgBR family protein also include the following DNAs [13] and [14]:
[13] a DNA having the nucleotide sequence represented by SEQ ID NO:23 or 15; and
[14] a DNA which hybridizes under stringent conditions to a DNA having a nucleotide sequence complementary to the nucleotide sequence represented by SEQ ID NO:23 or 15, and which codes for a protein having the function of binding to a membrane via one or more transmembrane domains on the N-terminal side of the protein, and interacting with another protein on the C-terminal side thereof.

As used here, the term "hybridize" is as described above. Also, the stringent conditions are as described above.

The DNA capable of hybridization under stringent conditions as described above may have a nucleotide sequence with at least 80%, preferably at least 90%, more preferably at least 95%, still more preferably at least 98%, particularly preferably at least 99% sequence identity to the nucleotide sequence represented by SEQ ID NO:23 or 15 as calculated using a program such as BLAST or FASTA with the parameters mentioned above.

Whether the DNA which hybridizes to the aforementioned DNA under stringent conditions is a DNA coding for a NgBR family protein may be determined by conventional techniques, such as by translating the DNA into an amino acid sequence and then determining whether the amino acid sequence has an amino acid sequence contained in the cis-IPPS superfamily domain (NCBI accession No. COG0020).

Conventional techniques may be employed to identify the amino acid sequence or the nucleotide sequence of the proteins. For example, total RNA is extracted from a growing plant, the mRNA is optionally purified, and a cDNA is synthesized by a reverse transcription reaction. Subsequently, degenerate primers are designed based on the amino acid sequence of a known protein corresponding to the target protein, a DNA fragment is partially amplified by RT-PCR, and the sequence is partially identified. Then, the RACE method or the like is performed to identify the full-length nucleotide sequence or amino acid sequence. The RACE method (rapid amplification of cDNA ends method) refers to a method in which, when the nucleotide sequence of a cDNA is partially known, PCR is performed based on the nucleotide sequence information of such a known region to clone an unknown region extending to the cDNA terminal, and this method is capable of cloning full-length cDNA by PCR without preparing a cDNA library.

The degenerate primers may each preferably be prepared from a plant-derived sequence having a highly similar sequence part to the target protein.

If the nucleotide sequence coding for the protein is known, the full-length nucleotide sequence or amino acid sequence can be identified by designing a primer containing a start codon and a primer containing a stop codon using the known nucleotide sequence, followed by performing RT-PCR using a synthesized cDNA as a template.

In the binding step, other proteins may further be bound to the rubber particles as long as the protein expressed by a gene coding for a cis-prenyltransferase (CPT) family protein and the protein expressed by a gene coding for a Nogo-B receptor (NgBR) family protein are bound to the rubber particles in vitro.

The origin of the other proteins is not particularly limited, but preferably the other proteins are derived from any of the plants mentioned above, more preferably at least one selected from the group consisting of plants of the genera *Hevea*, *Sonchus*, *Taraxacum*, and *Parthenium*. Among these, they are still more preferably derived from at least one species of plant selected from the group consisting of *Hevea brasiliensis*, *Sonchus oleraceus*, *Parthenium argentatum*, and *Taraxacum kok-saghyz*, particularly preferably *Hevea brasiliensis*.

The other proteins may each be any protein without any limitations, but for purposes of increasing the rubber synthesis activity of the rubber particles, they are preferably proteins that inherently exist on rubber particles in rubber-producing plants. The protein that exists on rubber particles may be a protein bound to a large part of the membrane surface of rubber particles, or a protein inserted into and bound to the membrane of rubber particles, or a protein that forms a complex with another protein bound to the membrane so as to be present on the membrane surface.

Examples of the protein that inherently exists on rubber particles in rubber-producing plants include rubber elongation factor (REF), small rubber particle protein (SRPP), β-1,3-glucanase, and Hevein.

The binding step may be carried out by any method that binds the CPT family protein and NgBR family protein to rubber particles in vitro, such as, for example, by performing protein synthesis in the presence of both rubber particles and a cell-free protein synthesis solution containing an mRNA coding for the CPT family protein and an mRNA coding for the NgBR family protein to bind the CPT family protein and the NgBR family protein to the rubber particles.

The binding step preferably includes performing protein synthesis in the presence of both rubber particles and a cell-free protein synthesis solution containing an mRNA coding for a CPT family protein and an mRNA coding for a NgBR family protein to bind the CPT family protein and the NgBR family protein to the rubber particles, among other methods.

In other words, rubber particles bound to a CPT family protein and a NgBR family protein are preferably obtained by performing protein synthesis in the presence of both rubber particles and a cell-free protein synthesis solution containing mRNAs coding for the CPT family protein and the NgBR family protein, or more specifically, using a mixture of rubber particles with a cell-free protein synthesis solution containing mRNAs coding for the CPT family protein and the NgBR family protein.

Since liposomes are artificially produced as lipid bilayer membranes formed of phospholipids, glyceroglycolipids, cholesterol, or other components, no protein is bound to the surface of the produced liposomes. In contrast, although rubber particles collected from the latex of rubber-producing plants are also coated with a lipid membrane, the membrane of the rubber particles is a naturally derived membrane in which proteins that have been synthesized in the plants are already bound to the surface of the membrane. Hence, binding of an additional protein to rubber particles that are already bound to and coated with proteins is expected to be more difficult than binding to liposomes not bound to any protein. There is also concern that the proteins already bound to rubber particles could inhibit cell-free protein synthesis. For these reasons, difficulties have been anticipated in performing cell-free protein synthesis in the presence of rubber particles. Under such circumstances, the present inventors have first discovered that rubber particles bound to a CPT family protein and a NgBR family protein can be produced by performing cell-free synthesis of the CPT family protein and the NgBR family protein in the presence of rubber particles, which had never been attempted in the past.

The protein synthesis in the presence of both rubber particles and a cell-free protein synthesis solution containing mRNAs coding for a CPT family protein and a NgBR family protein is namely the synthesis of a CPT family protein and a NgBR family protein by cell-free protein synthesis, and the synthesized CPT family protein and NgBR family protein maintain their biological functions (native state). As the cell-free protein synthesis is performed in the presence of rubber particles, the synthesized CPT family protein and NgBR family protein in their native state can be bound to the rubber particles.

Such binding of a CPT family protein and a NgBR family protein to rubber particles by protein synthesis in the presence of both the cell-free protein synthesis solution and the rubber particles means that, for example, the CPT family protein and NgBR family protein synthesized by the protein synthesis are each fully or partially incorporated into the rubber particles or inserted into the membrane structure of the rubber particles. It is not limited to these embodiments and also includes embodiments in which, for example, the proteins are localized on the surface or inside of the rubber particles. Moreover, the concept of binding to rubber particles also includes embodiments in which the proteins form a complex with another protein bound to the rubber particles as described above so as to be present in the form of the complex on the rubber particles.

The mRNAs coding for a CPT family protein and a NgBR family protein serve as translation templates that can be translated to synthesize the CPT family protein and NgBR family protein, respectively.

The origins of the mRNAs coding for a CPT family protein and a NgBR family protein are not particularly limited, and the mRNAs may be derived from microorganisms, animals, or plants, preferably plants, more preferably any of the plants mentioned above, still more preferably at least one selected from the group consisting of plants of the genera *Hevea, Sonchus, Taraxacum*, and *Parthenium*. Among these, they are particularly preferably derived from at least one species of plant selected from the group consisting of *Hevea brasiliensis, Sonchus oleraceus, Parthenium argentatum*, and *Taraxacum kok-saghyz*, most preferably *Hevea brasiliensis*. In another suitable embodiment, the mRNA coding for a CPT family protein and the mRNA coding for a NgBR family protein are derived from the same species.

The methods for preparing the mRNAs coding for a CPT family protein and a NgBR family protein are not particularly limited as long as the prepared mRNAs serve as translation templates that can be translated to synthesize the CPT family protein and NgBR family protein. For example, the mRNAs may be prepared by extracting total RNA from the latex of a rubber-producing plant by, for example, the hot phenol method, synthesizing cDNA from the total RNA, obtaining a DNA fragment of a gene coding for a CPT family protein or NgBR family protein using primers prepared based on the nucleotide sequence data of the gene coding for a CPT family protein or NgBR family protein, and performing an ordinary in vitro transcription reaction of the DNA fragment.

As long as the cell-free protein synthesis solution contains the mRNAs coding for a CPT family protein and a NgBR family protein, it may contain mRNAs coding for other proteins.

The mRNAs coding for other proteins may be ones that can be translated to express the respective proteins. The other proteins may be as described above.

In the binding step in the first invention, cell-free synthesis of a CPT family protein and a NgBR family protein is preferably performed in the presence of rubber particles. This cell-free protein synthesis may be carried out using the cell-free protein synthesis solution in a similar manner to the prior art. The cell-free protein synthesis system used may be a common cell-free protein synthesis means, such as rapid translation system RTS500 (Roche Diagnostics); or wheat germ extracts prepared in accordance with Proc. Natl. Acad. Sci. USA, 97:559-564 (2000), JP-A2000-236896, JP-A2002-125693, and JP-A 2002-204689, or cell-free protein synthesis systems using the wheat germ extracts (JP-A 2002-204689, Proc. Natl. Acad. Sci. USA, 99:14652-14657 (2002)). Systems using germ extracts are preferred among these. Thus, in another suitable embodiment of the first invention, the cell-free protein synthesis solution contains a germ extract.

The source of the germ extract is not particularly limited. From the standpoint of translation efficiency, it is preferred to use a plant-derived germ extract when a plant protein is synthesized by cell-free protein synthesis. It is particularly preferred to use a wheat-derived germ extract. Thus, in another suitable embodiment of the first invention, the germ extract is derived from wheat.

The method for preparing the germ extract is not particularly limited, and may be carried out conventionally, as described in, for example, JP-A 2005-218357.

The cell-free protein synthesis solution preferably further contains a cyclic nucleoside monophosphate derivative or a salt thereof (hereinafter, also referred to simply as "activity enhancer"). Protein synthesis activity can be further increased by the inclusion of the activity enhancer.

The cyclic nucleoside monophosphate derivative or salt thereof is not particularly limited as long as it can increase cell-free protein synthesis activity. Examples include adenosine-3',5'-cyclic monophosphoric acid and its salts; adenosine-3',5'-cyclic monophosphorothioic acid (Sp-isomer) and its salts; adenosine-3',5'-cyclic monophosphorothioic acid (Rp-isomer) and its salts; guanosine-3',5'-cyclic monophosphoric acid and its salts; guanosine-3',5'-cyclic monophosphorothioic acid (Sp-isomer) and its salts; guanosine-3',5'-cyclic monophosphorothioic acid (Rp-isomer) and its salts; 8-bromoadenosine-3',5'-cyclic monophosphoric acid (bromo-cAMP) and its salts; 8-(4-chlorophenylthio)adenosine-3',5'-cyclic monophosphoric acid (chlorophenylthio-cAMP) and its salts; 5,6-dichloro-1-β-D-ribofuranosylbenzimidazole adenosine-3',5'-cyclic monophosphoric acid (dichlororibofuranosylbenzimidazole cAMP) and its salts; adenosine-2',5'-cyclic monophosphoric acid and its salts; adenosine-2',5'-cyclic monophosphorothioic acid (Sp-isomer) and its salts; adenosine-2',5'-cyclic monophosphorothioic acid (Rp-isomer) and its salts; guanosine-2',5'-cyclic monophosphoric acid and its salts; guanosine-2',5'-cyclic monophosphorothioic acid (Sp-isomer) and its salts; and guanosine-2',5'-cyclic monophosphorothioic acid (Rp-isomer) and its salts.

The base that forms a salt with the cyclic nucleoside monophosphate derivative is not particularly limited as long as it is biochemically acceptable and forms a salt with the derivative. Preferred are, for example, alkali metal atoms such as sodium or potassium, and organic bases such as tris-hydroxyaminomethane, among others.

Of these activity enhancers, adenosine-3',5'-cyclic monophosphoric acid or adenosine-3',5'-cyclic monophosphate sodium salt is particularly preferred. These activity enhancers may be used alone, or two or more of these may be used in combination.

The activity enhancer may be incorporated into the cell-free protein synthesis solution in advance. If the activity enhancer is unstable in the solution, it is preferably added during the protein synthesis reaction performed in the presence of both the cell-free protein synthesis solution and rubber particles.

The amount of the activity enhancer added is not particularly limited as long as the activity enhancer is at a concentration that can activate (increase) the protein synthesis reaction in the cell-free protein synthesis solution. Specifically, the final concentration in the reaction system may usually be at least 0.1 millimoles/liter. The lower limit of the concentration is preferably 0.2 millimoles/liter, more preferably 0.4 millimoles/liter, particularly preferably 0.8 millimoles/liter, while the upper limit of the concentration is preferably 24 millimoles/liter, more preferably 6.4 millimoles/liter, particularly preferably 3.2 millimoles/liter.

The temperature of the cell-free protein synthesis solution to which the activity enhancer is added is not particularly limited, but is preferably 0° C. to 30° C., more preferably 10° C. to 26° C.

In addition to the mRNAs (translation templates) coding for a CPT family protein and a NgBR family protein, the cell-free protein synthesis solution also contains ATP, GTP, creatine phosphate, creatine kinase, L-amino acids, potassium ions, magnesium ions, and other components required for protein synthesis, and optionally an activity enhancer.

Such a cell-free protein synthesis solution can serve as a cell-free protein synthesis reaction system.

Since the germ extract prepared as described in JP-A 2005-218357 contains tRNA in an amount necessary for protein synthesis reaction, addition of separately prepared tRNA is not required when the germ extract prepared as above is used in the cell-free protein synthesis solution. In other words, tRNA may be added to the cell-free protein synthesis solution as necessary.

The binding step in the first invention preferably includes performing protein synthesis in the presence of both rubber particles and a cell-free protein synthesis solution containing mRNAs coding for a CPT family protein and a NgBR family protein. Specifically, this can be accomplished by adding rubber particles to the cell-free protein synthesis solution at a suitable point either before or after protein synthesis, preferably before protein synthesis.

The rubber particles are preferably present in the cell-free protein synthesis solution at a concentration of 5 to 50 g/L. In other words, 5 to 50 g of rubber particles are preferably present in 1 L of the cell-free protein synthesis solution. When the concentration of rubber particles present in the cell-free protein synthesis solution is less than 5 g/L, a rubber layer may not be formed by separation treatment (e.g. ultracentrifugation) for collecting the rubber particles bound to the synthesized CPT family protein and NgBR family protein, and therefore it may be difficult to collect the rubber particles bound to the synthesized CPT family protein and NgBR family protein. Moreover, when the concentration of rubber particles present in the cell-free protein synthesis solution exceeds 50 g/L, the rubber particles may coagulate, so that the synthesized CPT family protein and NgBR family protein may fail to bind well to the rubber particles. The concentration of rubber particles is more preferably 10 to 40 g/L, still more preferably 15 to 35 g/L, particularly preferably 15 to 30 g/L.

In the protein synthesis in the presence of both rubber particles and the cell-free protein synthesis solution, additional rubber particles may be added as appropriate as the reaction progresses. The cell-free protein synthesis solution and rubber particles are preferably present together during the period when the cell-free protein synthesis system is active, such as 3 to 48 hours, preferably 3 to 30 hours, more preferably 3 to 24 hours after the addition of rubber particles to the cell-free protein synthesis solution.

The rubber particles do not have to be subjected to any treatment, e.g. pretreatment, before use in the binding step in the first invention, preferably before being combined with the cell-free protein synthesis solution. However, proteins may be removed from the rubber particles with a surfactant beforehand to increase the proportions of the CPT family protein and NgBR family protein desired to be bound by the method of the first invention, among the proteins present on the rubber particles. Thus, in another suitable embodiment of the first invention, the rubber particles used in the first invention are washed with a surfactant before use in the binding step in the first invention, preferably before being combined with the cell-free protein synthesis solution.

The surfactant is not particularly limited, and examples include nonionic surfactants and amphoteric surfactants. Nonionic surfactants and amphoteric surfactants, among others, are suitable because they have only a little denaturing effect on the proteins on the membrane, and amphoteric surfactants are especially suitable. Thus, in another suitable embodiment of the first invention, the surfactant is an amphoteric surfactant.

These surfactants may be used alone, or two or more of these may be used in combination.

Examples of the nonionic surfactants include polyoxyalkylene ether nonionic surfactants, polyoxyalkylene ester nonionic surfactants, polyhydric alcohol fatty acid ester nonionic surfactants, sugar fatty acid ester nonionic surfactants, alkyl polyglycoside nonionic surfactants, and polyoxyalkylene polyglucoside nonionic surfactants; and polyoxyalkylene alkylamines and alkyl alkanolamides.

Polyoxyalkylene ether nonionic surfactants or polyhydric alcohol fatty acid ester nonionic surfactants are preferred among these.

Examples of the polyoxyalkylene ether nonionic surfactants include polyoxyalkylene alkyl ethers, polyoxyalkylene alkylphenyl ethers, polyoxyalkylene polyol alkyl ethers, and polyoxyalkylene mono-, di- or tristyryl phenyl ethers. Among these, polyoxyalkylene alkylphenyl ethers are suitable. The polyol is preferably a C2-C12 polyhydric alcohol, such as ethylene glycol, propylene glycol, glycerin, sorbitol, glucose, sucrose, pentaerythritol, or sorbitan.

Examples of the polyoxyalkylene ester nonionic surfactants include polyoxyalkylene fatty acid esters and polyoxyalkylene alkyl rosin acid esters.

Examples of the polyhydric alcohol fatty acid ester nonionic surfactants include fatty acid esters of C2-C12 polyhydric alcohols and fatty acid esters of polyoxyalkylene polyhydric alcohols. More specific examples include sorbitol fatty acid esters, sorbitan fatty acid esters, glycerin fatty acid esters, polyglycerin fatty acid esters, and pentaerythritol fatty acid esters, as well as polyalkylene oxide adducts of the foregoing (e.g. polyoxyalkylene sorbitan fatty acid esters, polyoxyalkylene glycerin fatty acid esters). Among these, sorbitan fatty acid esters are suitable.

Examples of the sugar fatty acid ester nonionic surfactants include fatty acid esters of sucrose, glucose, maltose, fructose, and polysaccharides, as well as polyalkylene oxide adducts of the foregoing.

Examples of the alkyl polyglycoside nonionic surfactants include those having, for example, glucose, maltose, fructose, or sucrose as the glycoside, such as alkyl glucosides, alkyl polyglucosides, polyoxyalkylene alkyl glucosides, and polyoxyalkylene alkyl polyglucosides, as well as fatty acid esters of the foregoing. Polyalkylene oxide adducts of any of the foregoing may also be used.

Examples of the alkyl groups in these nonionic surfactants include C4-C30 linear or branched, saturated or unsaturated alkyl groups. The polyoxyalkylene groups may have C2-C4 alkylene groups, and may have about 1 to 50 moles of added ethylene oxide, for example. Examples of the fatty acids include C4-C30 linear or branched, saturated or unsaturated fatty acids.

Of the nonionic surfactants, polyoxyethyleneethylene (10) octylphenyl ether (Triton X-100) or sorbitan monolaurate (Span 20) is particularly preferred for their ability to moderately remove membrane-associated proteins while keeping the membrane of rubber particles stable and, further, having only a little denaturing effect on the proteins.

Examples of the amphoteric surfactants include zwitterionic surfactants such as quaternary ammonium group/sulfonate group ($-SO_3H$) surfactants, water-soluble quaternary ammonium group/phosphate group surfactants, water-insoluble quaternary ammonium group/phosphate group surfactants, and quaternary ammonium group/carboxyl group surfactants. The acid groups in these zwitterionic surfactants may be salts.

In particular, the zwitterionic surfactant preferably has both positive and negative charges in a molecule. The acid dissociation constant (pKa) of the acid group is preferably 5 or less, more preferably 4 or less, still more preferably 3 or less.

Specific examples of the amphoteric surfactants include ammonium sulfobetaines such as 3-[3-(cholamidopropyl) dimethylamino]-2-hydroxy-1-propanesulfonate (CHAPSO), 3-[3-(cholamidopropyl)-dimethylamino]-propanesulfonate (CHAPS), N,N-bis(3-D-gluconamidopropyl)-cholamide, n-octadecyl-N,N'-dimethyl-3-amino-1-propanesulfonate, n-decyl-N,N'-dimethyl-3-amino-1-propanesulfonate, n-dodecyl-N,N'-dimethyl-3-amino-1-propanesulfonate, n-tetradecyl-N,N'-dimethyl-3-amino-1-propanesulfonate (Zwittergent™-3-14), n-hexadecyl-N,N'-dimethyl-3-amino-1-propanesulfonate, and n-octadecyl-N,N'-dimethyl-3-amino-1-propanesulfonate; phosphocholines such as n-octylphosphocholine, n-nonylphosphocholine, n-decylphosphocholine, n-dodecylphosphocholine, n-tetradecylphosphocholine, and n-hexadecylphosphocholine; and phosphatidylcholines such as dilauroyl phosphatidylcholine, dimyristoyl phosphatidylcholine, dipalmitoyl phosphatidylcholine, distearoyl phosphatidylcholine, dioleoyl phosphatidylcholine, and dilinoleoyl phosphatidylcholine. Of these, 3-[(3-cholamidopropyl)dimethylamino]-propanesulfonate (CHAPS) is particularly preferred for its ability to moderately remove proteins while keeping the membrane of rubber particles stable.

The concentration of the surfactant for the treatment is preferably within three times the critical micelle concentration (CMC) of the surfactant used. The membrane stability of the rubber particles may be reduced if they are treated with the surfactant at a concentration exceeding three times the critical micelle concentration. The concentration is more preferably within 2.5 times, still more preferably within 2.0 times the CMC. The lower limit of the concentration is preferably at least 0.05 times, more preferably at least 0.1 times, still more preferably at least 0.3 times the CMC.

Examples of reaction systems or apparatuses that can be used in the cell-free protein synthesis include a batch method (Pratt, J. M. et al., Transcription and Translation, Hames, 179-209, B. D. & Higgins, S. J., eds, IRL Press, Oxford (1984)), a continuous cell-free protein synthesis system in which amino acids, energy sources, and other components are supplied continuously to the reaction system (Spirin, A. S. et al., Science, 242, 1162-1164 (1988)), a dialysis method (Kigawa et al., 21st Annual Meeting of the Molecular Biology Society of Japan, WID 6), and an overlay method (instruction manual of PROTEIOS™ wheat germ cell-free protein synthesis core kit, Toyobo Co., Ltd.). Another method may be to supply template RNA, amino acids, energy sources, and other components as necessary to the protein synthesis reaction system, and discharge the synthesis product or decomposition product as required.

Among these, the overlay method has the advantage of easy operation, but unfortunately rubber particles disperse in the reaction solution and thus are difficult to efficiently bind to the synthesized CPT family protein and NgBR family protein. In contrast, in the dialysis method, since the amino acids used as raw materials of the CPT family protein and NgBR family protein to be synthesized can pass through the dialysis membrane but rubber particles cannot pass therethrough, the dispersal of the rubber particles can be prevented, and thus it is possible to efficiently bind the synthesized CPT family protein and NgBR family protein to the rubber particles. For this reason, the dialysis method is preferred.

The dialysis method refers to a method in which protein synthesis is carried out using the reaction solution for the cell-free protein synthesis as an internal dialysis solution, and an apparatus in which the internal dialysis solution is separated from an external dialysis solution by a dialysis membrane capable of mass transfer. Specifically, for example, a translation template is added to the synthesis reaction solution excluding the translation template, optionally after pre-incubation for an appropriate amount of time, and then the solution is put in an appropriate dialysis container as the internal reaction solution. Examples of the dialysis container include containers with a dialysis membrane attached to the bottom (e.g. Dialysis Cup 12,000 available from Daiichi Kagaku) and dialysis tubes (e.g. 12,000 available from Sanko Junyaku Co., Ltd.). The dialysis membrane used has a molecular weight cutoff of 10,000 daltons or more, preferably about 12,000 daltons.

The external dialysis solution used is a buffer containing amino acids. Dialysis efficiency can be increased by replacing the external dialysis solution with a fresh solution when the reaction speed declines. The reaction temperature and time are selected appropriately according to the protein synthesis system used. For example, in the case of a system using a wheat-derived germ extract, the reaction may be carried out usually at 10° C. to 40° C., preferably 18° C. to 30° C., more preferably 20° C. to 26° C., for 10 minutes to 48 hours, preferably for 10 minutes to 30 hours, more preferably for 10 minutes to 24 hours.

Since the mRNAs coding for a CPT family protein and a NgBR family protein contained in the cell-free protein synthesis solution are easily broken down, the mRNAs may be additionally added as appropriate during the protein synthesis reaction to make the protein synthesis more efficient. Thus, in another suitable embodiment of the first invention, the mRNAs coding for a CPT family protein and a NgBR family protein are additionally added during the protein synthesis reaction.

The addition time, the number of additions, the addition amount, and other conditions of the mRNAs are not particularly limited, and may be selected appropriately.

In the production method of the first invention, the step of collecting the rubber particles may optionally be performed after the step of binding a protein expressed by a gene coding for a cis-prenyltransferase (CPT) family protein and a protein expressed by a gene coding for a Nogo-B receptor (NgBR) family protein to rubber particles in vitro.

The rubber particle collection step may be carried out by any method that can collect the rubber particles. It may be carried out by conventional methods for collecting rubber particles. Specific examples include methods using centrifugation. When the rubber particles are collected by the centrifugation methods, the centrifugal force, centrifugation time, and centrifugation temperature may be selected appropriately so as to be able to collect the rubber particles. For example, the centrifugal force during the centrifugation is preferably 15,000×g or more, more preferably 20,000×g or more, still more preferably 25,000×g or more. Moreover, since increasing the centrifugal force too much is not expected to produce a correspondingly high separation effect, the upper limit of the centrifugal force is preferably 50,000×g or less, more preferably 45,000×g or less. The centrifugation time is preferably at least 20 minutes, more preferably at least 30 minutes, still more preferably at least 40 minutes. Moreover, since increasing the centrifugation time too much is not expected to produce a correspondingly high separation effect, the upper limit of the centrifugation time is preferably 120 minutes or less, more preferably 90 minutes or less.

From the standpoint of maintaining the activity of the CPT family protein and NgBR family protein bound to the rubber particles, the centrifugation temperature is preferably 0° C. to 10° C., more preferably 2° C. to 8° C., particularly preferably 4° C.

For example, when the cell-free protein synthesis is performed, the rubber particles and the cell-free protein synthesis solution are separated into the upper and lower layers, respectively, by the centrifugation. The cell-free protein synthesis solution as the lower layer may then be removed to collect the rubber particles bound to the CPT family protein and NgBR family protein. The collected rubber particles may be re-suspended in an appropriate buffer with a neutral pH for storage.

The rubber particles collected by the rubber particle collection step can be used in the same way as usual natural rubber without the need for further special treatment.

Moreover, the polyisoprenoid produced by the method for producing a polyisoprenoid of the first invention can be recovered by subjecting the rubber particles to the following solidification step.

The method for solidification in the solidification step is not particularly limited, and examples include a method of adding the rubber particles to a solvent that does not dissolve the polyisoprenoid (natural rubber), such as ethanol, methanol, or acetone; and a method of adding an acid to the rubber particles. Rubber (natural rubber) can be recovered as solids from the rubber particles by the solidification step. The obtained rubber (natural rubber) may be dried as necessary before use.

As described above, according to the first invention, the rubber synthesis activity of rubber particles can be increased by binding a protein expressed by a gene coding for a cis-prenyltransferase (CPT) family protein and a protein expressed by a gene coding for a Nogo-B receptor (NgBR) family protein to the rubber particles in vitro. Thus, it is possible to produce rubber (one example of polyisoprenoid) more efficiently in reaction vessels (e.g. test tubes, industrial plants).

Thus, another aspect of the first invention relates to a method for synthesizing a polyisoprenoid, which includes the step of binding a protein expressed by a gene coding for a cis-prenyltransferase (CPT) family protein and a protein expressed by a gene coding for a Nogo-B receptor (NgBR) family protein to rubber particles in vitro, for example in a reaction vessel (e.g. a test tube or industrial plant).

The step of binding a protein expressed by a gene coding for a cis-prenyltransferase (CPT) family protein and a protein expressed by a gene coding for a Nogo-B receptor (NgBR) family protein to rubber particles in vitro is as described above.

Herein, the term "polyisoprenoid" is a collective term for polymers composed of isoprene units ($C_5H_8$). Examples of the polyisoprenoid include sesterterpenes ($C_{25}$), triterpenes ($C_H$) tetraterpenes ($C_{40}$), natural rubber, and other polymers. Herein, the term "isoprenoid" refers to a compound having isoprene units ($C_5H_8$), and conceptually includes polyisoprenoids.

(Method for Producing Rubber Product)

The method for producing a rubber product of the first invention includes the steps of: kneading a polyisoprenoid produced by the method for producing a polyisoprenoid of the first invention with an additive to obtain a kneaded mixture; forming a raw rubber product from the kneaded mixture; and vulcanizing the raw rubber product.

The rubber product is not particularly limited as long as it is a rubber product that can be produced from rubber, preferably natural rubber, and examples include pneumatic tires, rubber rollers, rubber fenders, gloves, and medical rubber tubes.

When the rubber product is a pneumatic tire or, in other words, when the method for producing a rubber product of the first invention is the method for producing a pneumatic tire of the first invention, the raw rubber product forming step corresponds to the step of building a green tire from the kneaded mixture, and the vulcanization step corresponds to the step of vulcanizing the green tire. Thus, the method for producing a pneumatic tire of the first invention includes the steps of: kneading a polyisoprenoid produced by the method for producing a polyisoprenoid with an additive to obtain a kneaded mixture; building a green tire from the kneaded mixture; and vulcanizing the green tire.

<Kneading Step>

In the kneading step, the polyisoprenoid produced by the method for producing a polyisoprenoid is kneaded with an additive to obtain a kneaded mixture.

The additive is not particularly limited, and additives used in production of rubber products may be used. For example, in the case where the rubber product is a pneumatic tire, examples of the additive include rubber components other than the polyisoprenoid, reinforcing fillers such as carbon black, silica, calcium carbonate, alumina, clay, and talc, silane coupling agents, zinc oxide, stearic acid, processing aids, various antioxidants, softeners such as oils, waxes, vulcanizing agents such as sulfur, and vulcanization accelerators.

The kneading in the kneading step may be carried out using an open roll mill, a Banbury mixer, an internal mixer, or other rubber kneading machines.

<Raw Rubber Product Forming Step (Green Tire Building Step in the Case of Tire)>

In the raw rubber product forming step, a raw rubber product (green tire in the case of tire) is formed from the kneaded mixture obtained in the kneading step.

The method for forming a raw rubber product is not particularly limited, and methods used to form raw rubber products may be used appropriately. For example, in the case where the rubber product is a pneumatic tire, the kneaded mixture obtained in the kneading step may be extruded according to the shape of a tire component and then formed in a usual manner on a tire building machine and assembled with other tire components to build a green tire (unvulcanized tire).

<Vulcanization Step>

In the vulcanization step, the raw rubber product obtained in the raw rubber product forming step is vulcanized to obtain a rubber product.

The method for vulcanizing the raw rubber product is not particularly limited, and methods used to vulcanize raw rubber products may be used appropriately. For example, in the case where the rubber product is a pneumatic tire, the green tire (unvulcanized tire) obtained in the raw rubber product forming step may be vulcanized by heating and pressing in a vulcanizer to obtain a pneumatic tire.

Second Invention (Vector)

The vector of the second invention contains a nucleotide sequence in which a gene coding for a Nogo-B receptor (NgBR) family protein, or both a gene coding for a cis-prenyltransferase (CPT) family protein and a gene coding for a Nogo-B receptor (NgBR) family protein is/are functionally linked to a promoter having a promoter activity that drives laticifer-specific gene expression. By introducing such a vector into a plant for transformation, the gene coding for a protein involved in polyisoprenoid biosynthesis in the vector can be expressed specifically in laticifers, thereby enhancing cis-isoprenoid or polyisoprenoid production in the plant. This is probably because if the expression of an exogenous gene introduced for the purpose of enhancing latex productivity is promoted in sites other than laticifers, a certain load is imposed on the metabolism or latex production of the plant, thereby causing adverse effects.

Herein, "promoter having a promoter activity that drives laticifer-specific gene expression" means that the promoter has activity to control gene expression to cause a desired gene to be expressed specifically in laticifers when the desired gene is functionally linked to the promoter and introduced into a plant. The term "laticifer-specific gene expression" means that the gene is expressed substantially exclusively in laticifers with no or little expression of the gene in sites other than laticifers in plants. Also, "a gene is functionally linked to a promoter" means that the gene sequence is linked downstream of the promoter so that the gene is controlled by the promoter.

The vector of the second invention can be prepared by inserting the nucleotide sequence of a promoter having a promoter activity that drives laticifer-specific gene expression; and the nucleotide sequence of a gene coding for a Nogo-B receptor (NgBR) family protein, or both the nucleotide sequences of a gene coding for a cis-prenyltransferase (CPT) family protein and a gene coding for a Nogo-B receptor (NgBR) family protein into a vector commonly known as a plant transformation vector by conventional techniques. Examples of vectors that can be used to prepare the vector of the present invention include pBI vectors, binary vectors such as pGA482, pGAH, and pBIG, intermediate plasmids such as pLGV23Neo, pNCAT, and pMON200, and pH35GS containing GATEWAY cassette.

As long as the vector of the second invention contains: the nucleotide sequence of a promoter having a promoter activity that drives laticifer-specific gene expression; and the nucleotide sequence of a gene coding for a Nogo-B receptor (NgBR) family protein, or both the nucleotide sequences of a gene coding for a cis-prenyltransferase (CPT) family protein and a gene coding for a Nogo-B receptor (NgBR) family protein, it may contain other nucleotide sequences. Usually, the vector contains sequences derived from the vector in addition to these nucleotide sequences and further contains a restriction enzyme recognition sequence, a spacer sequence, a marker gene sequence, a reporter gene sequence, or other sequences.

Examples of the marker gene include drug-resistant genes such as a kanamycin-resistant gene, a hygromycin-resistant gene, and a bleomycin-resistant gene. The reporter gene is introduced to determine the expression site in a plant, and examples include a luciferase gene, a β-glucuronidase (GUS) gene, a green fluorescent protein (GFP), and a red fluorescent protein (RFP).

The origins of the gene coding for a cis-prenyltransferase (CPT) family protein and the gene coding for a Nogo-B receptor (NgBR) family protein are not particularly limited. They may be derived from microorganisms, animals, or plants, preferably plants, more preferably any of the plants mentioned above, still more preferably at least one selected from the group consisting of plants of the genera *Hevea, Sonchus, Taraxacum*, and *Parthenium*. Among these, they are further more preferably derived from at least one species of plant selected from the group consisting of *Hevea brasiliensis, Sonchus oleraceus, Parthenium argentatum*, and *Taraxacum kok-saghyz*, particularly preferably *Hevea brasiliensis*. Most preferably, they are both derived from *Hevea brasiliensis*. In another suitable embodiment, the gene coding for a cis-prenyltransferase (CPT) family protein and the gene coding for a Nogo-B receptor (NgBR) family protein are derived from the same species.

The gene coding for a cis-prenyltransferase (CPT) family protein, the gene coding for a Nogo-B receptor (NgBR) family protein, the CPT family protein, and the NgBR family protein used in the second invention are as described above in connection with the first invention.

As long as the vector of the second invention contains the nucleotide sequence of a promoter having a promoter activity that drives laticifer-specific gene expression; and the nucleotide sequence of a gene coding for a Nogo-B receptor (NgBR) family protein, or both the nucleotide sequences of a gene coding for a cis-prenyltransferase (CPT) family protein and a gene coding for a Nogo-B receptor (NgBR) family protein, it may contain the nucleotide sequences of genes coding for other proteins.

Examples of the genes coding for other proteins include those described above in connection with the first invention.

The promoter having a promoter activity that drives laticifer-specific gene expression is preferably at least one selected from the group consisting of a promoter of a gene coding for rubber elongation factor (REF), a promoter of a gene coding for small rubber particle protein (SRPP), a promoter of a gene coding for Hevein 2.1 (HEV2.1), and a promoter of a gene coding for MYC1 transcription factor (MYC1).

Herein, rubber elongation factor (REF) refers to a rubber particle-associated protein that is bound to rubber particles in the latex of rubber-producing plants such as *Hevea brasiliensis*, and contributes to stabilization of the rubber particles.

Small rubber particle protein (SRPP) refers to a rubber particle-associated protein that is bound to rubber particles in the latex of rubber-producing plants such as *Hevea brasiliensis*.

Hevein 2.1 (HEV2.1) refers to a protein that is highly expressed in the laticifer cells of rubber-producing plants such as *Hevea brasiliensis*. This protein is involved in coagulation of rubber particles and has antifungal activity.

MYC1 transcription factor (MYC1) refers to a transcription factor that is highly expressed in the latex of rubber-producing plants such as *Hevea brasiliensis* and is involved in jasmonic acid signaling. The term "transcription factor" means a protein having activity to increase or decrease, preferably increase, gene transcription. In other words, the MYC1 herein is a protein having activity (transcription factor activity) to increase or decrease, preferably increase, the transcription of a gene coding for at least one protein among the proteins involved in jasmonic acid signaling.

(Promoter of Gene Coding for Rubber Elongation Factor (REF))

The origin of the promoter of a gene coding for REF is not particularly limited, but the promotor is preferably derived from any of the plants mentioned above, more preferably at least one selected from the group consisting of plants of the genera *Hevea, Sonchus, Taraxacum*, and *Parthenium*. Among these, the promoter is still more preferably derived from at least one species of plant selected from the group consisting of *Hevea brasiliensis, Sonchus oleraceus, Parthenium argentatum*, and *Taraxacum kok-saghyz*, particularly preferably *Hevea brasiliensis*.

The promoter of a gene coding for REF is preferably any one of the following DNAs [A1] to [A3]:

[A1] a DNA having the nucleotide sequence represented by SEQ ID NO:9;

[A2] a DNA which hybridizes under stringent conditions to a DNA having a nucleotide sequence complementary to the nucleotide sequence represented by SEQ ID NO:9, and which has a promoter activity that drives laticifer-specific gene expression; and

[A3] a DNA having a nucleotide sequence with at least 60% sequence identity to the nucleotide sequence represented by SEQ ID NO:9, and having a promoter activity that drives laticifer-specific gene expression.

As used here, the term "hybridize" is as described above. Also, the stringent conditions are as described above.

Like the DNAs capable of hybridization under stringent conditions described above, it is known that promoters with nucleotide sequences having certain sequence identities to the original nucleotide sequence can also have promoter activity. In order to maintain the promoter activity, the sequence identity to the nucleotide sequence represented by SEQ ID NO: 9 is at least 60%, preferably at least 80%, more preferably at least 90%, still more preferably at least 95%, further more preferably at least 98%, particularly preferably at least 99%.

(Promoter of Gene Coding for SRPP)

The origin of the promoter of a gene coding for SRPP is not particularly limited, but the promoter is preferably derived from any of the plants mentioned above, more preferably at least one selected from the group consisting of plants of the genera *Hevea, Sonchus, Taraxacum*, and *Parthenium*. Among these, the promoter is still more preferably derived from at least one species of plant selected from the group consisting of *Hevea brasiliensis, Sonchus oleraceus, Parthenium argentatum*, and *Taraxacum kok-saghyz*, particularly preferably *Hevea brasiliensis*.

The promoter of a gene coding for SRPP is preferably any one of the following DNAs [B1] to [B3]:

[B1] a DNA having the nucleotide sequence represented by SEQ ID NO:10;

[B2] a DNA which hybridizes under stringent conditions to a DNA having a nucleotide sequence complementary to the nucleotide sequence represented by SEQ ID NO:10, and which has a promoter activity that drives laticifer-specific gene expression; and

[B3] a DNA having a nucleotide sequence with at least 60% sequence identity to the nucleotide sequence represented by SEQ ID NO:10, and having a promoter activity that drives laticifer-specific gene expression.

As used here, the term "hybridize" is as described above. Also, the stringent conditions are as described above.

Like the DNAs capable of hybridization under stringent conditions described above, it is known that promoters with nucleotide sequences having certain sequence identities to the original nucleotide sequence can also have promoter activity. In order to maintain the promoter activity, the sequence identity to the nucleotide sequence represented by SEQ ID NO:10 is at least 60%, preferably at least 80%, more preferably at least 90%, still more preferably at least 95%, further more preferably at least 98%, particularly preferably at least 99%.

(Promoter of Gene Coding for HEV2.1)

The origin of the promoter of a gene coding for HEV2.1 is not particularly limited, but the promoter is preferably derived from any of the plants mentioned above, more preferably at least one selected from the group consisting of plants of the genera *Hevea, Sonchus, Taraxacum*, and *Parthenium*. Among these, the promoter is still more preferably derived from at least one species of plant selected from the group consisting of *Hevea brasiliensis, Sonchus oleraceus, Parthenium argentatum*, and *Taraxacum kok-saghyz*, particularly preferably *Hevea brasiliensis*.

The promoter of a gene coding for HEV2.1 is preferably any one of the following DNAs [C1] to [C3]:

[C1] a DNA having the nucleotide sequence represented by SEQ ID NO:11;

[C2] a DNA which hybridizes under stringent conditions to a DNA having a nucleotide sequence complementary to the nucleotide sequence represented by SEQ ID NO:11, and which has a promoter activity that drives laticifer-specific gene expression; and

[C3] a DNA having a nucleotide sequence with at least 60% sequence identity to the nucleotide sequence represented by SEQ ID NO:11, and having a promoter activity that drives laticifer-specific gene expression.

As used here, the term "hybridize" is as described above. Also, the stringent conditions are as described above.

Like the DNAs capable of hybridization under stringent conditions described above, it is known that promoters with nucleotide sequences having certain sequence identities to the original nucleotide sequence can also have promoter activity. In order to maintain the promoter activity, the sequence identity to the nucleotide sequence represented by SEQ ID NO: 11 is at least 60%, preferably at least 80%, more preferably at least 90%, still more preferably at least 95%, further more preferably at least 98%, particularly preferably at least 99%.

(Promoter of Gene Coding for MYC1)

The origin of the promoter of a gene coding for MYC1 is not particularly limited, but the promoter is preferably derived from any of the plants mentioned above, more preferably at least one selected from the group consisting of plants of the genera *Hevea, Sonchus, Taraxacum*, and *Parthenium*. Among these, the promoter is still more preferably derived from at least one species of plant selected from the group consisting of *Hevea brasiliensis, Sonchus oleraceus, Parthenium argentatum*, and *Taraxacum kok-saghyz*, particularly preferably *Hevea brasiliensis*.

The promoter of a gene coding for MYC1 is preferably any one of the following DNAs [D1] to [D3]:

[D1] a DNA having the nucleotide sequence represented by SEQ ID NO:12;

[D2] a DNA which hybridizes under stringent conditions to a DNA having a nucleotide sequence complementary to the nucleotide sequence represented by SEQ ID NO:12, and which has a promoter activity that drives laticifer-specific gene expression; and

[D3] a DNA having a nucleotide sequence with at least 60% sequence identity to the nucleotide sequence represented by SEQ ID NO:12, and having a promoter activity that drives laticifer-specific gene expression.

As used here, the term "hybridize" is as described above. Also, the stringent conditions are as described above.

Like the DNAs capable of hybridization under stringent conditions described above, it is known that promoters with nucleotide sequences having certain sequence identities to the original nucleotide sequence can also have promoter activity. In order to maintain the promoter activity, the sequence identity to the nucleotide sequence represented by SEQ ID NO: 12 is at least 60%, preferably at least 80%, more preferably at least 90%, still more preferably at least 95%, further more preferably at least 98%, particularly preferably at least 99%.

Whether the DNA which hybridizes to the above-mentioned DNA under stringent conditions or the DNA having at least 60% sequence identity to the above-mentioned DNA has a promoter activity that drives laticifer-specific gene expression may be determined by conventional techniques, such as reporter assays using β-galactosidase, luciferase, green fluorescent protein (GFP), and other protein genes as reporter genes.

Conventional techniques may be employed to identify the nucleotide sequence of the promoter. For example, a genomic DNA is extracted from a growing plant by the cetyl trimethyl ammonium bromide (CTAB) method, then specific primers and random primers are designed based on the known nucleotide sequence of the promoter, and the gene including the promoter is amplified by TAIL (thermal asymmetric interlaced)-PCR using the extracted genomic DNA as a template to identify the nucleotide sequence.

The vector of the second invention (vector containing a nucleotide sequence in which a gene coding for a Nogo-B receptor (NgBR) family protein, or both a gene coding for a cis-prenyltransferase (CPT) family protein and a gene coding for a Nogo-B receptor (NgBR) family protein is/are functionally linked to a promoter having a promoter activity that drives laticifer-specific gene expression) can be introduced into a plant to produce a transgenic plant transformed to express a certain protein involved in polyisoprenoid biosynthesis specifically in laticifers. In the transgenic plant, due to the laticifer-specific expression of a certain protein involved in polyisoprenoid biosynthesis, a certain function, e.g. enzyme activity, possessed by the newly expressed protein is enhanced in the laticifers of the plant having the vector of the second invention introduced therein, whereby a part of the polyisoprenoid biosynthesis pathway is enhanced. Therefore, it is possible to enhance cis-isoprenoid or polyisoprenoid production in the plant.

Moreover, the present inventors have discovered for the first time that the rubber synthesis of rubber particles is activated by binding a CPT family protein and a NgBR family protein to the rubber particles in vitro. Based on this finding, it is anticipated that rubber synthesis activity can be increased by co-expressing a CPT family protein and a NgBR family protein in a plant. Thus, the use of a transgenic plant engineered to co-express a CPT family protein and a NgBR family protein in polyisoprenoid production is expected to result in further increased polyisoprenoid production.

Accordingly, when the transgenic plant is produced by introducing into a plant a vector containing a nucleotide sequence in which a gene coding for a Nogo-B receptor (NgBR) family protein is functionally linked to a promoter having a promoter activity that drives laticifer-specific gene expression, it is preferred to also use a vector containing a nucleotide sequence in which a gene coding for a cis-prenyltransferase (CPT) family protein is functionally linked to a promoter having a promoter activity that drives laticifer-specific gene expression. In this case, a CPT family protein and a NgBR family protein are co-expressed both in a transgenic plant produced by introducing into a plant a vector containing a nucleotide sequence in which a gene coding for a cis-prenyltransferase (CPT) family protein and a gene coding for a Nogo-B receptor (NgBR) family protein are functionally linked to a promoter having a promoter activity that drives laticifer-specific gene expression, and in a transgenic plant produced by introducing into a plant both a vector containing a nucleotide sequence in which a gene coding for a Nogo-B receptor (NgBR) family protein is functionally linked to a promoter having a promoter activity that drives laticifer-specific gene expression and a vector containing a nucleotide sequence in which a gene coding for a cis-prenyltransferase (CPT) family protein is functionally linked to a promoter having a promoter activity that drives laticifer-specific gene expression. Thus, the activity of the CPT family protein is expected to be stabilized and increased. Therefore, it is expected that the transgenic plant engineered to co-express a CPT family protein and a NgBR family protein continuously exhibits increased rubber synthesis activity, and the use of such a transgenic plant in polyisoprenoid production can more suitably result in increased polyisoprenoid production.

The vector containing a nucleotide sequence in which a gene coding for a cis-prenyltransferase (CPT) family protein is functionally linked to a promoter having a promoter activity that drives laticifer-specific gene expression refers to a vector in which the nucleotide sequence of the gene coding for a cis-prenyltransferase (CPT) family protein is linked downstream of the promoter having a promoter activity that drives laticifer-specific gene expression so that the gene is controlled by the promoter. Such a vector can be prepared as described for the vector of the second invention.

The method for preparing the transgenic plant is explained briefly below, though such a transgenic plant can be prepared by conventional methods.

The plant into which the vector of the second invention is to be introduced to produce the transgenic plant is not particularly limited, but is preferably a rubber-producing plant, among others, because improved polyisoprenoid productivity and increased polyisoprenoid production can be expected particularly when a CPT family protein and a NgBR family protein are expressed in plants capable of biosynthesizing polyisoprenoids. Among other rubber-producing plants, the plant is more preferably at least one selected from the group consisting of *Hevea brasiliensis, Sonchus oleraceus, Parthenium argentatum*, and *Taraxacum kok-saghyz*, particularly preferably *Hevea brasiliensis*.

The vector of the second invention may be introduced into a plant (including plant cells, such as calluses, cultured cells, spheroplasts, and protoplasts) by any method that introduces DNA into plant cells. Examples include methods using *Agrobacterium* (JP S59-140885 A, JP S60-70080 A, WO94/00977), electroporation (JP S60-251887 A), and methods using particle guns (gene guns) (JP 2606856 B, JP 2517813 B). The transgenic plant (transgenic plant cells) is preferably prepared by introducing the vector of the second invention into a plant by a method using *Agrobacterium* (*Agrobacterium* method), among other methods.

In addition, cis-isoprenoid or polyisoprenoid production can be performed by introducing the vector of the second invention into, for example, an organism (e.g. a microorganism, yeast, animal cell, or insect cell) or a part thereof, an organ, a tissue, a cultured cell, a spheroplast, or a protoplast, e.g., by any of the above-described DNA introduction methods.

The transgenic plant (transgenic plant cells) can be produced by the above or other methods. The transgenic plant conceptually includes not only transgenic plant cells produced by the above methods, but also all of their progeny or clones and even progeny plants obtained by passaging these cells. Once obtaining transgenic plant cells into which the vector of the second invention is introduced, progeny or clones can be produced from the transgenic plant cells by sexual or asexual reproduction, tissue culture, cell culture, cell fusion, or other techniques. Moreover, the transgenic plant cells, or their progeny or clones may be used to obtain reproductive materials (e.g. seeds, fruits, cuttings, stem tubers, root tubers, shoots, adventitious buds, adventitious embryos, calluses, protoplasts), which can then be used to produce the transgenic plant on a large scale.

Techniques to regenerate plants (transgenic plants) from transgenic plant cells are already known; for example, Doi et al. disclose techniques for *eucalyptus* (JP H11-127025 A), Fujimura et al. disclose techniques for rice (Fujimura et al., (1995), Plant Tissue Culture Lett., vol. 2: p. 74-), Shillito et al. disclose techniques for corn (Shillito et al., (1989), Bio/Technology, vol. 7: p. 581-), Visser et al. disclose techniques for potato (Visser et al., (1989), Theor. Appl. Genet., vol. 78: p. 589-), and Akama et al. disclose techniques for *Arabidopsis thaliana* (Akama et al., (1992), Plant Cell Rep., vol. 12: p. 7-). A person skilled in the art can regenerate plants from the transgenic plant cells according to these documents.

Whether a target protein gene is expressed in a regenerated plant may be determined by well-known methods. For example, Western blot analysis may be used to assess the expression of a target protein.

Seeds can be obtained from the transgenic plant, for example, as follows: the transgenic plant is rooted in an appropriate medium, transplanted to water-containing soil in a pot, and grown under proper cultivation conditions so as to finally produce seeds, which are then collected. Furthermore, plants can be grown from seeds, for example, as follows: seeds obtained from the transgenic plant as described above are sown in water-containing soil, and grown under proper cultivation conditions into plants.

According to the second invention, by introducing the vector of the second invention into a plant, the gene coding for a protein involved in polyisoprenoid biosynthesis, particularly preferably the gene coding for a CPT family protein and the gene coding for an NgBR family protein, in the vector is expressed specifically in laticifers, thereby enhancing cis-isoprenoid or polyisoprenoid production in the plant. Specifically, cis-isoprenoid or polyisoprenoid production may be carried out by culturing, for example, transgenic plant cells produced as described above, calluses obtained from the transgenic plant cells, or cells redifferentiated from the calluses in an appropriate medium, or by growing, for example, transgenic plants regenerated from the transgenic plant cells, or plants grown from seeds collected from these transgenic plants under proper cultivation conditions.

Thus, another aspect of the second invention relates to a method for enhancing cis-isoprenoid production in a plant by introducing the vector of the second invention into the plant. Furthermore, another aspect of the second invention relates to a method for enhancing polyisoprenoid production in a plant by introducing the vector of the second invention into the plant.

(Method for Producing Rubber Product)

The method for producing a rubber product of the second invention includes the steps of: kneading a polyisoprenoid produced by a transgenic plant with an additive to obtain a kneaded mixture, wherein the transgenic plant is produced by introducing the vector of the second invention into a plant; forming a raw rubber product from the kneaded mixture; and vulcanizing the raw rubber product.

The rubber product is as described above in connection with the first invention.

When the rubber product is a pneumatic tire or, in other words, when the method for producing a rubber product of the second invention is the method for producing a pneumatic tire of the second invention, the raw rubber product forming step corresponds to the step of building a green tire from the kneaded mixture, and the vulcanization step corresponds to the step of vulcanizing the green tire. Thus, the method for producing a pneumatic tire of the second invention includes the steps of: kneading a polyisoprenoid produced by a transgenic plant with an additive to obtain a kneaded mixture, wherein the transgenic plant is produced by introducing the vector of the second invention into a plant; building a green tire from the kneaded mixture; and vulcanizing the green tire.

<Kneading Step>

In the kneading step, the polyisoprenoid produced by a transgenic plant produced by introducing the vector of the second invention into a plant is kneaded with an additive to obtain a kneaded mixture.

The polyisoprenoid produced by a transgenic plant produced by introducing the vector of the second invention into a plant can be obtained by harvesting latex from the transgenic plant, and subjecting the harvested latex to the solidification step below.

The method for harvesting latex from the transgenic plant is not particularly limited, and ordinary harvesting methods may be used. For example, latex may be harvested by collecting the emulsion oozing out from the cuts in the trunk of the plant (tapping), or the emulsion oozing out from the cut roots or other parts of the transgenic plant, or by crushing the cut tissue followed by extraction with an organic solvent.

<Solidification Step>

The harvested latex is subjected to a solidification step. The method for solidification is not particularly limited, and examples include a method of adding the latex to a solvent that does not dissolve the polyisoprenoid (natural rubber), such as ethanol, methanol, or acetone; and a method of adding an acid to the latex. Rubber (natural rubber) can be recovered as solids from the latex by the solidification step. The obtained rubber (natural rubber) may be dried as necessary before use.

The additive is not particularly limited, and additives used in production of rubber products may be used. For example, in the case where the rubber product is a pneumatic tire, examples of the additive include rubber components other than the rubber obtained from the latex, reinforcing fillers such as carbon black, silica, calcium carbonate, alumina, clay, and talc, silane coupling agents, zinc oxide, stearic acid, processing aids, various antioxidants, softeners such as oils, waxes, vulcanizing agents such as sulfur, and vulcanization accelerators.

The kneading in the kneading step may be carried out using an open roll mill, a Banbury mixer, an internal mixer, or other rubber kneading machines.

<Raw Rubber Product Forming Step (Green Tire Building Step in the Case of Tire)>

The raw rubber product forming step is as described above in connection with the first invention.

<Vulcanization Step>

The vulcanization step is as described above in connection with the first invention.

EXAMPLES

The present invention is specifically explained with reference to examples, but the present invention is not limited to these examples.

Example 1

[Extraction of Total RNA from *Hevea* Latex]

Total RNA was extracted from the latex of *Hevea brasiliensis* by the hot phenol method. To 6 mL of the latex were added 6 mL of 100 mM sodium acetate buffer and 1 mL of a 10% SDS solution, and then 12 mL of water-saturated phenol pre-heated at 65° C. The mixture was incubated for five minutes at 65° C., agitated in a vortex mixer, and centrifuged at 7,000 rpm for 10 minutes at room temperature. After the centrifugation, the supernatant was transferred to a new tube, 12 mL of a phenol:chloroform (1:1) solution was added, and the mixture was agitated by shaking for two minutes. After the agitation, the resulting mixture was centrifuged again at 7,000 rpm for 10 minutes at room temperature, the supernatant was transferred to a new tube, 12 mL of a chloroform:isoamyl alcohol (24:1) solution was added, and the mixture was agitated by shaking for two minutes. After the agitation, the resulting mixture was centrifuged again at 7,000 rpm for 10 minutes at room temperature, the supernatant was transferred to a new tube, 1.2 mL of a 3M sodium acetate solution and 13 mL of isopropanol were added, and the mixture was agitated in a vortex mixer. The resulting mixture was incubated for 30 minutes at −20° C. to precipitate total RNA. The incubated mixture was centrifuged at 15,000 rpm for 10 minutes at 4° C., and the supernatant was removed to collect a precipitate of total RNA. The collected total RNA was washed twice with 70% ethanol, and dissolved in RNase-free water.

[Synthesis of cDNA from Total RNA]

cDNA was synthesized from the collected total RNA. The cDNA synthesis was carried out using a PrimeScript II 1st strand cDNA synthesis kit (Takara Bio Inc.) in accordance with the manual.

[Acquisition of CPT and NgBR Genes from cDNA]

The prepared 1st strand cDNA was used as a template to obtain CPT and NgBR genes. PCR was carried out using a KOD-plus-Neo (Toyobo Co., Ltd.) in accordance with the manual. The PCR reaction involved 35 cycles with each cycle consisting of 10 seconds at 98° C., 30 seconds at 58° C., and 1 minute at 68° C.

The CPT gene was obtained using the following primers.

```
Primer 1:
5'-tttggatccgatggaattatacaacggtgagagg-3'

Primer 2:
5'-tttgcggccgcttattttaagtattccttatgtttctcc-3'
```

The NgBR gene was obtained using the following primers.

```
Primer 3:
5'-tttctcgagatggatttgaaacctggagctg-3'

Primer 4:
5'-tttctcgagtcatgtaccataattttgctgcac-3'
```

A CPT gene (HRT1) and a NgBR gene (HRTBP) were produced as described above. The genes were sequenced to identify the full-length nucleotide sequence and amino acid sequence. The nucleotide sequence of HRT1 is given by SEQ ID NO: 1. The amino acid sequence of HRT1 is given by SEQ ID NO:2. The nucleotide sequence of HRTBP is given by SEQ ID NO:3. The amino acid sequence of HRTBP is given by SEQ ID NO:4.

[Vector Construction]

The obtained DNA fragments were subjected to dA addition and then inserted into pGEM-T Easy vectors using a pGEM-T Easy Vector System (Promega) to prepare pGEM-HRT1 and pGEM-HRTBP.

[Transformation of *Escherichia coli*]

*Escherichia coli* DH5α was transformed with the prepared vectors, the transformant was cultured on LB agar medium containing ampicillin and X-gal, and *Escherichia coli* cells carrying the introduced target genes were selected by blue/white screening.

[Plasmid Extraction]

The *Escherichia coli* cells transformed with the plasmids containing the target genes were cultured overnight at 37° C. on LB liquid medium. After the culture, the cells were collected, and the plasmids were collected. A FastGene Plasmid mini kit (Nippon Genetics Co., Ltd.) was used for plasmid collection.

It was confirmed by sequence analysis that there were no mutations in the nucleotide sequences of the collected genes inserted into the plasmids.

[Preparation of Vectors for Cell-Free Protein Synthesis]

The pGEM-HRT1 obtained in the above [Vector construction] was treated with the restriction enzymes Bam HI and Not I, and inserted into a pEU-E01-His-TEV-MCS-N2 cell-free expression vector that had been treated similarly with the restriction enzymes Bam HI and Not I to prepare pEU-His-N2-HRT1.

Similarly, pGEM-HRTBP was treated with the restriction enzyme Xho I, and inserted into a pEU-E01-MCS-TEV-His-C1 cell-free expression vector that had been treated similarly with the restriction enzyme Xho I to prepare pEU-C1-HRTBP.

[Transformation of *Escherichia coli*]

*Escherichia coli* DH5α was transformed with the prepared vectors, the transformant was cultured on LB agar medium containing ampicillin and X-gal, and *Escherichia coli* cells carrying the introduced target genes were selected by colony PCR.

[Plasmid Extraction]

The *Escherichia coli* cells transformed with the plasmids containing the target genes were cultured overnight at 37° C. on LB liquid medium. After the culture, the cells were collected, and the plasmids were collected. A FastGene Plasmid mini kit (Nippon Genetics Co., Ltd.) was used for plasmid collection.

[Preparation of Rubber Particles]

Rubber particles were prepared from *Hevea* latex by five stages of centrifugation. To 900 mL of *Hevea* latex was added 100 mL of 1 M Tris buffer (pH 7.5) containing 20 mM dithiothreitol (DTT) to prepare a latex solution. The latex solution was centrifuged in stages at the following different speeds: 1,000×g, 2,000×g, 8,000×g, 20,000×g, and 50,000× g. Each stage of centrifugation was carried out for 45 minutes at 4° C. To the rubber particle layer left after the centrifugation at 50,000×g was added 3-[(3-cholamidopropyl)dimethylamino]-propanesulfonate (CHAPS) at a final concentration of 0.1 to 2.0×CMC (0.1 to 2.0 times the critical micelle concentration CMC) to wash the rubber particles. After the washing, the rubber particles were collected by ultracentrifugation (40,000×g, 4° C., 45 minutes), and re-suspended in an equal amount of 100 M Tris buffer (pH 7.5) containing 2 mM dithiothreitol (DTT).

[Cell-Free Protein Synthesis Reaction (Step 1: mRNA Transcription Reaction)]

Cell-free protein synthesis was performed using a WEPRO7240H expression kit (CellFree Sciences Co., Ltd.). mRNA transcription reactions were performed using the vectors obtained in the above [Preparation of vectors for cell-free protein synthesis] as templates in accordance with the protocol of the WEPRO7240H expression kit.

[Purification of mRNAs]

After the transcription reactions, the resulting mRNAs were purified by ethanol precipitation.

[Cell-Free Protein Synthesis Reaction (Step 2: Protein Synthesis by Dialysis)]

The following amounts of materials were added to a dialysis cup (MWCO 12000, Bio-Teck). A total amount of 60 µL of a reaction solution was prepared according to the protocol of the WEPRO7240H expression kit. To the reaction solution was added 1 to 2 mg of the rubber particles. Separately, 650 µL of SUB-AMIX was added to a No. 2 PP container (Maruemu container).

Figure 3:
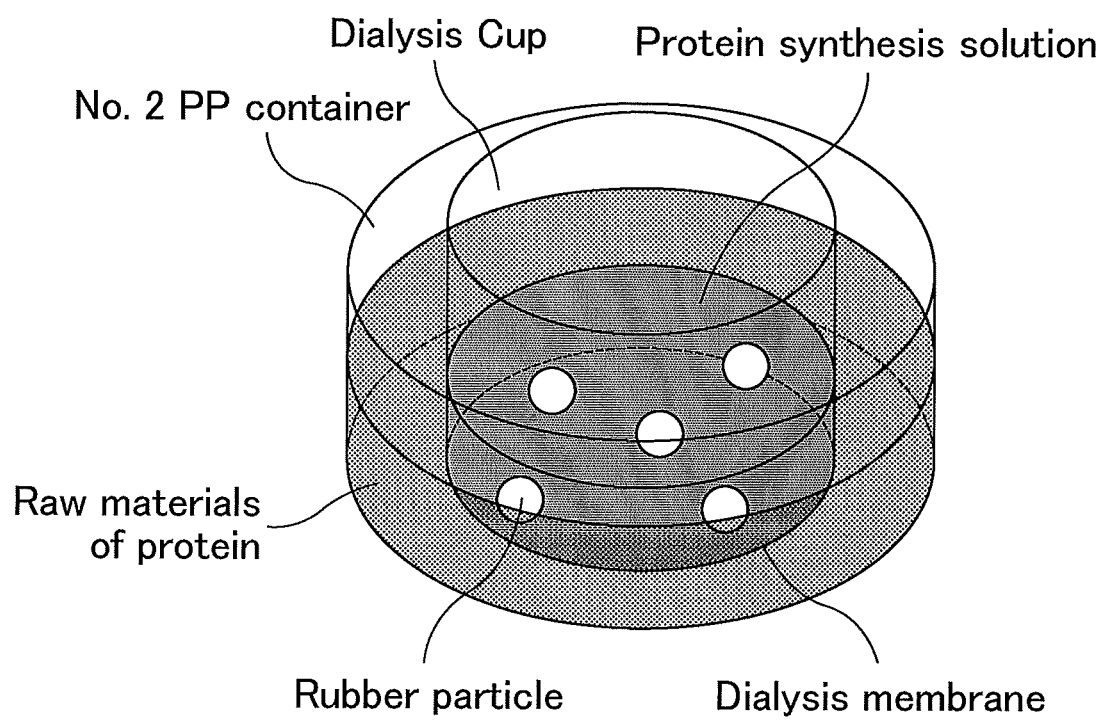
FIG. 3 is an outline diagram illustrating a dialysis process in Examples.

The dialysis cup was set in the No. 2 PP container, and a protein synthesis reaction was initiated at 26° C. The addition of the mRNAs and the replacement of the external dialysis solution (SUB-AMIX) were performed twice after the initiation of the reaction. The reaction was carried out for 24 hours. FIG. 3 shows a schematic diagram illustrating the dialysis process.

[Collection of Reacted Rubber Particles]

The solution in the dialysis cup was transferred to a new 1.5 µL tube, and the reacted rubber particles were collected by ultracentrifugation (40,000×g, 4° C., 45 minutes) and re-suspended in an equal amount of 100 M Tris buffer (pH 7.5) containing 2 mM dithiothreitol (DTT).

[Measurement of Rubber Synthesis Activity of Reacted Rubber Particles]

The rubber synthesis activity of the collected reacted rubber particles was measured as follows.

First, 50 mM Tris-HCl (pH 7.5), 2 mM DTT, 5 mM $MgCl_2$, 15 µM farnesyl diphosphate (FPP), 100 µM 1-14C isopentenyl diphosphate ([1-14C]IPP, specific activity 5 Ci/mol), and 10 µL of the rubber particle solution were mixed to prepare a reaction solution (100 µL in total), which was then reacted for 16 hours at 30° C.

After the reaction, 200 µL of saturated NaCl was added to the solution, and the mixture was extracted with 1 mL of diethyl ether to extract isopentenol and the like. Next, polyprenyl diphosphates were extracted from the aqueous phase with 1 mL of BuOH saturated with saline, and then a very long chain polyisoprenoid (natural rubber) was further extracted from the aqueous phase with 1 mL of toluene/hexane (1:1), followed by determination of radioactivity. The radioactivity of each phase was determined by $^{14}C$ counting using a liquid scintillation counter. A higher radioactivity (dpm) indicates higher natural rubber production and higher rubber synthesis activity.

Table 1 shows the results.

[Measurement of Molecular Weight Distribution of Synthesized Very Long Chain Polyisoprenoid (Natural Rubber)]

The molecular weight distribution of the very long chain polyisoprenoid (natural rubber) synthesized as described above was measured under the following conditions by radio-HPLC. FIG. 4(a) shows the results.

HPLC system: a product of GILSON
Column: TSK guard column MP(XL) available from Tosoh Corporation, TSK gel Multipore HXL-M (two columns)
Column temperature: 40° C.
Solvent: THF available from Merck
Flow rate: 1 mL/min
UV detection: 215 nm
RI detection: Ramona Star (Raytest GmbH)

Comparative Example 1

[Preparation of Rubber Particles]

The same procedure as in Example 1 was followed.

[Cell-Free Protein Synthesis Reaction (Step 1: mRNA Transcription Reaction)]

Cell-free protein synthesis was performed using a WEPRO7240H expression kit (CellFree Sciences Co., Ltd.).

An mRNA transcription reaction was performed using the cell-free expression vector pEU-E01-His-TEV-MCS-N2 as a template in accordance with the protocol of the WEPRO7240H expression kit.

[Purification of mRNA]

After the transcription reaction, the resulting mRNA was purified by ethanol precipitation.

[Cell-Free Protein Synthesis Reaction (Step 2: Protein Synthesis by Dialysis)]

The same procedure as in Example 1 was followed but using the above mRNA.

[Collection of Reacted Rubber Particles]

The reacted rubber particles were collected as in Example 1, and re-suspended in an equal amount of 100 M Tris buffer (pH 7.5) containing 2 mM dithiothreitol (DTT).

[Measurement of Rubber Synthesis Activity of Reacted Rubber Particles]

The rubber synthesis activity of the collected reacted rubber particles was measured as in Example 1.

Table 1 shows the results.

Comparative Example 2

The same procedure as in Example 1 was followed but using the pEU-C1-HRTBP obtained in the above [Preparation of vectors for cell-free protein synthesis] in Example 1 as the template for cell-free protein synthesis, and the rubber synthesis activity of the collected reacted rubber particles was measured as in Example 1.

Table 1 shows the results.

Example 2

(Synthesis of CPT and NgBR Genes of *Lactuca sativa*)

A CPT gene (LsCPT3) and a NgBR gene (LsCPTL2) of *Lactuca sativa* were produced by synthesizing a region from the start codon to the stop codon using a gene synthesis service of GenScript Japan with public databases via BLAST. For cloning into vectors for cell-free protein synthesis described later, Xho I and Kpn I sites were added to the 5' and 3' ends, respectively, of LsCPT3, and EcoRV and Xho I sites were added to the 5' and 3' ends, respectively, of LsCPTL2.

The CPT gene (LsCPT3) and NgBR gene (LsCPTL2) were produced as described above. The genes were sequenced to identify the full-length nucleotide sequence and amino acid sequence. The nucleotide sequence of LsCPT3 is given by SEQ ID NO:13. The amino acid sequence of LsCPT3 is given by SEQ ID NO:14. The nucleotide sequence of LsCPTL2 is given by SEQ ID NO:15. The amino acid sequence of LsCPTL2 is given by SEQ ID NO:16.

[Vector Construction]

The obtained DNA fragments were inserted into pUC57 to prepare pUC57-LsCPT3 and pUC57-LsCPTL2.

[Transformation of *Escherichia coli*]

The same procedure as in Example 1 was followed but using the prepared vectors.

[Plasmid Extraction]

The same procedure as in Example 1 was followed.

[Preparation of Vectors for Cell-Free Protein Synthesis]

The pUC57-LsCPT3 obtained in the above [Vector construction] was treated with the restriction enzymes Xho I and Kpn I, and inserted into a pEU-E01-His-TEV-MCS-N2 cell-free expression vector that had been treated similarly with the restriction enzymes Xho I and Kpn I to prepare pEU-His-N2-LsCPT3.

Similarly, pUC57-LsCPTL2 was treated with the restriction enzymes EcoRV and Xho I, and inserted into a pEU-E01-MCS-TEV-His-C1 cell-free expression vector that had been treated similarly with the restriction enzymes EcoRV and Xho I to prepare pEU-C1-LsCPTL2.

[Transformation of *Escherichia coli*]

The same procedure as in Example 1 was followed but using the prepared vectors.

[Plasmid Extraction]

The same procedure as in Example 1 was followed.

[Preparation of Rubber Particles]

The same procedure as in Example 1 was followed.

[Cell-Free Protein Synthesis Reaction (Step 1: mRNA Transcription Reaction)]

Cell-free protein synthesis was performed using a WEPRO7240H expression kit (CellFree Sciences Co., Ltd.). mRNA transcription reactions were performed using the vectors obtained in the above [Preparation of vectors for cell-free protein synthesis] as templates in accordance with the protocol of the WEPRO7240H expression kit.

[Purification of mRNAs]

After the transcription reactions, the resulting mRNAs were purified by ethanol precipitation.

[Cell-Free Protein Synthesis Reaction (Step 2: Protein Synthesis by Dialysis)]

The same procedure as in Example 1 was followed but using the above mRNAs.

[Collection of Reacted Rubber Particles]

The reacted rubber particles were collected as in Example 1, and re-suspended in an equal amount of 100 M Tris buffer (pH 7.5) containing 2 mM dithiothreitol (DTT).

[Measurement of Rubber Synthesis Activity of Reacted Rubber Particles]

The rubber synthesis activity of the collected reacted rubber particles was measured as in Example 1. Table 1 shows the results.

[Measurement of Molecular Weight Distribution of Synthesized Very Long Chain Polyisoprenoid (Natural Rubber)]

Figure 4:
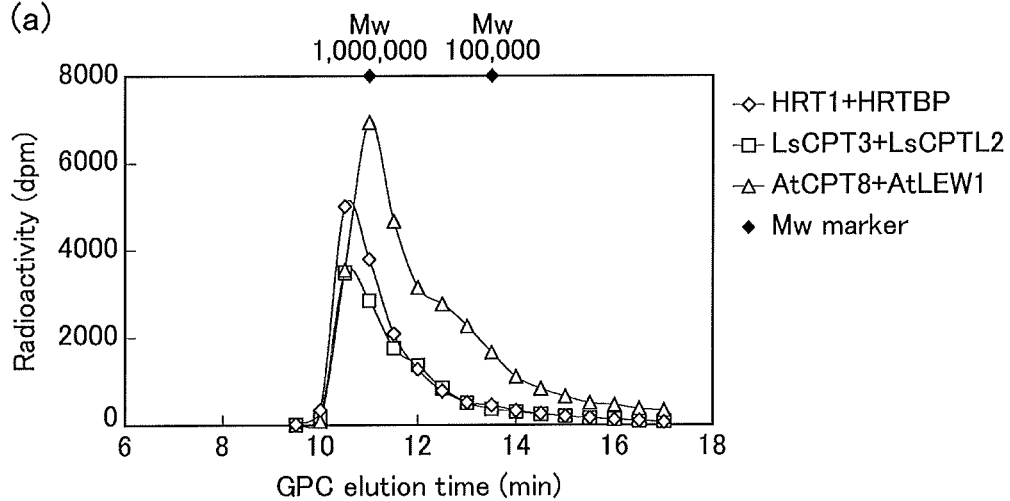
FIG. 4 illustrates graphs of the measured molecular weight distributions of the very long chain polyisoprenoids (natural rubbers) synthesized in Examples 1 to 3 (FIG. 4(a)), Reference Examples 1 to 4 (FIG. 4(b)), and Reference Examples 5 and 6 (FIG. 4(c)).
Figure 4:
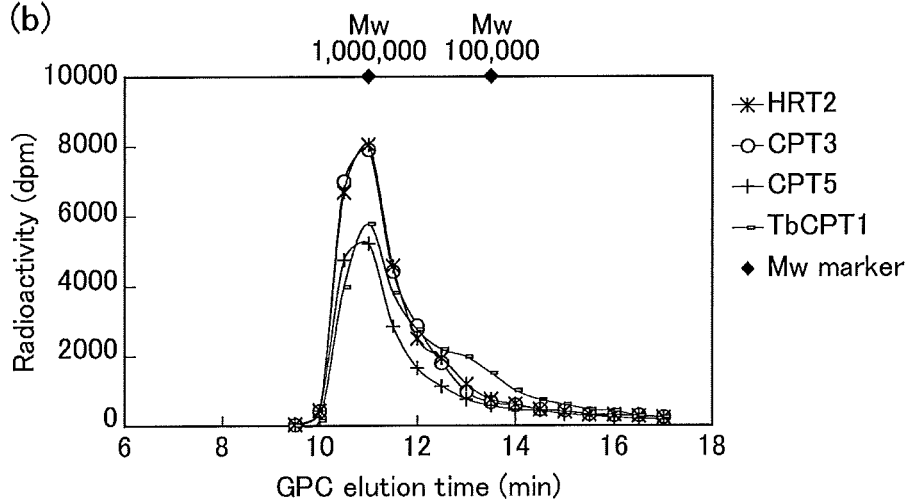
Figure 4:
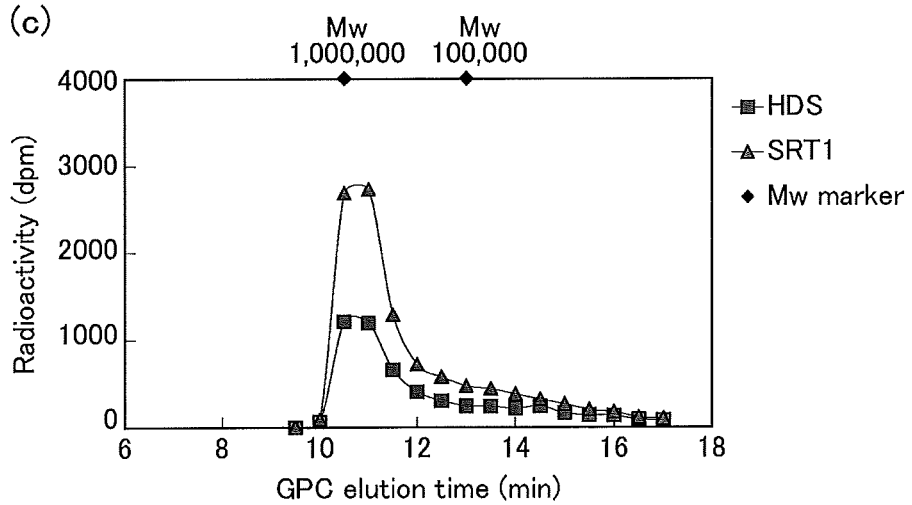

The molecular weight distribution of the very long chain polyisoprenoid (natural rubber) synthesized in the above [Measurement of rubber synthesis activity of reacted rubber particles] was measured as in Example 1. FIG. 4(*a*) shows the results.

Example 3

[Extraction of Total RNA from *Arabidopsis thaliana*]

Total RNA was extracted from *Arabidopsis thaliana* by the hot phenol method. A seedling frozen with liquid nitrogen was ground in a mortar. Thereto were added 400 µL of water-saturated phenol (80° C.) and 400 µL of a RNA extraction buffer (80° C., 100 mM LiCl, 100 mM Tris-HCl (pH 8.0), 10 mM EDTA, and 1% SDS), followed by vortex for 30 seconds. Thereto was added 400 µL of chloroform/isoamyl alcohol (24:1), followed by vortex for 30 seconds. The mixture was centrifuged at 4° C. and 15,000 rpm for 15 minutes, and the upper phase was collected. The upper phase was mixed with 500 µL of 4M LiCl, and then left at −80° C. for one hour. The mixture was centrifuged at 4° C. and 15,000 rpm for 15 minutes, and the supernatant was removed to obtain a precipitate, which was then dissolved in 400 µL of DEPC-treated water. The solution was mixed with 880 µL of ethanol and 40 µL of 3M NaOAc. The mixture was centrifuged at 4° C. and 15,000 rpm for 15 minutes, and the supernatant was removed to obtain a precipitate, which was then washed with 300 µL of 70% ethanol. The mixture was centrifuged at 4° C. and 15,000 rpm for five minutes, and the supernatant was removed to obtain a precipitate, which was then dissolved in 30 µL of DEPC-treated water. In order to remove any genomic DNA contaminant from the extracted total RNA, DNase treatment was performed using DNase I (Takara Bio Inc.) or DNase I recombinant, RNase-free (Roche). In either case, 50 µL of a reaction solution was prepared under the conditions recommended by the manufacturer, and then incubated at 37° C. for 30 minutes. After the reaction, the solution was mixed with 350 µL of DEPC-treated water and 400 µL of phenol, and centrifuged at room temperature and 15,000 rpm for 15 minutes. The upper phase was collected and mixed with 880 µL of ethanol and 40 µL of 3M NaOAc. The mixture was centrifuged at 4° C. and 15,000 rpm for 15 minutes, and the supernatant was removed to obtain a precipitate, which was then washed with 300 µL of 70% ethanol. The mixture was centrifuged at 4° C. and 15,000 rpm, and the supernatant was removed to obtain a precipitate, which was then dissolved in 50 µL of DEPC-treated water.

[Synthesis of cDNA from Total RNA]

The same procedure as in Example 1 was followed.

[Acquisition of CPT and NgBR Genes from cDNA]

The prepared 1st strand cDNA was used as a template to obtain CPT and NgBR genes. PCR was carried out using a KOD-plus-Neo (Toyobo Co., Ltd.) in accordance with the manual. The PCR reaction involved 35 cycles with each cycle consisting of 10 seconds at 98° C., 15 seconds at 55° C. to 60° C., and 30 seconds at 68° C.

The CPT gene was obtained using the following primers.

```
Primer 5:
5'-ctaggatccgagatgaatacccctagaag-3'

Primer 6:
5'-aacggatccaactatctaatcgagc-3'
```

The NgBR gene was obtained using the following primers.

```
Primer 7:
5'-cgggatccatggattcgaatcaatcgatgcggctcctc-3'

Primer 8:
5'-gcggatccaattgggaacagtagtggctgcactgactc-3'
```

[Vector Construction]

A CPT gene (AtCPT8) and a NgBR gene (AtLEW1) were produced as described above. The genes were treated with the restriction enzyme BamH I, and inserted into pBluescript IISK (−) that had been treated similarly with the restriction enzyme BamH I to prepare pBS-AtCPT8 and pBS-AtLEW1.

[Transformation of *Escherichia coli*]

The same procedure as in Example 1 was followed but using the prepared vectors.

[Plasmid Extraction]

The same procedure as in Example 1 was followed.

The genes in the plasmids were sequenced to identify the full-length nucleotide sequence and amino acid sequence. The nucleotide sequence of AtCPT8 is given by SEQ ID NO:21. The amino acid sequence of AtCPT8 is given by SEQ ID NO:22. The nucleotide sequence of AtLEW1 is given by SEQ ID NO:23. The amino acid sequence of AtLEW1 is given by SEQ ID NO:24.

The obtained pBS-AtCPT8 and pBS-AtLEW1 were used as templates to obtain CPT and NgBR genes. PCR was carried out using a KOD-plus-Neo (Toyobo Co., Ltd.) in accordance with the manual. The PCR reaction involved 35 cycles with each cycle consisting of 10 seconds at 98° C., 15 seconds at 55° C. to 60° C., and 30 seconds at 68° C.

The CPT gene was obtained using the following primers.

```
Primer 23:
5'-tatcccgggatgaataacc-3'

Primer 24:
5'-tgaactagtctaatcgagcttttc-3'
```

The NgBR gene was obtained using the following primers.

```
Primer 25:
5'-acccgggatggattcg-3'

Primer 26:
5'-cgcggactagtttaagttccatag-3'
```

[Preparation of Vectors for Cell-Free Protein Synthesis]

The genes obtained as described above were treated with the restriction enzymes Xma I and Spe I, and inserted into a pEU-E01-His-TEV-MCS-N2 cell-free expression vector that had been treated similarly with the restriction enzymes Xma I and Spe I to prepare pEU-His-N2-AtCPT8 and pEU-His-N2-AtLEW1.

[Transformation of *Escherichia coli*]

The same procedure as in Example 1 was followed but using the prepared vectors.

[Plasmid Extraction]

The same procedure as in Example 1 was followed.

[Preparation of Rubber Particles]

The same procedure as in Example 1 was followed.

[Cell-Free Protein Synthesis Reaction (Step 1: mRNA Transcription Reaction)]

Cell-free protein synthesis was performed using a WEPRO7240H expression kit (CellFree Sciences Co., Ltd.). mRNA transcription reactions were performed using the vectors obtained in the above [Preparation of vectors for cell-free protein synthesis] as templates in accordance with the protocol of the WEPRO7240H expression kit.

[Purification of mRNAs]

After the transcription reactions, the resulting mRNAs were purified by ethanol precipitation.

[Cell-Free Protein Synthesis Reaction (Step 2: Protein Synthesis by Dialysis)]

The same procedure as in Example 1 was followed but using the above mRNAs.

[Collection of Reacted Rubber Particles]

The reacted rubber particles were collected as in Example 1, and re-suspended in an equal amount of 100 M Tris buffer (pH 7.5) containing 2 mM dithiothreitol (DTT).

[Measurement of Rubber Synthesis Activity of Reacted Rubber Particles]

The rubber synthesis activity of the collected reacted rubber particles was measured as in Example 1. Table 1 shows the results.

[Measurement of Molecular Weight Distribution of Synthesized Very Long Chain Polyisoprenoid (Natural Rubber)]

The molecular weight distribution of the very long chain polyisoprenoid (natural rubber) synthesized in the above [Measurement of rubber synthesis activity of reacted rubber particles] was measured as in Example 1. FIG. 4(*a*) shows the results.

TABLE 1

| | Bound protein | Radioactivity (dpm) |
|---|---|---|
| Comparative Example 1 | None | 7500 |
| Comparative Example 2 | HRTBP | 5800 |
| Example 1 | HRT1 + HRTBP | 15500 |
| Example 2 | LsCPT3 + LsCPTL2 | 17500 |
| Example 3 | AtCPT8 + AtLEW1 | 12000 |

Table 1 shows that by binding a CPT family protein and a NgBR family protein to rubber particles, the rubber synthesis activity of the rubber particles was significantly increased as compared to when these proteins was bound alone to rubber particles. Furthermore, in Comparative Example 2 in which NgBR was bound alone to rubber particles, the rubber synthesis activity was lower than in Comparative Example 1 with no bound proteins. From these results, it is understood that the combination of a CPT family protein and a NgBR family protein has a synergistic effect that is greater than the sum of their individual effects. Thus, such an effect of significantly increasing the rubber synthesis activity of rubber particles can only be achieved by the specific combination of a CPT family protein and a NgBR family protein, which could not be predicted even by those skilled in the art.

FIG. 4 (*a*) shows that the natural rubbers synthesized in Examples 1 to 3 have peaks at substantially the same GPC elution times, indicating that the synthesized natural rubbers have comparable molecular weight distribution patterns. In FIG. 4, peak heights cannot be used to compare activities because they were not standardized among samples.

Example 4

[Acquisition of REF Gene from cDNA]

The 1st strand cDNA prepared in [Synthesis of cDNA from total RNA] in Example 1 was used as a template to obtain a REF gene. PCR was carried out using a KOD-plus-Neo (Toyobo Co., Ltd.) in accordance with the manual. The PCR reaction involved 35 cycles with each cycle consisting of 10 seconds at 98° C., 30 seconds at 58° C., and 1 minute at 68° C.

The REF gene was obtained using the following primers.

```
Primer 9:
5'-tttctcgagatggctgaagacgaagac-3'

Primer 10:
5'-tttggatcctcaattctctccataaaac-3'
```

A REF gene was produced as described above. The gene was sequenced to identify the full-length nucleotide sequence and amino acid sequence. The nucleotide sequence of REF is given by SEQ ID NO:27. The amino acid sequence of REF is given by SEQ ID NO:28.

[Vector Construction]

The obtained DNA fragment was subjected to dA addition and then inserted into pGEM-T Easy vector using a pGEM-T Easy Vector System (Promega) to prepare pGEM-REF.

[Transformation of *Escherichia coli*]

The same procedure as in Example 1 was followed but using the prepared vector.

[Plasmid Extraction]

The same procedure as in Example 1 was followed.

[Preparation of Vector for Cell-Free Protein Synthesis]

The pGEM-REF obtained in the above [Vector construction] was treated with the restriction enzymes Xho I and Bam HI, and inserted into a pEU-E01-MCS-TEV-His-C1 cell-free expression vector that had been treated similarly with the restriction enzymes Xho I and Bam HI to prepare pEU-C1-REF.

[Transformation of *Escherichia coli*]

The same procedure as in Example 1 was followed but using the prepared vector.

[Plasmid Extraction]

The same procedure as in Example 1 was followed.

[Preparation of Rubber Particles]

The same procedure as in Example 1 was followed.

[Cell-Free Protein Synthesis Reaction (Step 1: mRNA Transcription Reaction)]

Cell-free protein synthesis was performed using a WEPRO7240H expression kit (CellFree Sciences Co., Ltd.). mRNA transcription reactions were performed using the vector pEU-C1-REF obtained in the above [Preparation of vector for cell-free protein synthesis] and the vectors pEU-His-N2-HRT1 and pEU-C1-HRTBP obtained in [Preparation of vectors for cell-free protein synthesis] in Example 1 as templates in accordance with the protocol of the WEPRO7240H expression kit.

[Purification of mRNAs]

After the transcription reactions, the resulting mRNAs were purified by ethanol precipitation.

[Cell-Free Protein Synthesis Reaction (Step 2: Protein Synthesis by Dialysis)]

The same procedure as in Example 1 was followed but using the above mRNAs.

[Collection of Reacted Rubber Particles]

The reacted rubber particles were collected as in Example 1, and re-suspended in an equal amount of 100 M Tris buffer (pH 7.5) containing 2 mM dithiothreitol (DTT).

[Measurement of Rubber Synthesis Activity of Reacted Rubber Particles]

The rubber synthesis activity of the collected reacted rubber particles was measured as in Example 1.

The results confirmed that a natural rubber was synthesized, and the collected reacted rubber particles had rubber synthesis activity.

Example 5

[Acquisition of CPT Gene from cDNA]

The 1st strand cDNA prepared in [Synthesis of cDNA from total RNA] in Example 1 was used as a template to obtain a CPT gene. PCR was carried out using a KOD-plus-Neo (Toyobo Co., Ltd.) in accordance with the manual. The PCR reaction involved 35 cycles with each cycle consisting of 10 seconds at 98° C., 30 seconds at 58° C., and 1 minute at 68° C.

The CPT gene was obtained using the following primers.

```
Primer 11:
5'-tttggatccgatggaattatacaacggtgagagg-3'

Primer 12:
5'-tttgcggccgcttattttaagtattccttatgtttctcc-3
```

A CPT gene (HRT2) was produced as described above. The gene was sequenced to identify the full-length nucleotide sequence and amino acid sequence. The nucleotide sequence of HRT2 is given by SEQ ID NO:31. The amino acid sequence of HRT2 is given by SEQ ID NO:32.

[Vector Construction]

The obtained DNA fragment was subjected to dA addition and then inserted into pGEM-T Easy vector using a pGEM-T Easy Vector System (Promega) to prepare pGEM-HRT2.

[Transformation of *Escherichia coli*]

The same procedure as in Example 1 was followed but using the prepared vector.

[Plasmid Extraction]

The same procedure as in Example 1 was followed.

[Preparation of Vector for Cell-Free Protein Synthesis]

The pGEM-HRT2 obtained in the above [Vector construction] was treated with the restriction enzymes Bam HI and Not I, and inserted into a pEU-E01-His-TEV-MCS-N2 cell-free expression vector that had been treated similarly with the restriction enzymes Bam HI and Not I to prepare pEU-His-N2-HRT2.

[Transformation of *Escherichia coli*]

The same procedure as in Example 1 was followed but using the prepared vector.

[Plasmid Extraction]

The same procedure as in Example 1 was followed.

[Preparation of Rubber Particles]

The same procedure as in Example 1 was followed.

[Cell-Free Protein Synthesis Reaction (Step 1: mRNA Transcription Reaction)]

Cell-free protein synthesis was performed using a WEPRO7240H expression kit (CellFree Sciences Co., Ltd.). mRNA transcription reactions were performed using the vector pEU-His-N2-HRT2 obtained in the above [Preparation of vector for cell-free protein synthesis], the vector pEU-C1-HRTBP in [Preparation of vectors for cell-free protein synthesis] in Example 1, and the vector pEU-C1-REF obtained in [Preparation of vector for cell-free protein synthesis] in Example 4 as templates in accordance with the protocol of the WEPRO7240H expression kit.

[Purification of mRNAs]

After the transcription reactions, the resulting mRNAs were purified by ethanol precipitation.

[Cell-Free Protein Synthesis Reaction (Step 2: Protein Synthesis by Dialysis)]

The same procedure as in Example 1 was followed but using the above mRNAs.

[Collection of Reacted Rubber Particles]

The reacted rubber particles were collected as in Example 1, and re-suspended in an equal amount of 100 M Tris buffer (pH 7.5) containing 2 mM dithiothreitol (DTT).

[Measurement of Rubber Synthesis Activity of Reacted Rubber Particles]

The rubber synthesis activity of the collected reacted rubber particles was measured as in Example 1.

The results confirmed that a natural rubber was synthesized, and the collected reacted rubber particles had rubber synthesis activity.

Example 6

[Acquisition of CPT Gene from cDNA]

The 1st strand cDNA prepared in [Synthesis of cDNA from total RNA] in Example 1 was used as a template to obtain a CPT gene. PCR was carried out using a KOD-plus-Neo (Toyobo Co., Ltd.) in accordance with the manual. The PCR reaction involved 35 cycles with each cycle consisting of 10 seconds at 98° C., 30 seconds at 58° C., and 1 minute at 68° C.

The CPT gene was obtained using the following primers.

```
Primer 13:
5'-atacccgggatggaaatatatac-3'

Primer 14:
5'-actcccgggttattttaaatattc-3'
```

A CPT gene (CPT3) was produced as described above. The gene was sequenced to identify the full-length nucleotide sequence and amino acid sequence. The nucleotide sequence of CPT3 is given by SEQ ID NO:35. The amino acid sequence of CPT3 is given by SEQ ID NO:36.

[Vector Construction]

The obtained DNA fragment was subjected to dA addition and then inserted into pGEM-T Easy vector using a pGEM-T Easy Vector System (Promega) to prepare pGEM-CPT3.

[Transformation of *Escherichia coli*]

The same procedure as in Example 1 was followed but using the prepared vector.

[Plasmid Extraction]

The same procedure as in Example 1 was followed.

[Preparation of Vector for Cell-Free Protein Synthesis]

The pGEM-CPT3 obtained in the above [Vector construction] was treated with the restriction enzyme Xma I, and inserted into a pEU-E01-His-TEV-MCS-N2 cell-free expression vector that had been treated similarly with the restriction enzyme Xma I to prepare pEU-His-N2-CPT3.

[Transformation of *Escherichia coli*]

The same procedure as in Example 1 was followed but using the prepared vector.

[Plasmid Extraction]

The same procedure as in Example 1 was followed.

[Preparation of Rubber Particles]

The same procedure as in Example 1 was followed.

[Cell-Free Protein Synthesis Reaction (Step 1: mRNA Transcription Reaction)]

Cell-free protein synthesis was performed using a WEPRO7240H expression kit (CellFree Sciences Co., Ltd.). mRNA transcription reactions were performed using the vector pEU-His-N2-CPT3 obtained in the above [Preparation of vector for cell-free protein synthesis], the vector pEU-C1-HRTBP in [Preparation of vectors for cell-free protein synthesis] in Example 1, and the vector pEU-C1-REF obtained in [Preparation of vector for cell-free protein synthesis] in Example 4 as templates in accordance with the protocol of the WEPRO7240H expression kit.

[Purification of mRNAs]

After the transcription reactions, the resulting mRNAs were purified by ethanol precipitation.

[Cell-Free Protein Synthesis Reaction (Step 2: Protein Synthesis by Dialysis)]

The same procedure as in Example 1 was followed but using the above mRNAs.

[Collection of Reacted Rubber Particles]

The reacted rubber particles were collected as in Example 1, and re-suspended in an equal amount of 100 M Tris buffer (pH 7.5) containing 2 mM dithiothreitol (DTT).

[Measurement of Rubber Synthesis Activity of Reacted Rubber Particles]

The rubber synthesis activity of the collected reacted rubber particles was measured as in Example 1.

The results confirmed that a natural rubber was synthesized, and the collected reacted rubber particles had rubber synthesis activity.

Example 7

[Acquisition of CPT Gene from cDNA]

The 1st strand cDNA prepared in [Synthesis of cDNA from total RNA] in Example 1 was used as a template to obtain a CPT gene. PCR was carried out using a KOD-plus-Neo (Toyobo Co., Ltd.) in accordance with the manual. The PCR reaction involved 35 cycles with each cycle consisting of 10 seconds at 98° C., 30 seconds at 58° C., and 1 minute at 68° C.

The CPT gene was obtained using the following primers.

```
Primer 15:
5'-tatcccgggatggaaata-3'

Primer 16:
5'-atacccgggttacaactgc-3'
```

A CPT gene (CPT5) was produced as described above. The gene was sequenced to identify the full-length nucleotide sequence and amino acid sequence. The nucleotide sequence of CPT5 is given by SEQ ID NO:40. The amino acid sequence of CPT5 is given by SEQ ID NO:41.

[Vector Construction]

The obtained DNA fragment was subjected to dA addition and then inserted into pGEM-T Easy vector using a pGEM-T Easy Vector System (Promega) to prepare pGEM-CPT5.

[Transformation of *Escherichia coli*]

The same procedure as in Example 1 was followed but using the prepared vector.

[Plasmid Extraction]

The same procedure as in Example 1 was followed.

[Preparation of Vector for Cell-Free Protein Synthesis]

The pGEM-CPT5 obtained in the above [Vector construction] was treated with the restriction enzyme Xma I, and inserted into a pEU-E01-His-TEV-MCS-N2 cell-free expression vector that had been treated similarly with the restriction enzyme Xma I to prepare pEU-His-N2-CPT5.

[Transformation of *Escherichia coli*]

The same procedure as in Example 1 was followed but using the prepared vector.

[Plasmid Extraction]

The same procedure as in Example 1 was followed.

[Preparation of Rubber Particles]

The same procedure as in Example 1 was followed.

[Cell-Free Protein Synthesis Reaction (Step 1: mRNA Transcription Reaction)]

Cell-free protein synthesis was performed using a WEPRO7240H expression kit (CellFree Sciences Co., Ltd.). mRNA transcription reactions were performed using the vector pEU-His-N2-CPT5 obtained in the above [Preparation of vector for cell-free protein synthesis], the vector pEU-C1-HRTBP in [Preparation of vectors for cell-free protein synthesis] in Example 1, and the vector pEU-C1-REF obtained in [Preparation of vector for cell-free protein synthesis] in Example 4 as templates in accordance with the protocol of the WEPRO7240H expression kit.

[Purification of mRNAs]

After the transcription reactions, the resulting mRNAs were purified by ethanol precipitation.

[Cell-Free Protein Synthesis Reaction (Step 2: Protein Synthesis by Dialysis)]

The same procedure as in Example 1 was followed but using the above mRNAs.

[Collection of Reacted Rubber Particles]

The reacted rubber particles were collected as in Example 1, and re-suspended in an equal amount of 100 M Tris buffer (pH 7.5) containing 2 mM dithiothreitol (DTT).

[Measurement of Rubber Synthesis Activity of Reacted Rubber Particles]

The rubber synthesis activity of the collected reacted rubber particles was measured as in Example 1.

The results confirmed that a natural rubber was synthesized, and the collected reacted rubber particles had rubber synthesis activity.

Reference Example 1

[Synthesis of CPT Gene of *Taraxacum brevicorniculatum*]

A CPT gene (TbCPT1) of *Taraxacum brevicorniculatum* was produced by synthesizing a region from the start codon to the stop codon using a gene synthesis service of GenScript Japan with public databases via BLAST. For cloning into a vector for cell-free protein synthesis described later, Xho I and Kpn I sites were added to the 5' and 3' ends, respectively, of TbCPT1.

A CPT gene (TbCPT1) was produced as described above. The gene was sequenced to identify the full-length nucleotide sequence and amino acid sequence. The nucleotide sequence of TbCPT1 is given by SEQ ID NO:42. The amino acid sequence of TbCPT1 is given by SEQ ID NO:43.

[Vector Construction]

The obtained DNA fragment was inserted into pUC57 to prepare pUC57-TbCPT1.

[Transformation of *Escherichia coli*]

The same procedure as in Example 1 was followed but using the prepared vector.

[Plasmid Extraction]

The same procedure as in Example 1 was followed.

[Preparation of Vector for Cell-Free Protein Synthesis]

The pUC57-TbCPT1 obtained in the above [Vector construction] was treated with the restriction enzymes Xho I and Kpn I, and inserted into a pEU-E01-His-TEV-MCS-N2 cell-free expression vector that had been treated similarly with the restriction enzymes Xho I and Kpn I to prepare pEU-His-N2-TbCPT1.

[Transformation of *Escherichia coli*]

The same procedure as in Example 1 was followed but using the prepared vector.

[Plasmid Extraction]

The same procedure as in Example 1 was followed.

[Preparation of Rubber Particles]

The same procedure as in Example 1 was followed.

[Cell-Free Protein Synthesis Reaction (Step 1: mRNA Transcription Reaction)]

Cell-free protein synthesis was performed using a WEPRO7240H expression kit (CellFree Sciences Co., Ltd.). An mRNA transcription reaction was performed using the vector obtained in the above [Preparation of vector for cell-free protein synthesis] as a template in accordance with the protocol of the WEPRO7240H expression kit.

[Purification of mRNA]

After the transcription reaction, the resulting mRNA was purified by ethanol precipitation.

[Cell-Free Protein Synthesis Reaction (Step 2: Protein Synthesis by Dialysis)]

The same procedure as in Example 1 was followed but using the above mRNA.

[Collection of Reacted Rubber Particles]

The reacted rubber particles were collected as in Example 1, and re-suspended in an equal amount of 100 M Tris buffer (pH 7.5) containing 2 mM dithiothreitol (DTT).

[Measurement of Rubber Synthesis Activity of Reacted Rubber Particles]

The rubber synthesis activity of the collected reacted rubber particles was measured as in Example 1.

The results confirmed that a natural rubber was synthesized, and the collected reacted rubber particles had rubber synthesis activity.

[Measurement of Molecular Weight Distribution of Synthesized Very Long Chain Polyisoprenoid (Natural Rubber)]

The molecular weight distribution of the very long chain polyisoprenoid (natural rubber) synthesized in the above [Measurement of rubber synthesis activity of reacted rubber particles] was measured as in Example 1. FIG. 4(b) shows the results. FIG. 4(b) shows that the natural rubber synthesized in Reference Example 1 has a peak at substantially the same GPC elution time as the natural rubbers synthesized in Examples 1 to 3, indicating that the synthesized natural rubber has a comparable molecular weight distribution pattern.

These results strongly suggest that, by additionally binding a NgBR family protein to the rubber particles so that both TbCPT1 protein and the NgBR family protein are bound to the rubber particles, the activity of TbCPT1 protein on the rubber particles is stabilized and increased, thereby increasing the rubber synthesis activity of the rubber particles.

Reference Example 2

[Preparation of Rubber Particles]

The same procedure as in Example 1 was followed.

[Cell-Free Protein Synthesis Reaction (Step 1: mRNA Transcription Reaction)]

Cell-free protein synthesis was performed using a WEPRO7240H expression kit (CellFree Sciences Co., Ltd.). An mRNA transcription reaction was performed using the vector pEU-His-N2-HRT2 obtained in [Preparation of vector for cell-free protein synthesis] in Example 5 as a template in accordance with the protocol of the WEPRO7240H expression kit.

[Purification of mRNA]

After the transcription reaction, the resulting mRNA was purified by ethanol precipitation.

[Cell-Free Protein Synthesis Reaction (Step 2: Protein Synthesis by Dialysis)]

The same procedure as in Example 1 was followed but using the above mRNA.

[Collection of Reacted Rubber Particles]

The reacted rubber particles were collected as in Example 1, and re-suspended in an equal amount of 100 M Tris buffer (pH 7.5) containing 2 mM dithiothreitol (DTT).

[Measurement of Rubber Synthesis Activity of Reacted Rubber Particles]

The rubber synthesis activity of the collected reacted rubber particles was measured as in Example 1.

The results confirmed that a natural rubber was synthesized, and the collected reacted rubber particles had rubber synthesis activity.

[Measurement of Molecular Weight Distribution of Synthesized Very Long Chain Polyisoprenoid (Natural Rubber)]

The molecular weight distribution of the very long chain polyisoprenoid (natural rubber) synthesized in the above [Measurement of rubber synthesis activity of reacted rubber particles] was measured as in Example 1. FIG. 4(b) shows the results. FIG. 4(b) shows that the natural rubber synthesized in Reference Example 2 has a peak at substantially the same GPC elution time as the natural rubbers synthesized in Examples 1 to 3, indicating that the synthesized natural rubber has a comparable molecular weight distribution pattern.

These results strongly suggest that the natural rubber synthesized in Example 5 in which a NgBR family protein and REF were additionally bound to the rubber particles also has a comparable molecular weight distribution pattern.

Reference Example 3

[Preparation of Rubber Particles]

The same procedure as in Example 1 was followed.

[Cell-Free Protein Synthesis Reaction (Step 1: mRNA Transcription Reaction)]

Cell-free protein synthesis was performed using a WEPRO7240H expression kit (CellFree Sciences Co., Ltd.). An mRNA transcription reaction was performed using the vector pEU-His-N2-CPT3 obtained in [Preparation of vector for cell-free protein synthesis] in Example 6 as a template in accordance with the protocol of the WEPRO7240H expression kit.

[Purification of mRNA]

After the transcription reaction, the resulting mRNA was purified by ethanol precipitation.

[Cell-Free Protein Synthesis Reaction (Step 2: Protein Synthesis by Dialysis)]

The same procedure as in Example 1 was followed but using the above mRNA.

[Collection of Reacted Rubber Particles]

The reacted rubber particles were collected as in Example 1, and re-suspended in an equal amount of 100 M Tris buffer (pH 7.5) containing 2 mM dithiothreitol (DTT).

[Measurement of Rubber Synthesis Activity of Reacted Rubber Particles]

The rubber synthesis activity of the collected reacted rubber particles was measured as in Example 1.

The results confirmed that a natural rubber was synthesized, and the collected reacted rubber particles had rubber synthesis activity.

[Measurement of Molecular Weight Distribution of Synthesized Very Long Chain Polyisoprenoid (Natural Rubber)]

The molecular weight distribution of the very long chain polyisoprenoid (natural rubber) synthesized in the above [Measurement of rubber synthesis activity of reacted rubber particles] was measured as in Example 1. FIG. 4(b) shows the results. FIG. 4(b) shows that the natural rubber synthesized in Reference Example 3 has a peak at substantially the same GPC elution time as the natural rubbers synthesized in Examples 1 to 3, indicating that the synthesized natural rubber has a comparable molecular weight distribution pattern.

These results strongly suggest that the natural rubber synthesized in Example 6 in which a NgBR family protein and REF were additionally bound to the rubber particles also has a comparable molecular weight distribution pattern.

Reference Example 4

[Preparation of Rubber Particles]

The same procedure as in Example 1 was followed.

[Cell-Free Protein Synthesis Reaction (Step 1: mRNA Transcription Reaction)]

Cell-free protein synthesis was performed using a WEPRO7240H expression kit (CellFree Sciences Co., Ltd.). An mRNA transcription reaction was performed using the vector pEU-His-N2-CPT5 obtained in [Preparation of vector for cell-free protein synthesis] in Example 7 as a template in accordance with the protocol of the WEPRO7240H expression kit.

[Purification of mRNA]

After the transcription reaction, the resulting mRNA was purified by ethanol precipitation.

[Cell-Free Protein Synthesis Reaction (Step 2: Protein Synthesis by Dialysis)]

The same procedure as in Example 1 was followed but using the above mRNA.

[Collection of Reacted Rubber Particles]

The reacted rubber particles were collected as in Example 1, and re-suspended in an equal amount of 100 M Tris buffer (pH 7.5) containing 2 mM dithiothreitol (DTT).

[Measurement of Rubber Synthesis Activity of Reacted Rubber Particles]

The rubber synthesis activity of the collected reacted rubber particles was measured as in Example 1.

The results confirmed that a natural rubber was synthesized, and the collected reacted rubber particles had rubber synthesis activity.

[Measurement of Molecular Weight Distribution of Synthesized Very Long Chain Polyisoprenoid (Natural Rubber)]

The molecular weight distribution of the very long chain polyisoprenoid (natural rubber) synthesized in the above [Measurement of rubber synthesis activity of reacted rubber particles] was measured as in Example 1. FIG. 4(b) shows the results. FIG. 4(b) shows that the natural rubber synthesized in Reference Example 4 has a peak at substantially the same GPC elution time as the natural rubbers synthesized in Examples 1 to 3, indicating that the synthesized natural rubber has a comparable molecular weight distribution pattern.

These results strongly suggest that the natural rubber synthesized in Example 7 in which a NgBR family protein and REF were additionally bound to the rubber particles also has a comparable molecular weight distribution pattern.

Reference Example 5

[Synthesis of CPT Gene of *Homo sapiens*]

A CPT gene (HDS) of *Homo sapiens* was produced by synthesizing a region from the start codon to the stop codon using a gene synthesis service of GenScript Japan with public databases via BLAST. For cloning into a vector for cell-free protein synthesis described later, Xma I and Spe I sites were added to the 5' and 3' ends, respectively, of HDS.

A CPT gene (HDS) was produced as described above. The gene was sequenced to identify the full-length nucleotide sequence and amino acid sequence. The nucleotide sequence of HDS is given by SEQ ID NO:64. The amino acid sequence of HDS is given by SEQ ID NO:50.

[Vector Construction]

The obtained DNA fragment was inserted into pUC57 to prepare pUC57-HDS.

[Transformation of *Escherichia coli*]

The same procedure as in Example 1 was followed but using the prepared vector.

[Plasmid Extraction]

The same procedure as in Example 1 was followed.

[Preparation of Vector for Cell-Free Protein Synthesis]

The pUC57-HDS obtained in the above [Vector construction] was treated with the restriction enzymes Xma I and Spe I, and inserted into a pEU-E01-His-TEV-MCS-N2 cell-free expression vector that had been treated similarly with the restriction enzymes Xma I and Spe I to prepare pEU-His-N2-HDS.

[Transformation of *Escherichia coli*]

The same procedure as in Example 1 was followed but using the prepared vector.

[Plasmid Extraction] The same procedure as in Example 1 was followed.

[Preparation of Rubber Particles]

The same procedure as in Example 1 was followed.

[Cell-Free Protein Synthesis Reaction (Step 1: mRNA Transcription Reaction)]

Cell-free protein synthesis was performed using a WEPRO7240H expression kit (CellFree Sciences Co., Ltd.). An mRNA transcription reaction was performed using the vector obtained in the above [Preparation of vector for cell-free protein synthesis] as a template in accordance with the protocol of the WEPRO7240H expression kit.

[Purification of mRNA]

After the transcription reaction, the resulting mRNA was purified by ethanol precipitation.

[Cell-Free Protein Synthesis Reaction (Step 2: Protein Synthesis by Dialysis)]

The same procedure as in Example 1 was followed but using the above mRNA.

[Collection of Reacted Rubber Particles]

The reacted rubber particles were collected as in Example 1, and re-suspended in an equal amount of 100 M Tris buffer (pH 7.5) containing 2 mM dithiothreitol (DTT).

[Measurement of Rubber Synthesis Activity of Reacted Rubber Particles]

The rubber synthesis activity of the collected reacted rubber particles was measured as in Example 1, except that the reaction time was changed from 16 hours to 4 hours. The results confirmed that a natural rubber was synthesized, and the collected reacted rubber particles had rubber synthesis activity.

[Measurement of Molecular Weight Distribution of Synthesized Very Long Chain Polyisoprenoid (Natural Rubber)]

The molecular weight distribution of the very long chain polyisoprenoid (natural rubber) synthesized in the above [Measurement of rubber synthesis activity of reacted rubber particles] was measured as in Example 1. FIG. 4(c) shows the results. FIG. 4(c) shows that the natural rubber synthesized in Reference Example 5 has a peak at substantially the same GPC elution time as the natural rubbers synthesized in Examples 1 to 3, indicating that the synthesized natural rubber has a comparable molecular weight distribution pattern.

These results strongly suggest that, by additionally binding a NgBR family protein to the rubber particles so that both HDS protein and the NgBR family protein are bound to the rubber particles, the activity of HDS protein on the rubber particles is stabilized and increased, thereby increasing the rubber synthesis activity of the rubber particles.

Reference Example 6

[Synthesis of CPT Gene of Yeast (*Saccharomyces cerevisiae*)]

A CPT gene (SRT1) of a yeast (*Saccharomyces cerevisiae*) was produced by synthesizing a region from the start codon to the stop codon using a gene synthesis service of GenScript Japan with public databases via BLAST. For cloning into a vector for cell-free protein synthesis described later, Xma I and Spe I sites were added to the 5' and 3' ends, respectively, of SRT1.

A CPT gene (SRT1) was produced as described above. The gene was sequenced to identify the full-length nucleotide sequence and amino acid sequence. The nucleotide sequence of SRT1 is given by SEQ ID NO:63. The amino acid sequence of SRT1 is given by SEQ ID NO:47.

[Vector Construction]

The obtained DNA fragment was inserted into pUC57 to prepare pUC57-SRT1.

[Transformation of *Escherichia coli*]

The same procedure as in Example 1 was followed but using the prepared vector.

[Plasmid Extraction]

The same procedure as in Example 1 was followed.

[Preparation of Vector for Cell-Free Protein Synthesis]

The pUC57-SRT1 obtained in the above [Vector construction] was treated with the restriction enzymes Xma I and Spe I, and inserted into a pEU-E01-His-TEV-MCS-N2 cell-free expression vector that had been treated similarly with the restriction enzymes Xma I and Spe I to prepare pEU-His-N2-SRT1.

[Transformation of *Escherichia coli*]

The same procedure as in Example 1 was followed but using the prepared vector.

[Plasmid Extraction]

The same procedure as in Example 1 was followed.

[Preparation of Rubber Particles]

The same procedure as in Example 1 was followed.

[Cell-Free Protein Synthesis Reaction (Step 1: mRNA Transcription Reaction)]

Cell-free protein synthesis was performed using a WEPRO7240H expression kit (CellFree Sciences Co., Ltd.). An mRNA transcription reaction was performed using the vector obtained in the above [Preparation of vector for cell-free protein synthesis] as a template in accordance with the protocol of the WEPRO7240H expression kit.

[Purification of mRNA]

After the transcription reaction, the resulting mRNA was purified by ethanol precipitation.

[Cell-Free Protein Synthesis Reaction (Step 2: Protein Synthesis by Dialysis)]

The same procedure as in Example 1 was followed but using the above mRNA.

[Collection of Reacted Rubber Particles]

The reacted rubber particles were collected as in Example 1, and re-suspended in an equal amount of 100 M Tris buffer (pH 7.5) containing 2 mM dithiothreitol (DTT).

[Measurement of Rubber Synthesis Activity of Reacted Rubber Particles]

The rubber synthesis activity of the collected reacted rubber particles was measured as in Example 1, except that the reaction time was changed from 16 hours to 4 hours. The results confirmed that a natural rubber was synthesized, and the collected reacted rubber particles had rubber synthesis activity.

[Measurement of Molecular Weight Distribution of Synthesized Very Long Chain Polyisoprenoid (Natural Rubber)]

The molecular weight distribution of the very long chain polyisoprenoid (natural rubber) synthesized in the above [Measurement of rubber synthesis activity of reacted rubber particles] was measured as in Example 1. FIG. 4(c) shows the results. FIG. 4(c) shows that the natural rubber synthesized in Reference Example 6 has a peak at substantially the same GPC elution time as the natural rubbers synthesized in Examples 1 to 3, indicating that the synthesized natural rubber has a comparable molecular weight distribution pattern.

These results strongly suggest that, by additionally binding a NgBR family protein to the rubber particles so that both SRT1 protein and the NgBR family protein are bound to the rubber particles, the activity of SRT1 protein on the rubber particles is stabilized and increased, thereby increasing the rubber synthesis activity of the rubber particles.

<Rubber Synthesis Activity of CPT Family Protein Introduced into Yeast>

Reference Example 7

[Acquisition of Gene for Yeast Expression]

PCR was performed using the pGEM-HRT1 and pGEM-HRT2 prepared in Examples 1 and 5 as templates and the primers described below to produce HRT1 and HRT2 genes containing a Bam HI restriction enzyme site at both the 5' and 3' ends for cloning into a pJR1133 yeast expression vector.

The following primers were used for HRT1 and HRT2.

```
Primer 17:
5'-ttaggatccatggaattatacaacgg-3'

Primer 18:
5'-aacggatcctttaagtattccttatg-3'
```

Moreover, the pBS-AtCPT8 obtained in Example 3 was treated with the restriction enzyme Bam HI to produce a AtCPT8 gene containing a Bam HI restriction enzyme site at both the 5' and 3' ends.

Moreover, PCR was performed using the pGEM-HRTBP and pBS-AtLEW1 prepared in Examples 1 and 3 as templates and the primers described below to produce a HRTBP gene containing a Xho I restriction enzyme site at both the 5' and 3' ends and a AtLEW1 gene containing a Sal I restriction enzyme site at the 5'end and a Bam HI restriction enzyme site at the 3' end for cloning into pGK415 and pGK425 yeast expression vectors, respectively. PCR was carried out using a KOD-plus-Neo (Toyobo Co., Ltd.) in accordance with the manual. The PCR reaction involved 35 cycles with each cycle consisting of 10 seconds at 98° C., 30 seconds at 58° C., and 1 minute at 68° C.

The following primers were used for HRTBP.

```
Primer 19:
5'-tttctcgagatggatttgaaacctggagctg-3'

Primer 20:
5'-tttctcgagtcatgtaccataattttgctgcac-3'
```

The following primers were used for AtLEW1.

```
Primer 21:
5'-gtcgacatggattcgaatcaatcg-3'

Primer 22:
5'-ggatccttaagttccatagtttggg-3'
```

[Vector Construction]

The obtained DNA fragments were subjected to dA addition and then inserted into pGEM-T Easy vectors using a pGEM-T Easy Vector System (Promega) to prepare pGEM-HRT1 (for pJR1133), pGEM-HRT2 (for pJR1133), pGEM-AtCPT8 (for pJR1133), pGEM-HRTBP (for pGK425), and pGEM-AtLEW1 (for pGK425).

[Transformation of *Escherichia coli*]

The same procedure as in Example 1 was followed but using the prepared vectors.

[Plasmid Extraction]

The same procedure as in Example 1 was followed.

[Preparation of Yeast Expression Vectors]

The pGEM-CPT series obtained in the above [Vector construction] were treated with the restriction enzyme Bam HI, and inserted into a pJR1133 yeast expression vector that had been treated similarly with the restriction enzyme Bam HI to prepare pJR1133-HRT1, pJR1133-HRT2, and pJR1133-AtCPT8.

Also, the pGEM-NgBR series obtained in the above [Vector construction] were treated with the restriction enzyme Xho I, and inserted into a pGK425 yeast expression vector that had been treated similarly with the restriction enzyme Sal I to prepare pGK425-HRTBP and pGK425-AtLEW1.

[Transformation of *Escherichia coli*]

*Escherichia coli* DH5α was transformed with the prepared vectors, and each transformant was cultured on LB medium containing ampicillin.

[Plasmid Extraction]

The same procedure as in Example 1 was followed.

[Transformation of Yeast]

The yeast SNH23-7D (MAT-α rer2-2 mf-1::ADE2 mf-2:: TRP1 bar1::HIS3 ade2 trp1 his3 leu2 ura3 lys2) was transformed with the following combinations of the prepared plasmids.

(1) pJR1133-HRT1 & pGK425-HRTBP
(2) pJR1133-HRT2 & pGK425-HRTBP
(3) pJR1133-AtCPT & pGK425-AtLEW1

The transformed yeasts were cultured on uracil (for pJR1133 selection) and leucine-free (for pGK425 selection) SD agar medium to produce transformants.

[Expression of Enzyme]

Each transformed yeast obtained above was added to 50 mL of SC (+Lys) medium, followed by shaking culture at 23° C. and 180 rpm. Upon reaching $OD_{546}$=0.8, 45 mL of the cell culture was collected in a 50 mL sampling tube and centrifuged at 5,000×g for 10 minutes. After removing the supernatant, the residue was cryopreserved at −80° C.

The composition of the SC (+Lys) medium was as follows.

Ammonium sulfate: 5.0 g
Yeast nitrogen base w/o amino acids: 1.7 g
Lysine HCl: 30 mg
Glucose: 20 g
Sterilized water: up to 1 L

[Preparation of Crude Enzyme Solution]

Each cryopreserved sample was melted on ice, suspended in 100 μL of zymolyase buffer, and left at 23° C. for 15 minutes. The mixture was centrifuged to remove the supernatant. Thereto was added 300 μL of zymolyase buffer with 2 mg/mL of zymolyase 100T, followed by an enzymatic reaction at 30° C. for 40 minutes to convert the cells into spheroplasts. The mixture was centrifuged to remove the supernatant, and suspended in 300 μL of zymolyase buffer. The mixture was centrifuged to remove the supernatant, and the cells were suspended in breakage buffer and then subjected to three cycles of 30-second vortex mixing and then 30-seconds cooling on ice using 0.5 mm glass beads to disrupt the cells. The mixture was centrifuged at 300×g for five minutes to remove undisrupted cells. The supernatant collected was centrifuged at 17,400×g to separate the supernatant and pellets. The pellets were suspended in breakage buffer. The suspension was used as a crude enzyme solution which is an insoluble fraction. The compositions of the zymolyase buffer and breakage buffer are described below.

Zymolyase Buffer:

| Tris-HCl (pH 7.5) | 50 mM |
| MgCl₂ | 10 mM |
| Sorbitol | 1M |
| DTT | 1x |

Breakage Buffer:

| Tris-HCl (pH 8.0) | 100 mM |
| NaCl | 150 mM |
| DTT | 1 mM |
| Protease inhibitor cocktail (Nacalai Tesque Inc.) | 1x |

[Measurement of Rubber Synthesis Activity (Analysis of Reaction Product by Reversed-Phase TLC (Polyprenyl Diphosphate))]

The rubber synthesis activity in each of the collected crude enzyme solutions was measured as follows.

First, 25 mM potassium phosphate buffer (pH 7.5), 25 mM β-mercaptoethanol, 20 mM KF, 4 mM MgCl₂, 10 μM farnesyl diphosphate (FPP), 50 μM 1-14C isopentenyl diphosphate ([1-14C] IPP, specific activity 60 Ci/mol), and 50 μg of the crude enzyme solution were mixed to prepare a reaction solution (100 μL in total), which was then reacted for 20 hours at 30° C.

The reaction was stopped by addition of 200 μL of saturated saline. The reaction solution was mixed with 1 mL of diethyl ether and vortexed. The mixture was centrifuged at 15,000 rpm for one minute, and the upper phase (ether phase) was collected in a separate tube. To the aqueous phase was added 1 mL of water-saturated butanol. The mixture was stirred and subsequently centrifuged at 15,000 rpm for one minute to collect the upper phase (butanol phase), whereby an enzymatic reaction product was extracted.

The butanol phase was washed with water. Subsequently, the solvent was removed using a centrifugal evaporator to concentrate the reaction product. The concentrated reaction product was dephosphorylated by a reaction with the following composition at 37° C. for 12 hours to obtain a corresponding polyprenol.

Reaction composition (Total 100 mL):

| Acetate buffer (pH 5.6) | 40 mM |
| Triton X-100 | 0.1% (v/v) |
| Methanol | 40% (v/v) |
| Butanol phase (reaction product) | 20% (v/v) |
| Potato acid phosphatase (Roche) | 10 U |

By addition of 120 μL of 5 M NaOH, the reaction was stopped, and simultaneously hydrolysis was performed at 37° C. for 30 minutes. To the reaction solution was added 0.7 mL of pentane, and the mixture was stirred to extract the polyprenol into the pentane phase. Centrifugation was performed at 15,000 rpm for one minute to collect the upper phase (pentane phase). The product was developed using a reversed-phase TLC plate (LKC-18, Whatman). The developing solvent used was a mixture of acetone and water (acetone:water=39:1). The origin and the solvent front were marked with an ink containing a 14C-labeled radioactive substance to perform autoradiography using a Typhoon FLA 7000 (GE Healthcare Japan Corporation). The chain length of the product was analyzed by comparing the position of the spot of the radioactive reaction product with that of a reference material.

The results confirmed that isoprene polymers with about 90 carbon atoms were synthesized in all the cases where any of the plasmids (1) to (3) was used.

<Rubber Synthesis Activity of CPT Family Protein Introduced into *Escherichia coli*>

Reference Example 8

[Transformation of *Escherichia coli*]

The pGEM-HRT1, pBS-AtCPT8, and pGEM-HRT2 obtained in Examples 1, 3, and 5, respectively, and pGEM-HRTBP and pBS-AtLEW1 obtained in Examples 1 and 3, respectively, were used. These genes were each inserted into a pCOLADuet1 vector. *Escherichia coli* BL21 (DE3) was transformed with the vectors with the following combinations.

(1) HRT1-HRTBP
(2) HRT2-HRTBP
(3) AtCPT8-AtLEW1

[Measurement of Rubber Synthesis Activity in *Escherichia coli*]

The rubber synthesis activity was measured as in Reference Example 7 but using the *Escherichia coli* transformed in the above [Transformation of *Escherichia coli*]. The results show that the reaction product was too little to be detectable in all the cases where any of the plasmids (1) to (3) was used.

In the case where a CPT family protein (HRT1, HRT2, AtCPT8) derived from *Hevea brasiliensis* or *Arabidopsis thaliana* was introduced into *Escherichia coli* as in Reference Examples 7 and 8, the reaction product was not detected. Next, in the case where the CPT family protein was introduced into a yeast, the synthesis of an isoprene polymer having a chain length of about 90 carbon atoms was confirmed.

In contrast, in the case where any one of the CPT family proteins was bound to rubber particles as in Examples 1 to 7 and Reference Examples 1, 5, and 6, the rubber synthesis activity measurements confirmed the synthesis of a very long chain polyisoprenoid (natural rubber). In other words, natural rubber could be synthesized not only by binding to rubber particles a CPT family protein (HRT1, HRT2, CPT3, OPTS, LsCPT3, TbCPT1) derived from a rubber-producing plant and considered to be expressed in laticifers, but also by binding AtCPT8 from *Arabidopsis thaliana* which is not a rubber-producing plant, SRT1 derived from yeast, or HDS derived from human.

These results suggest that the host into which the gene is introduced, or in other words the environment in which the CPT family protein is expressed is more important for the rubber synthesis activity than the origin or type of the CPT family protein.

Based on the above, the present inventors assume the following mechanism.

That is, they suppose that the chain length of a product to be synthesized by a CPT family protein depends on the hydrophobicity and space of the site where the synthesized product accumulates.

Specifically, in prokaryotes such as *Escherichia coli*, the CPT family proteins show an activity that produces no detectable reaction product, or even if they show activity to synthesize products, the products have chains extended only to a length receivable within the hydrophobic cleft structures of the CPT family proteins.

In eukaryotes such as yeasts, the products synthesized by the CPT family proteins transfer from the hydrophobic cleft structures of the CPT family proteins into the lipid bilayers of cells, for example into the endoplasmic reticulum lumen, and accumulate in the lipid bilayers whose environment is hydrophobic but whose space is not very large, and therefore the products have limited chain lengths (the aforementioned isoprene polymer having a chain length of about 90 carbon atoms seems to be synthesized in this manner).

Also in non rubber-producing plants such as *Arabidopsis thaliana*, similarly as in yeasts, the products synthesized by the CPT family proteins accumulate in the lipid bilayers of cells whose space is not very large, and it is thus considered that the synthesized products also have limited chain lengths.

In contrast, when a CPT family protein is bound to rubber particles, a product synthesized by the CPT family protein accumulates in the rubber particles whose environment is hydrophobic and whose space is much larger than that in the lipid bilayers of cells, as illustrated in FIG. 1. Thus, the chain length of the product is sufficiently extended in such a hydrophobic environment with few spatial restrictions, so that a very long chain polyisoprenoid (natural rubber) can be synthesized.

Therefore, it is strongly suggested that by binding any CPT family protein, regardless of the origin, type, and other factors of the protein, together with a NgBR family protein to rubber particles, it is possible to increase the rubber synthesis activity of the rubber particles, thereby achieving the effects of the present invention.

<In Silico Estimation of Conserved Regions of CPT Family Proteins>

Multiple sequence alignment of the CPT family proteins derived from various organisms shown in FIG. 5 was performed to search highly conserved sequences (conserved regions). FIG. 5 shows the alignment results around the conserved regions.

The multiple sequence alignment was carried out using software called Genetyx Ver. 11.

In FIG. 5, UDP pyrophosphate synthase (*Escherichia coli* CPT) corresponds to an alignment of positions 7 to 125 of undecaprenyl pyrophosphate synthase (UPPS) from *Escherichia coli* represented by SEQ ID NO:45; UDP (*Micrococcus luteus* B-P 26 CPT) corresponds to an alignment of positions 11 to 129 of undecaprenyl diphosphate synthase (UPS) from *Micrococcus* represented by SEQ ID NO:46;

SRT1 (Yeast CPT) corresponds to an alignment of positions 57 to 175 of SRT1 from yeast represented by SEQ ID NO:47;

AtCPT5 (*Arabidopsis thaliana* CPT5) corresponds to an alignment of positions 61 to 179 of AtCPT5 from *Arabidopsis thaliana* represented by SEQ ID NO:44;

AtCPT8 (*Arabidopsis thaliana* CPT8) corresponds to an alignment of positions 25 to 142 of AtCPT8 from *Arabidopsis thaliana* represented by SEQ ID NO:22;

DDPS (*Nicotiana sylvestris* CPT) corresponds to an alignment of positions 24 to 140 of DDPS from tobacco represented by SEQ ID NO: 48;

HbCPT1 (*Hevea brasiliensis* CPT) corresponds to an alignment of positions 23 to 139 of HRT1 from *Hevea brasiliensis* represented by SEQ ID NO:2;

HbCPT2 (*Hevea brasiliensis* CPT) corresponds to an alignment of positions 23 to 139 of HRT2 from *Hevea brasiliensis* represented by SEQ ID NO: 32;

HbCPT3 (*Hevea brasiliensis* CPT) corresponds to an alignment of positions 23 to 139 of CPT3 from *Hevea brasiliensis* represented by SEQ ID NO:36;

HbCPT4 (*Hevea brasiliensis* CPT) corresponds to an alignment of positions 24 to 140 of CPT4 from *Hevea brasiliensis* represented by SEQ ID NO:37;

HbCPT5 (*Hevea brasiliensis* CPT) corresponds to an alignment of positions 23 to 139 of CPT5 from *Hevea brasiliensis* represented by SEQ ID NO: 41;

LsCPT3 (*Lactuca sativa* CPT) corresponds to an alignment of positions 40 to 156 of LsCPT3 from *Lactuca sativa* represented by SEQ ID NO:14;

TbCPT1 (*Taraxacum brevicorniculatum* CPT) corresponds to an alignment of positions 40 to 154 of TbCPT1 from *Taraxacum brevicorniculatum* represented by SEQ ID NO:43;

DDPS (Mouse CPT) corresponds to an alignment of positions 16 to 132 of DDPS from mouse represented by SEQ ID NO:49; and HDS (Human CPT) corresponds to an alignment of positions 16 to 132 of HDS from human represented by SEQ ID NO:50.

According to literatures such as Shota Endo et. al., Biochimica et Biophysica Acta, No. 1625 (2003), pp. 291-295 and Masahiro Fujihashi et. al., PNAS, Vol. 98, No. 8 (2001), pp. 4337-4342, box A (corresponding to positions 41 to 49 of HRT1 from *Hevea brasiliensis* represented by SEQ ID NO:2) and box B (corresponding to positions 81 to 97 of HRT1 from *Hevea brasiliensis* represented by SEQ ID NO:2) in FIG. 5 are parts of highly conserved regions of CPT family proteins derived from various organisms. In particular, it is considered that an aspartic acid residue conserved at a position corresponding to position 41 of HRT1 from *Hevea brasiliensis* represented by SEQ ID NO:2 ((1) in FIG. 5), a glycine residue conserved at a position corresponding to position 42 of HRT1 from *Hevea brasiliensis* represented by SEQ ID NO:2 ((2) in FIG. 5), an arginine residue conserved at a position corresponding to position 45 of HRT1 from *Hevea brasiliensis* represented by SEQ ID NO:2 ((3) in FIG. 5), and an asparagine residue conserved at a position corresponding to position 89 of HRT1 from *Hevea brasiliensis* ((4) in FIG. 5) are essential amino acids for the enzymatic reactions of CPT family proteins, so that proteins having these amino acids at the respective positions have the functions of CPT family proteins.

The following is understood from FIG. 5.

The conserved region in box A corresponding to positions 41 to 49 in the amino acid sequence of HRT1 from *Hevea brasiliensis* represented by SEQ ID NO:2 corresponds to:

positions 25 to 33 for undecaprenyl pyrophosphate synthase (UPPS) from *Escherichia coli* represented by SEQ ID NO: 45;

positions 29 to 37 for undecaprenyl diphosphate synthase (UPS) from *Micrococcus* represented by SEQ ID NO:46;

positions 75 to 83 for SRT1 from yeast represented by SEQ ID NO:47;

positions 79 to 87 for AtCPT5 from *Arabidopsis thaliana* represented by SEQ ID NO:44;

positions 43 to 51 for AtCPT8 from *Arabidopsis thaliana* represented by SEQ ID NO:22;

positions 42 to 50 for DDPS from tobacco represented by SEQ ID NO:48;

positions 41 to 49 for HRT2 from *Hevea brasiliensis* represented by SEQ ID NO:32;

positions 41 to 49 for CPT3 from *Hevea brasiliensis* represented by SEQ ID NO:36;

positions 42 to 50 for CPT4 from *Hevea brasiliensis* represented by SEQ ID NO:37;

positions 41 to 49 for OPTS from *Hevea brasiliensis* represented by SEQ ID NO:41;

positions 58 to 66 for LsCPT3 from *Lactuca sativa* represented by SEQ ID NO:14;

positions 58 to 66 for TbCPT1 from *Taraxacum brevicorniculatum* represented by SEQ ID NO:43;

positions 34 to 42 for DDPS from mouse represented by SEQ ID NO:49; and positions 34 to 42 for HDS from human represented by SEQ ID NO:50.

The conserved region in box B corresponding to positions 81 to 97 in the amino acid sequence of HRT1 from *Hevea brasiliensis* represented by SEQ ID NO:2 corresponds to:

positions 65 to 81 for undecaprenyl pyrophosphate synthase (UPPS) from *Escherichia coli* represented by SEQ ID NO:45;

positions 69 to 85 for undecaprenyl diphosphate synthase (UPS) from *Micrococcus* represented by SEQ ID NO:46;

positions 115 to 131 for SRT1 from yeast represented by SEQ ID NO:47;

positions 119 to 135 for AtCPT5 from *Arabidopsis thaliana* represented by SEQ ID NO:44;

positions 84 to 100 for AtCPT8 from *Arabidopsis thaliana* represented by SEQ ID NO:22;

positions 82 to 98 for DDPS from tobacco represented by SEQ ID NO:48;

positions 81 to 97 for HRT2 from *Hevea brasiliensis* represented by SEQ ID NO:32;

positions 81 to 97 for CPT3 from *Hevea brasiliensis* represented by SEQ ID NO:36;

positions 82 to 98 for CPT4 from *Hevea brasiliensis* represented by SEQ ID NO:37;

positions 81 to 97 for CPT5 from *Hevea brasiliensis* represented by SEQ ID NO:41;

positions 98 to 114 for LsCPT3 from *Lactuca sativa* represented by SEQ ID NO:14;

positions 98 to 114 for TbCPT1 from *Taraxacum brevicorniculatum* represented by SEQ ID NO:43;

positions 74 to 90 for DDPS from mouse represented by SEQ ID NO:49; and positions 74 to 90 for HDS from human represented by SEQ ID NO:50.

The aspartic acid residue (1) corresponding to position 41 in the amino acid sequence of HRT1 from *Hevea brasiliensis* represented by SEQ ID NO:2 corresponds to:

an aspartic acid residue at position 25 for undecaprenyl pyrophosphate synthase (UPPS) from *Escherichia coli* represented by SEQ ID NO:45;

an aspartic acid residue at position 29 for undecaprenyl diphosphate synthase (UPS) from *Micrococcus* represented by SEQ ID NO:46;

an aspartic acid residue at position 75 for SRT1 from yeast represented by SEQ ID NO:47;

an aspartic acid residue at position 79 for AtCPT5 from *Arabidopsis thaliana* represented by SEQ ID NO:44;

an aspartic acid residue at position 43 for AtCPT8 from *Arabidopsis thaliana* represented by SEQ ID NO:22;

an aspartic acid residue at position 42 for DDPS from tobacco represented by SEQ ID NO:48;

an aspartic acid residue at position 41 for HRT2 from *Hevea brasiliensis* represented by SEQ ID NO:32;

an aspartic acid residue at position 41 for CPT3 from *Hevea brasiliensis* represented by SEQ ID NO:36;

an aspartic acid residue at position 42 for CPT4 from *Hevea brasiliensis* represented by SEQ ID NO:37;

an aspartic acid residue at position 41 for CPT5 from *Hevea brasiliensis* represented by SEQ ID NO:41;

an aspartic acid residue at position 58 for LsCPT3 from *Lactuca sativa* represented by SEQ ID NO:14;

an aspartic acid residue at position 58 for TbCPT1 from *Taraxacum brevicorniculatum* represented by SEQ ID NO:43;

an aspartic acid residue at position 34 for DDPS from mouse represented by SEQ ID NO:49; and an aspartic acid residue at position 34 for HDS from human represented by SEQ ID NO:50.

The glycine residue (2) corresponding to position 42 in the amino acid sequence of HRT1 from *Hevea brasiliensis* represented by SEQ ID NO:2 corresponds to:

a glycine residue at position 26 for undecaprenyl pyrophosphate synthase (UPPS) from *Escherichia coli* represented by SEQ ID NO:45;

a glycine residue at position 30 for undecaprenyl diphosphate synthase (UPS) from *Micrococcus* represented by SEQ ID NO:46;

a glycine residue at position 76 for SRT1 from yeast represented by SEQ ID NO:47;

a glycine residue at position 80 for AtCPT5 from *Arabidopsis thaliana* represented by SEQ ID NO:44;

a glycine residue at position 44 for AtCPT8 from *Arabidopsis thaliana* represented by SEQ ID NO:22;

a glycine residue at position 43 for DDPS from tobacco represented by SEQ ID NO:48;

a glycine residue at position 42 for HRT2 from *Hevea brasiliensis* represented by SEQ ID NO:32;

a glycine residue at position 42 for CPT3 from *Hevea brasiliensis* represented by SEQ ID NO:36;

a glycine residue at position 43 for CPT4 from *Hevea brasiliensis* represented by SEQ ID NO:37;

a glycine residue at position 42 for CPTS from *Hevea brasiliensis* represented by SEQ ID NO:41;

a glycine residue at position 59 for LsCPT3 from *Lactuca sativa* represented by SEQ ID NO:14;

a glycine residue at position 59 for TbCPT1 from *Taraxacum brevicorniculatum* represented by SEQ ID NO:43;

a glycine residue at position 35 for DDPS from mouse represented by SEQ ID NO:49; and a glycine residue at position 35 for HDS from human represented by SEQ ID NO:50.

The arginine residue (3) corresponding to position 45 in the amino acid sequence of HRT1 from *Hevea brasiliensis* represented by SEQ ID NO:2 corresponds to:

an arginine residue at position 29 for undecaprenyl pyrophosphate synthase (UPPS) from *Escherichia coli* represented by SEQ ID NO:45;

an arginine residue at position 33 for undecaprenyl diphosphate synthase (UPS) from *Micrococcus* represented by SEQ ID NO:46;

an arginine residue at position 79 for SRT1 from yeast represented by SEQ ID NO:47;

an arginine residue at position 83 for AtCPT5 from *Arabidopsis thaliana* represented by SEQ ID NO:44;

an arginine residue at position 47 for AtCPT8 from *Arabidopsis thaliana* represented by SEQ ID NO:22;

an arginine residue at position 46 for DDPS from tobacco represented by SEQ ID NO:48;

an arginine residue at position 45 for HRT2 from *Hevea brasiliensis* represented by SEQ ID NO:32;

an arginine residue at position 45 for CPT3 from *Hevea brasiliensis* represented by SEQ ID NO:36;

an arginine residue at position 46 for CPT4 from *Hevea brasiliensis* represented by SEQ ID NO:37;

an arginine residue at position 45 for OPTS from *Hevea brasiliensis* represented by SEQ ID NO:41;

an arginine residue at position 62 for LsCPT3 from *Lactuca sativa* represented by SEQ ID NO:14;

an arginine residue at position 62 for TbCPT1 from *Taraxacum brevicorniculatum* represented by SEQ ID NO:43;

an arginine residue at position 38 for DDPS from mouse represented by SEQ ID NO:49; and an arginine residue at position 38 for HDS from human represented by SEQ ID NO:50.

The asparagine residue (4) corresponding to position 89 in the amino acid sequence of HRT1 from *Hevea brasiliensis* represented by SEQ ID NO:2 corresponds to:

an asparagine residue at position 73 for undecaprenyl pyrophosphate synthase (UPPS) from *Escherichia coli* represented by SEQ ID NO:45;

an asparagine residue at position 77 for undecaprenyl diphosphate synthase (UPS) from *Micrococcus* represented by SEQ ID NO:46;

an asparagine residue at position 123 for SRT1 from yeast represented by SEQ ID NO:47;

an asparagine residue at position 127 for AtCPT5 from *Arabidopsis thaliana* represented by SEQ ID NO:44;

an asparagine residue at position 92 for AtCPT8 from *Arabidopsis thaliana* represented by SEQ ID NO:22;

an asparagine residue at position 90 for DDPS from tobacco represented by SEQ ID NO:48;

an asparagine residue at position 89 for HRT2 from *Hevea brasiliensis* represented by SEQ ID NO:32;

an asparagine residue at position 89 for CPT3 from *Hevea brasiliensis* represented by SEQ ID NO:36;

an asparagine residue at position 90 for CPT4 from *Hevea brasiliensis* represented by SEQ ID NO:37;

an asparagine residue at position 89 for CPT5 from *Hevea brasiliensis* represented by SEQ ID NO:41;

an asparagine residue at position 106 for LsCPT3 from *Lactuca sativa* represented by SEQ ID NO:14;

an asparagine residue at position 106 for TbCPT1 from *Taraxacum brevicorniculatum* represented by SEQ ID NO:43;

an asparagine residue at position 82 for DDPS from mouse represented by SEQ ID NO:49; and an asparagine residue at position 82 for HDS from human represented by SEQ ID NO:50.

SEQUENCE LISTING FREE TEXT

SEQ ID NO:1: Nucleotide sequence of gene coding for HRT1 from *Hevea brasiliensis*

SEQ ID NO: 2: Amino acid sequence of HRT1 from *Hevea brasiliensis*

SEQ ID NO:3: Nucleotide sequence of gene coding for HRTBP from *Hevea brasiliensis*

SEQ ID NO:4: Amino acid sequence of HRTBP from *Hevea brasiliensis*

SEQ ID NO:5: Primer 1
SEQ ID NO:6: Primer 2
SEQ ID NO:7: Primer 3
SEQ ID NO:8: Primer 4

SEQ ID NO: 9: Nucleotide sequence of promoter of gene coding for rubber elongation factor from *Hevea brasiliensis*

SEQ ID NO:10: Nucleotide sequence of promoter of gene coding for small rubber particle protein from *Hevea brasiliensis*

SEQ ID NO:11: Nucleotide sequence of promoter of gene coding for Hevien 2.1 from *Hevea brasiliensis*

SEQ ID NO:12: Nucleotide sequence of promoter of gene coding for MYC1 transcription factor from *Hevea brasiliensis*

SEQ ID NO: 13: Nucleotide sequence of gene coding for LsCPT3 from *Lactuca sativa*

SEQ ID NO: 14: Amino acid sequence of LsCPT3 from *Lactuca sativa*

SEQ ID NO:15: Nucleotide sequence of gene coding for LsCPTL2 from *Lactuca sativa*

SEQ ID NO:16: Amino acid sequence of LsCPTL2 from *Lactuca sativa*

SEQ ID NO:17: Primer 5
SEQ ID NO:18: Primer 6
SEQ ID NO:19: Primer 7
SEQ ID NO:20: Primer 8

SEQ ID NO:21: Nucleotide sequence of gene coding for AtCPT8 from *Arabidopsis thaliana*

SEQ ID NO:22: Amino acid sequence of AtCPT8 from *Arabidopsis thaliana*

SEQ ID NO: 23: Nucleotide sequence of gene coding for AtLEW1 from *Arabidopsis thaliana*

SEQ ID NO:24: Amino acid sequence of AtLEW1 from *Arabidopsis thaliana*

SEQ ID NO:25: Primer 9
SEQ ID NO:26: Primer 10

SEQ ID NO:27: Nucleotide sequence of gene coding for REF from *Hevea brasiliensis*

SEQ ID NO:28: Amino acid sequence of REF from *Hevea brasiliensis*

SEQ ID NO:29: Primer 11
SEQ ID NO:30: Primer 12

SEQ ID NO:31: Nucleotide sequence of gene coding for HRT2 from *Hevea brasiliensis*

SEQ ID NO:32: Amino acid sequence of HRT2 from *Hevea brasiliensis*

SEQ ID NO:33: Primer 13
SEQ ID NO:34: Primer 14

SEQ ID NO:35: Nucleotide sequence of gene coding for CPT3 from *Hevea brasiliensis*

SEQ ID NO:36: Amino acid sequence of CPT3 from *Hevea brasiliensis*

SEQ ID NO:37: Amino acid sequence of CPT4 from *Hevea brasiliensis*

SEQ ID NO:38: Primer 15
SEQ ID NO:39: Primer 16

SEQ ID NO:40: Nucleotide sequence of gene coding for CPT5 from *Hevea brasiliensis*

SEQ ID NO:41: Amino acid sequence of CPT5 from *Hevea brasiliensis*

SEQ ID NO: 42: Nucleotide sequence of gene coding for TbCPT1 from *Taraxacum brevicorniculatum*
SEQ ID NO:43: Amino acid sequence of TbCPT1 from *Taraxacum brevicorniculatum*
SEQ ID NO:44: Amino acid sequence of AtCPT5 from *Arabidopsis thaliana*
SEQ ID NO: 45: Amino acid sequence of undecaprenyl pyrophosphate synthase (UPPS) from *Escherichia coli*
SEQ ID NO:46: Amino acid sequence of undecaprenyl diphosphate synthase (UPS) from *Micrococcus*
SEQ ID NO:47: Amino acid sequence of SRT1 from yeast
SEQ ID NO:48: Amino acid sequence of DDPS from tobacco
SEQ ID NO:49: Amino acid sequence of DDPS from mouse
SEQ ID NO:50: Amino acid sequence of HDS from human
SEQ ID NO:51: Amino acid sequence at positions 41 to 49 of HRT1 from *Hevea brasiliensis*
SEQ ID NO:52: Amino acid sequence at positions 81 to 97 of HRT1 from *Hevea brasiliensis*
SEQ ID NO:53: Primer 17
SEQ ID NO:54: Primer 18
SEQ ID NO:55: Primer 19
SEQ ID NO:56: Primer 20
SEQ ID NO:57: Primer 21
SEQ ID NO:58: Primer 22
SEQ ID NO:59: Primer 23
SEQ ID NO:60: Primer 24
SEQ ID NO:61: Primer 25
SEQ ID NO:62: Primer 26
SEQ ID NO:63: Nucleotide sequence of gene coding for SRT1 from yeast
SEQ ID NO:64: Nucleotide sequence of gene coding for HDS from human

The invention claimed is:

1. A method for producing a polyisoprenoid, the method comprising
the step of binding a protein expressed by a gene coding for a cis-prenyltransferase (CPT) family protein and a protein expressed by a gene coding for a Nogo-B receptor (NgBR) family protein to rubber particles in vitro.

2. The method for producing a polyisoprenoid according to claim 1,
wherein the cis-prenyltransferase (CPT) family protein comprises at least 80% sequence identity to the amino acid sequence of SEQ ID NO:2 and has an enzyme activity that catalyzes a reaction of cis-chain elongation of an isoprenoid compound and
wherein the protein further comprises:
an aspartic acid residue at position 41 in the amino acid sequence of SEQ ID NO:2;
a glycine residue at position 42 in the amino acid sequence of SEQ ID NO:2;
an arginine residue at position 45 in the amino acid sequence of SEQ ID NO:2; and
an asparagine residue at position 89 in the amino acid sequence of SEQ ID NO:2.

3. The method for producing a polyisoprenoid according to claim 2,
wherein the cis-prenyltransferase (CPT) family protein further comprises the following amino acid sequence (A): $DGNX_1RX_2AKK$ (A)
wherein $X_1$ and $X_2$ are the same as or different from each other and each represent any amino acid residue.

4. The method for producing a polyisoprenoid according to claim 2,
wherein the cis-prenyltransferase (CPT) family protein further comprises the following amino acid sequence (B): $TX_{11}X_{12}AFSX_{13}X_{14}NX_{15}X_{16}RX_{17}X_{18}X_{19}EV$ (B)
wherein $X_{11}$ to $X_{19}$ are the same as or different from each other and each represent any amino acid residue.

5. The method for producing a polyisoprenoid according to claim 1,
wherein at least one selected from the group consisting of the gene coding for a cis-prenyltransferase (CPT) family protein and the gene coding for a Nogo-B receptor (NgBR) family protein is derived from a plant.

6. The method for producing a polyisoprenoid according to claim 5,
wherein at least one selected from the group consisting of the gene coding for a cis-prenyltransferase (CPT) family protein and the gene coding for a Nogo-B receptor (NgBR) family protein is derived from *Hevea brasiliensis*.

7. The method for producing a polyisoprenoid according to claim 1,
wherein the binding step comprises performing protein synthesis in the presence of both rubber particles and a cell-free protein synthesis solution containing an mRNA coding for a cis-prenyltransferase (CPT) family protein and an mRNA coding for a Nogo-B receptor (NgBR) family protein to bind the CPT family protein and the NgBR family protein to the rubber particles.

8. The method for producing a polyisoprenoid according to claim 7,
wherein the cell-free protein synthesis solution contains a germ extract.

9. The method for producing a polyisoprenoid according to claim 8,
wherein the germ extract is derived from wheat.

10. The method for producing a polyisoprenoid according to claim 7,
wherein the rubber particles are present in the cell-free protein synthesis solution at a concentration of 5 to 50 g/L.

11. The method for producing a polyisoprenoid according to claim 1, wherein the polyisoprenoid is natural rubber.

12. The method for producing a polyisoprenoid according to claim 1, wherein the polyisoprenoid is very long chain polyisoprenoid.

13. The method for producing a polyisoprenoid according to claim 1, wherein the polyisoprenoid is polyisoprenoid rubber.

14. The method for producing a polyisoprenoid according to claim 1, the method further comprising
the step of preparing rubber particles by carrying out centrifugation at 500-1,500×g, centrifugation at 1,700-2,500×g, centrifugation at 7,000-9,000×g, centrifugation at 15,000-25,000×g, and centrifugation at 40,000-60,000×g in the stated order, and
the step of binding a protein expressed by a gene coding for a cis-prenyltransferase (CPT) family protein and a protein expressed by a gene coding for a Nogo-B receptor (NgBR) family protein to the rubber particles in vitro.

* * * * *

```
                       SEQUENCE LISTING

<160> NUMBER OF SEQ ID NOS: 64

<210> SEQ ID NO 1
<211> LENGTH: 873
<212> TYPE: DNA
<213> ORGANISM: Hevea brasiliensis

<400> SEQUENCE: 1
atggaattat acaacggtga gaggccaagt gtgttcagac ttttagggaa gtatatgaga       60
aaagggttat atagcatcct aacccagggt cccatcccta ctcatattgc cttcatattg      120
gatggaaaca ggaggtttgc taagaagcat aaactgccag aaggaggtgg tcataaggct      180 ggattttttag ctcttctgaa cgtactaact tattgctatg agttaggagt gaaatatgcg     240
actatctatg cctttagcat cgataatttt cgaaggaaac ctcatgaggt tcagtacgta      300
atggatctaa tgctggagaa gattgaaggg atgatcatgg aagaaagtat catcaatgca      360
tatgatattt gcgtacgttt tgtgggtaac ctgaagcttt taagtgagcc agtcaagacc      420
gcagcagata agattatgag ggctactgcc aacaattcca aatgtgtgct tctcattgct      480
gtatgctata cttcaactga tgagatcgtg catgctgttg aagaatcctc tgaattgaac      540
tccaatgaag tttgtaacaa tcaagaattg gaggaggcaa atgcaactgg aagcggtact      600
gtgattcaaa ttgagaacat ggagtcgtat tctggaataa aacttgtaga ccttgagaaa      660
aacacctaca taaatcctta tcctgatgtt ctgattcgaa cttctgggga gacccgtctg      720
agcaactact tactttggca gactactaat tgcatactgt attctcctca tgcactgtgg      780
ccagagattg gtcttcgaca cgtggtgtgg gcagtaatta acttccaacg tcattattct      840
tacttggaga aacataagga atacttaaaa taa                                   873

<210> SEQ ID NO 2
<211> LENGTH: 290
<212> TYPE: PRT
<213> ORGANISM: Hevea brasiliensis

<400> SEQUENCE: 2

Met Glu Leu Tyr Asn Gly Glu Arg Pro Ser Val Phe Arg Leu Leu Gly
1               5                   10                  15

Lys Tyr Met Arg Lys Gly Leu Tyr Ser Ile Leu Thr Gln Gly Pro Ile
            20                  25                  30

Pro Thr His Ile Ala Phe Ile Leu Asp Gly Asn Arg Arg Phe Ala Lys
        35                  40                  45
```

```
Lys His Lys Leu Pro Glu Gly Gly His Lys Ala Gly Phe Leu Ala
 50                  55                  60

Leu Leu Asn Val Leu Thr Tyr Cys Tyr Glu Leu Gly Val Lys Tyr Ala
 65                  70                  75                  80

Thr Ile Tyr Ala Phe Ser Ile Asp Asn Phe Arg Arg Lys Pro His Glu
                 85                  90                  95

Val Gln Tyr Val Met Asp Leu Met Leu Glu Lys Ile Glu Gly Met Ile
                100                 105                 110

Met Glu Glu Ser Ile Ile Asn Ala Tyr Asp Ile Cys Val Arg Phe Val
                115                 120                 125

Gly Asn Leu Lys Leu Leu Ser Glu Pro Val Lys Thr Ala Ala Asp Lys
130                 135                 140

Ile Met Arg Ala Thr Ala Asn Asn Ser Lys Cys Val Leu Leu Ile Ala
145                 150                 155                 160

Val Cys Tyr Thr Ser Thr Asp Glu Ile Val His Ala Val Glu Glu Ser
                165                 170                 175

Ser Glu Leu Asn Ser Asn Glu Val Cys Asn Asn Gln Glu Leu Glu Glu
                180                 185                 190

Ala Asn Ala Thr Gly Ser Gly Thr Val Ile Gln Ile Glu Asn Met Glu
                195                 200                 205

Ser Tyr Ser Gly Ile Lys Leu Val Asp Leu Glu Lys Asn Thr Tyr Ile
210                 215                 220

Asn Pro Tyr Pro Asp Val Leu Ile Arg Thr Ser Gly Glu Thr Arg Leu
225                 230                 235                 240

Ser Asn Tyr Leu Leu Trp Gln Thr Thr Asn Cys Ile Leu Tyr Ser Pro
                245                 250                 255

His Ala Leu Trp Pro Glu Ile Gly Leu Arg His Val Val Trp Ala Val
                260                 265                 270

Ile Asn Cys Gln Arg His Tyr Ser Tyr Leu Glu Lys His Lys Glu Tyr
                275                 280                 285

Leu Lys
    290

<210> SEQ ID NO 3
<211> LENGTH: 774
<212> TYPE: DNA
<213> ORGANISM: Hevea brasiliensis

<400> SEQUENCE: 3
atggatttga aacctggagc tggagggcag agagttaatc gattagtgga tccgattagt      60
tatcattttc ttcaatttct gtggcgtact ctacatcttc ttgtcagctt atggtacctt     120
caagttagta tggtccaaat gatcgaaggc tttctaatct ctagtggact tgtgaaacgc     180
tatggagccc tcgatattga caaggtccgg taccttgcca ttgtggtaga tagtgaagaa     240
gcttaccaaa tttctaaagt tattcagctt ttgaaatggg tggaagatat gggtgtgaaa     300
catttatgcc tctatgattc aaaaggagtt ctcaagacaa acaagaaaac catcatggag     360
agtttgaaca atgctatgcc atttgaggaa gcagttgaaa aagatgtttt actgaccag      420 aaacagatga ctgtggaatt tgcttccagc tccgatggaa aggaagcaat aaccagggca     480
gctaacgtac tctttatgaa gtatttgaag tatgctaaaa ctggtgtagg aaaggaagaa     540
ccatgcttta cagaagatca aatggatgag gcactaaaag ctataggtta caaagggccg     600
gaacctgact tgctattaat ttatggacct gttagatgcc atctaggttt ctcaccgtgg     660
```
agacttcgat atactgagat ggtgcatatg ggacccttga ggtacatgaa cctcggttca    720
ctaaaaaagg ccattcacag gttcacaaca gtgcagcaaa attatggtac atga    774

```
<210> SEQ ID NO 4
<211> LENGTH: 257
<212> TYPE: PRT
<213> ORGANISM: Hevea brasiliensis

<400> SEQUENCE: 4
```

Met Asp Leu Lys Pro Gly Ala Gly Gly Gln Arg Val Asn Arg Leu Val
1               5                   10                  15

Asp Pro Ile Ser Tyr His Phe Leu Gln Phe Leu Trp Arg Thr Leu His
            20                  25                  30

Leu Leu Val Ser Leu Trp Tyr Leu Gln Val Ser Met Val Gln Met Ile
        35                  40                  45

Glu Gly Phe Leu Ile Ser Ser Gly Leu Val Lys Arg Tyr Gly Ala Leu
    50                  55                  60

Asp Ile Asp Lys Val Arg Tyr Leu Ala Ile Val Val Asp Ser Glu Glu
65                  70                  75                  80

Ala Tyr Gln Ile Ser Lys Val Ile Gln Leu Leu Lys Trp Val Glu Asp
                85                  90                  95

Met Gly Val Lys His Leu Cys Leu Tyr Asp Ser Lys Gly Val Leu Lys
            100                 105                 110

Thr Asn Lys Lys Thr Ile Met Glu Ser Leu Asn Asn Ala Met Pro Phe
        115                 120                 125

Glu Glu Ala Val Glu Lys Asp Val Leu Leu Asp Gln Lys Gln Met Thr
    130                 135                 140

Val Glu Phe Ala Ser Ser Ser Asp Gly Lys Glu Ala Ile Thr Arg Ala
145                 150                 155                 160

Ala Asn Val Leu Phe Met Lys Tyr Leu Lys Tyr Ala Lys Thr Gly Val
                165                 170                 175

Gly Lys Glu Glu Pro Cys Phe Thr Glu Asp Gln Met Asp Glu Ala Leu
            180                 185                 190

Lys Ala Ile Gly Tyr Lys Gly Pro Glu Pro Asp Leu Leu Leu Ile Tyr
        195                 200                 205

Gly Pro Val Arg Cys His Leu Gly Phe Ser Pro Trp Arg Leu Arg Tyr
    210                 215                 220

Thr Glu Met Val His Met Gly Pro Leu Arg Tyr Met Asn Leu Gly Ser
225                 230                 235                 240

Leu Lys Lys Ala Ile His Arg Phe Thr Thr Val Gln Gln Asn Tyr Gly
                245                 250                 255

Thr

```
<210> SEQ ID NO 5
<211> LENGTH: 34
<212> TYPE: DNA
<213> ORGANISM: Artificial Sequence
<220> FEATURE:
<223> OTHER INFORMATION: PRIMER-1

<400> SEQUENCE: 5
```
tttggatccg atggaattat acaacggtga gagg    34

```
<210> SEQ ID NO 6
<211> LENGTH: 39
<212> TYPE: DNA
<213> ORGANISM: Artificial Sequence
```

```
<220> FEATURE:
<223> OTHER INFORMATION: PRIMER-2

<400> SEQUENCE: 6
tttgcggccg cttatttttaa gtattcctta tgtttctcc                    39

<210> SEQ ID NO 7
<211> LENGTH: 31
<212> TYPE: DNA
<213> ORGANISM: Artificial Sequence
<220> FEATURE:
<223> OTHER INFORMATION: PRIMER-3

<400> SEQUENCE: 7
tttctcgaga tggatttgaa acctggagct g                              31

<210> SEQ ID NO 8
<211> LENGTH: 33
<212> TYPE: DNA
<213> ORGANISM: Artificial Sequence
<220> FEATURE:
<223> OTHER INFORMATION: PRIMER-4

<400> SEQUENCE: 8
tttctcgagt catgtaccat aattttgctg cac                            33

<210> SEQ ID NO 9
<211> LENGTH: 1650
<212> TYPE: DNA
<213> ORGANISM: Hevea brasiliensis

<400> SEQUENCE: 9
gtagtcacag cataagttgg agcaaacaca aaactacagg cctcccaggt tttaaaaaaa    60
aaaaaaaact tttctacgca taaattttcc aagaaaaata ttttgagga ataatttatt    120 tttattgttc tgttaaaatc tgaaaataaa gaaaaattac ttcctaatgg ttcaaggaaa    180
aaataataat tttatttttg tttataatat tatgaaaata tttaaattat aaaactttaa    240
tttttatttt tttattgtga aatgtataaa aaatacataa aataataaaa ttgtgtttta    300
gccatcctgg ctgttgaggc cgcaaggccc gcaagcagta gccggtaaag gaaaaaccag    360
gggcaatatt tttgcagggt tttttttttt tttttttcttt aaaagtaaag aacgtatgta    420
tgagtcttaa agatagtaat tttaatagag tctttgatct tatataattc tcacacattt    480
ttacaatctg atgtggaatc ctaaagtact aactcgtgtc tatgcccatc actcgcaaac    540
ttcaatcagg atcacatcat ggactctcat tttttctttg ttttcactta agtgattaat    600 tttcttttg tcaaggtaa agaatataca cacatattag aaacaggatt agataattat    660 aaaaaagga taattttaat gaaattttta attctatata attcattcac acgtactttc    720
accgcttaat atgtgatatg aaggaattta gccctaattt ggttaagaat taatataaat    780
taaaattata ttgtattaga ttaaattaaa ataaaaatat taaattaatt tttttagaaa    840
aattaaaatt gatcttgaac caaactcaaa taaagttaat ttgatccctt catttttttt    900
ttattttaat gaaaatttaa attgagatct tgtaattttg gaagccattt aaatatattc    960
gatttgctaa taattatgct gaatgtaatt taatggtaaa gaaataaat aataaaaag    1020 atacatttaa tttaatttaa tttatatat tttttattc aaaaaatttt aaaaaggaac    1080
agattgttaa atcttttattt ttttaattaa attaaattta attgagtctc aaatataata    1140
ttttataatc ttaaaaataa ttttaatatt actgatttaa atttatagat ttaatttaaa    1200
```

```
aatttttaaa agtaaagaaa ataattaaga ttttaatttt taagtcgcac gtgattttga    1260
atttaatttt ttaaaaacaa agactaactt atttttttat aatttattaa gaaaatcatg    1320
aaaatcccca ttctaaatcg acttctggaa ctgggatgat gcgtttgctt tgcgatactc    1380
catgtgcttt acttacccca taaggatcat gcgcgaatca cgatagaacc aatacaacag    1440
caacacgttt acacgctcct tttcttaaca gctggcctgc cattcccacg aatttccatc    1500
tataagtaga gaggtttggt tttagcatca aaccataatc ggttgatagc ctccatcagc    1560
gttttcagaa aggcgggttt cttttttgaa acttaagcga ctgcgttttg aattttgatc    1620
ttccattttt gcaaaaggaa atcttcgatt                                     1650

<210> SEQ ID NO 10
<211> LENGTH: 919
<212> TYPE: DNA
<213> ORGANISM: Hevea brasiliensis

<400> SEQUENCE: 10
aaccgtccac caatctttga gttccagtga gtcatctact ggttgcttga cagatccatc      60
aataaaacca tatttctttt tggcccgtaa tgcagtcagc atagctcgcg cccattcttc     120
gtaattctcg cccttcaact gaacttgggt aatcaagtta tctgggttgt cattcgaatt     180
cagtgtttaa gaactaaaag ttttcttccc tgatccagaa ctctcatttt tcttttcatc     240
aaccatggct ctgataccat gtaaaaaaac taagaaattt tggaataaga attcttatct     300
ttattgcccc agaaataaaa tatatatata aaaaaattac agctaacaaa taggtcccta     360
atcaagctaa actaccaaaa ttgtatcaaa gtcatacaac aaaaggtaaa aacagatatg     420
cacacaaaaa ttcctaaaca aatgccctaa ataaatacaa aataagtgac agctaacagc     480
tgcatttcca ataattaatt taactaataa aatttatata cttaaaaata attttaatat     540
tattgaatta aaatttataa ataaaattaa cactgttaaa attaaaagaa aattattaag     600
atttgaattt ttaagcggtt atttaatttt gaaaacaag gctaactttt ttttttatat      660
aatttactaa aaaattcatg aatgaaaaaa aaaatccat aagtaaactt accccatacg      720
ggttatgcac gctaaaccaa taaaacagaa acacgtttat acactcgttt tcatttccat     780
ctataaatag agagatttgt ttttagttttt aaaccataat cagttgatag cttccacagt     840
gttttccgaa aggcaaatct ttttcaaac ttcagcgact gcgttttgaa tttgtgatttt      900 ttaaaggaaa ttttcaatt                                                  919

<210> SEQ ID NO 11
<211> LENGTH: 1680
<212> TYPE: DNA
<213> ORGANISM: Hevea brasiliensis

<400> SEQUENCE: 11
ggctacctta ttgggaacta ccaatttgtg gattgtggtg attgaattaa ctaataagca      60
actgaatgtt aatttccaga ataagaaaac ttgctgattg taatctcaag ttctagagtg     120
aaaataaaga taattatata aaatatatgg aaattattat cctagaggaa atttatttt      180 ttttaaattt aataaaattt ttgtaattaa aaattttacg aaaaaaaatc taataaaata     240
aatttatgta aaattacttt atttttttata ataaaataat tacattatgt atgaaactaa     300
gtaatcatag aatatatata tatattattt agtttatgtg tcaaatataa tagattaata     360 ttttcttttat tattttcaa aataattttc atgtcaaccc aattaaataa atatccaact     420 aattttttttt ttaaatattt ttatttcaca gagaataatt tgtatataaa aaataatttt     480
```

-continued

| | |
|---|---|
| cataaaaata tttttatta tttaatttta acattaatta atggtacgtg ttcatattat | 540 |
| atatgaataa tattttata ttttaataaa attatcaaag ttgagaaaat gatttgctct | 600 |
| tttaagttct ctcttaaaaa agaaagtcat ttttcttaaa aataatttaa tttctctttg | 660 |
| actaaaatat ttttgttaa ttatttttt aatactccaa acacaaaaaa tgtgaaaaaa | 720 |
| aaaatatttt ccacgacaca aacaaacaga attttagcca atcaattagc gcaattttca | 780 |
| actcccccgc ctcctaaagg ctggactggt gttgttcctg gaggctgata tcctaagcag | 840 |
| gtttctggat ttgcactgat tccatgatgg ttgaggcaag agggtatttc taatgagttt | 900 |
| ttatttagcc ctcttggttg ttgcctgcca ctggaaatca ccatggaaac atatatgaag | 960 |
| tcaaatgaca attttattt tttaaatttt ctgagagtga ggaaatgaat aagaagaatt | 1020 |
| tgttatttt ctttaaagtc gtgttacttt tacataatat attaagtcaa atttatcgac | 1080 |
| tcagtgaaaa taatttatat tttataaata agaaaaatct tgttatataa tttaatataa | 1140 |
| attttatatc ttttttttt caaggaaata aattttatat cttgatgata agatagagat | 1200 |
| aagatcgagt taacccttgc gttaattgga tgtttaaatg cttaatgcat ggctaaggaa | 1260 |
| attaatgtct aaaataacag aaatgagaaa aataaatgaa gggtgaaaaa taaataaaac | 1320 |
| ctggccctat gctctatatt ggggatggag tgggagccac ctaatgtgtc agtgttcatc | 1380 |
| ttcgaacaac gactcgattc aaagcacacc catgaagccg cttcacatca tcccttgaa | 1440 |
| actttccacc ctaatcagct atcacacgat ctactttcca atctcatcaa cgctccaaat | 1500 |
| ctcaccacca ttcagtccac tttcacttcc tccttgtcct aatcatcttt aatccatcgg | 1560 |
| ggtattatgg taattacatg atcaagtctc tctgctataa ataaagccaa gtgagcttag | 1620 |
| ctcatcatca catcatttgc ataccagaaa atcaagaatt gggaagaaat gggaagagtt | 1680 |

<210> SEQ ID NO 12
<211> LENGTH: 1610
<212> TYPE: DNA
<213> ORGANISM: Hevea brasiliensis

<400> SEQUENCE: 12

| | |
|---|---|
| taccagctat gattcacctc tagtgatatt gattttatta aaaattaagg caatgatgaa | 60 |
| tttcttttg aaaaaatcat ttaagattca agagggagat acagtgatgt cgttattttt | 120 |
| taattttatg taagtaaaat tcgtcaatca ttcatcaaag ttaactgcgt gctaaataat | 180 |
| ttaaaaatta ttgtttttta tttttgaaaa ttataataaa attcatttgt tttaataatt | 240 |
| aggttcttag tttataattt ttttatttta aatttaagta tttatgatta attctgattt | 300 |
| aatttctgat aatttttaaaa ttaaaattat ttgattctta caaattttta acaatcattg | 360 |
| ttttagacca atctcaaagt aaatgttttca cacgttacaa gggtgcaaaa tgattggacg | 420 |
| gtgacagaaa cagtaaatat tatgaattta attgttgcca tgggctgcta aattcaaagg | 480 |
| gtcatcatta cgtgattctc gatttacgaa aaaaaaaag tattttcata tatatatgta | 540 |
| tatacacaca cacatcatgc aaaatatta gttaataatt ttccaaaatt aaaactttt | 600 |
| tttatagcat acaattaaaa tgttaaattc aattaaaaaa gtgaaaataa aatataatt | 660 |
| ttttacataa aaaatataaa tttttatataa ttattagtga gaatatatat tactagatttt | 720 |
| aaaatatact gaataaccac tcgcttttta attggttata gtgattaatt aagaattttt | 780 |
| tttatctaaa tttattaagt gatccaacaa atttttgaact attatataag ttttataaaat | 840 |
| tttgattctc cattctacat tttaaatttt tcatttttta tattatgaaa atatatacat | 900 |
| aaaaaaatta attaaactag agttaattgt cagaatgaat ctctagtaaa attttctctg | 960 |

```
attaaaaaat aaatttcata aattatccca ctaaactttt gtcatgtgat catgtcccca    1020
ataaaatttg attttattat aattggcaac tcgatgtcta acctgcgagt aattatacac    1080
catccccatg atacctccat gatttcaagt gtcaaagtat gttttaatga gaaattatta    1140
ggttaactca atgtatatac attattttt ataattatgt gaattaatt ctcataatta     1200 tataggacac atacttcgtc cacttatttt ttagaaaaaa agcattattt tttagcactt    1260
tcaatgtaac taataattaa cggttttaa catgtaagta taattgaata ttataaaacg     1320
cattaataca tatatatgca tgattcttgt taatttacca ttctacgtag aatattccat    1380
atagaatcaa tgctttatta tataataatt tctgctacat aataagaggc tttcatttcc    1440 tttgtctta aataacccca agtctcactt gtaaaccaac gtcgctcatt tatccctctt     1500
accctgtccc tctccaactc tcaaactttc tggaattcca tagattgtgg aaactctcta    1560
gctaaaccaa aaacagaaa agaacataca aaattgaaat actaaggtgc                1610

<210> SEQ ID NO 13
<211> LENGTH: 889
<212> TYPE: DNA
<213> ORGANISM: Lactuca sativa

<400> SEQUENCE: 13
atggaattgg atccaatcat tgcaacggac acctcgctga acaagcggaa agacgaaaga     60
tcaaatggta cgatcagcaa gctccttgga ggcgtaaacc acaccttaag aaaactcata   120
tttcgtgtca tttcttcacg cccgattcca gaacacatcg ccttcatcct cgacggaaac   180
cgaaggtttg ccaagaaatg gaagctcacg gaaggtgcag gtcacaaagc cggttttttc   240
gcactcatgg cagtcctaaa atactgctac gagataggag ttaagtatgt caccatctat   300
gcattcagcc tcgacaattt caatcgacgc cctgatgaag tccaatacgt aatggatttg   360
atgcaagaaa agatcgaagg gtttctaaat gaacttactc ttataaacca atatggcgtt   420
agagtcttgt ttattggcga tctcgatagg ttatatgaac ccgtaaggat tgctgctgag   480
aaggccatgg aagccaccgc taagaactca cgcacatatc tcctagtatg tgttgcatac   540
acttcttccc atgaaatccc acgagcaatc cacgaagctt gtcaagaaaa aagtgaggct   600
aatagcatac gtgtcatgaa tagtgacata aatcatggtg gtcaatcggt gatcaaagtg   660
gtggatcttg agaagcatat gtacatggga gtggctccgg atcctgatat tctagtgagg   720
agctccggcg agacaaggtt aagcaacttt ctgttgtggc aaaccaccaa ctctttcttg   780
tattccccga agctttgtg gccagagatg ggattctggc aggtggtttg ggggatcttg    840
gagtttcaga acaactatca gtactatgag aagaagaaga agcaggctt                889

<210> SEQ ID NO 14
<211> LENGTH: 296
<212> TYPE: PRT
<213> ORGANISM: Lactuca sativa

<400> SEQUENCE: 14

Met Glu Leu Asp Pro Ile Ile Ala Thr Asp Thr Ser Leu Lys Gln Ala
1               5                   10                  15

Glu Asp Glu Arg Ser Asn Gly Thr Ile Ser Lys Leu Leu Gly Gly Val
            20                  25                  30

Asn His Thr Leu Arg Lys Leu Ile Phe Arg Val Ile Ser Ser Arg Pro
        35                  40                  45

Ile Pro Glu His Ile Ala Phe Ile Leu Asp Gly Asn Arg Arg Phe Ala
    50                  55                  60
```

Lys Lys Trp Lys Leu Thr Glu Gly Ala Gly His Lys Ala Gly Phe Phe
65                  70                  75                  80

Ala Leu Met Ala Val Leu Lys Tyr Cys Tyr Glu Ile Gly Val Lys Tyr
                85                  90                  95

Val Thr Ile Tyr Ala Phe Ser Leu Asp Asn Phe Asn Arg Arg Pro Asp
            100                 105                 110

Glu Val Gln Tyr Val Met Asp Leu Met Gln Glu Lys Ile Glu Gly Phe
        115                 120                 125

Leu Asn Glu Leu Thr Leu Ile Asn Gln Tyr Gly Val Arg Val Leu Phe
    130                 135                 140

Ile Gly Asp Leu Asp Arg Leu Tyr Glu Pro Val Arg Ile Ala Ala Glu
145                 150                 155                 160

Lys Ala Met Glu Ala Thr Ala Lys Asn Ser Arg Thr Tyr Leu Leu Val
                165                 170                 175

Cys Val Ala Tyr Thr Ser Ser His Glu Ile Pro Arg Ala Ile His Glu
            180                 185                 190

Ala Cys Gln Glu Lys Ser Glu Ala Asn Ser Ile Arg Val Met Asn Ser
        195                 200                 205

Asp Ile Asn His Gly Gly Gln Ser Val Ile Lys Val Val Asp Leu Glu
    210                 215                 220

Lys His Met Tyr Met Gly Val Ala Pro Asp Pro Asp Ile Leu Val Arg
225                 230                 235                 240

Ser Ser Gly Glu Thr Arg Leu Ser Asn Phe Leu Leu Trp Gln Thr Thr
                245                 250                 255

Asn Ser Phe Leu Tyr Ser Pro Lys Ala Leu Trp Pro Glu Met Gly Phe
            260                 265                 270

Trp Gln Val Val Trp Gly Ile Leu Glu Phe Gln Asn Asn Tyr Gln Tyr
        275                 280                 285

Tyr Glu Lys Lys Lys Lys Gln Ala
    290                 295

<210> SEQ ID NO 15
<211> LENGTH: 732
<212> TYPE: DNA
<213> ORGANISM: Lactuca sativa

<400> SEQUENCE: 15
atggatctcg taggtggacc ccagaagatt ttacacaaaa tctcactgaa tgatcacatg        60
atacttctgt tgctgtggca cattcttcat ttaattgttc aagtcatata ctttgtttgg       120
gagaagatgc gtgcaattga agctatcttt atagcaaatg gaattgtcaa acatatgaa       180 gatctgaatt tagacagagt gaagtatctt ggaattgtgg tggatagtga tgaagctcgt       240
gaaacctcaa agttattga acttttggag tggatttcag atattggtgt gaaaaaggtc       300
tgcctttatg acagagaagg agtgttgaag aagtccaagg aactgttcat ggagaaattt       360
gattctatgg agaattcaga aactaatcaa aaaaggaaaa tggattttga atttgtttca       420
atcgttgatg gaaagaaac agttgctaaa gcagcgaatc tgctatataa aaagtattat       480
tctgatccaa attcagaaaa accattcttt actgaaacct atttgaccga agcacttagg       540
atcctaggtt ctaatgagcc ggatcctgat cttatactga tttatgggcc cacaaggtgc       600
caccttggtt ttccagcatg gcgtattcgt tatacagaga tggtacacat gggatcattg       660
aagaacaaga agtttggttt gattttgaaa gccatcaaca atacaccaa ggtgaagcag       720 aactacggtt ct                                                          732

```
<210> SEQ ID NO 16
<211> LENGTH: 244
<212> TYPE: PRT
<213> ORGANISM: Lactuca sativa

<400> SEQUENCE: 16

Met Asp Leu Val Gly Gly Pro Gln Lys Ile Leu His Lys Ile Ser Leu
 1               5                  10                  15

Asn Asp His Met Ile Leu Leu Leu Trp His Ile Leu His Leu Ile
                20                  25                  30

Val Gln Val Ile Tyr Phe Val Trp Glu Lys Met Arg Ala Ile Glu Ser
                35                  40                  45

Tyr Leu Ile Ala Asn Gly Ile Val Lys Thr Tyr Glu Asp Leu Asn Leu
    50                  55                  60

Asp Arg Val Lys Tyr Leu Gly Ile Val Val Asp Ser Asp Glu Ala Arg
65                  70                  75                  80

Glu Thr Ser Lys Val Ile Glu Leu Leu Glu Trp Ile Ser Asp Ile Gly
                85                  90                  95

Val Lys Lys Val Cys Leu Tyr Asp Arg Glu Gly Val Leu Lys Lys Ser
                100                 105                 110

Lys Glu Leu Phe Met Glu Lys Phe Asp Ser Met Glu Asn Ser Glu Thr
            115                 120                 125

Asn Gln Lys Arg Lys Met Asp Phe Glu Phe Val Ser Ile Val Asp Gly
    130                 135                 140

Lys Glu Thr Val Ala Lys Ala Ala Asn Leu Leu Tyr Lys Lys Tyr Tyr
145                 150                 155                 160

Ser Asp Pro Asn Ser Glu Lys Pro Phe Phe Thr Glu Thr Tyr Leu Thr
                165                 170                 175

Glu Ala Leu Arg Ile Leu Gly Ser Asn Glu Pro Asp Pro Asp Leu Ile
            180                 185                 190

Leu Ile Tyr Gly Pro Thr Arg Cys His Leu Gly Phe Pro Ala Trp Arg
        195                 200                 205

Ile Arg Tyr Thr Glu Met Val His Met Gly Ser Leu Lys Asn Lys Lys
    210                 215                 220

Phe Gly Leu Ile Leu Lys Ala Ile Asn Lys Tyr Thr Lys Val Lys Gln
225                 230                 235                 240

Asn Tyr Gly Ser

<210> SEQ ID NO 17
<211> LENGTH: 28
<212> TYPE: DNA
<213> ORGANISM: Artificial Sequence
<220> FEATURE:
<223> OTHER INFORMATION: PRIMER-5

<400> SEQUENCE: 17
ctaggatccg agatgaatac cctagaag                                       28

<210> SEQ ID NO 18
<211> LENGTH: 25
<212> TYPE: DNA
<213> ORGANISM: Artificial Sequence
<220> FEATURE:
<223> OTHER INFORMATION: PRIMER-6

<400> SEQUENCE: 18
aacggatcca actatctaat cgagc                                          25
```

```
<210> SEQ ID NO 19
<211> LENGTH: 38
<212> TYPE: DNA
<213> ORGANISM: Artificial Sequence
<220> FEATURE:
<223> OTHER INFORMATION: PRIMER-7

<400> SEQUENCE: 19
cgggatccat ggattcgaat caatcgatgc ggctcctc                              38

<210> SEQ ID NO 20
<211> LENGTH: 38
<212> TYPE: DNA
<213> ORGANISM: Artificial Sequence
<220> FEATURE:
<223> OTHER INFORMATION: PRIMER-8

<400> SEQUENCE: 20
gcggatccaa ttgggaacag tagtggctgc actgactc                              38

<210> SEQ ID NO 21
<211> LENGTH: 1029
<212> TYPE: DNA
<213> ORGANISM: Arabidopsis thaliana

<400> SEQUENCE: 21
aacaaagtgt gttcttaaat tatcttctct gataaccaaa aaagccctat tttccgagat      60
gaatacccta gaagaagtag atgaatccac tcatatcttc aacgctttga tgagtctaat     120
gaggaaattt ttgttcagag ttctatgcgt cggtccaatc cctactaaca tttcattcat     180
catggatgga aaccgcaggt tcgctaagaa acacaatctt ataggcctag atgcaggaca     240
tagagctggt ttcatatccg tgaaatatat tcttcaatac tgcaaagaga ttggtgtacc     300
gtacgtcaca ctccacgcgt ttggtatgga taatttcaag agaggacctg aagaagtcaa     360
gtgtgtgatg gatctaatgc ttgagaaagt cgagctcgcg atcgatcaag ctgtatcagg     420
gaatatgaac ggcgtgagaa taatctttgc cggtgatttg gattcgttaa acgagcattt     480
tagagctgcg acaaagaaac tgatggagct tacggaggag aatagagatc tgattgtggt     540
ggtttgcgtt gcttacagca caagtctcga gattgttcac gctgttcgaa aatcttgtgt     600
tagaaaatgt acgaatggag atgatcttgt acttttggag ttgagtgatg ttgaagagtg     660
tatgtataca tcgattgtgc cggttccgga tcttgtgata agaaccggag gaggagatcg     720
gctgagtaac ttcatgacgt ggcaaacttc gaggtctctt cttcacagaa cggaggctct     780
ttggccggag ttagggctct ggcatttggt ttgggcaatt cttaaattcc aaagaatgca     840
agattacttg acgaagaaga aaaagctcga ttagatagtt tctaaagtta aaccctgcag     900
gaaagaactt ttaactcttt attacgttta atttacgtgt ttctatgact ggaaacgaga     960
aagctcacaa gcaaatcttt tttattatgt attggatccg tataacaaac acgaatatac    1020
aaaacatcg                                                           1029

<210> SEQ ID NO 22
<211> LENGTH: 271
<212> TYPE: PRT
<213> ORGANISM: Arabidopsis thaliana
```

<400> SEQUENCE: 22

```
Met Asn Thr Leu Glu Glu Val Asp Glu Ser Thr His Ile Phe Asn Ala
1               5                   10                  15
Leu Met Ser Leu Met Arg Lys Phe Leu Phe Arg Val Leu Cys Val Gly
            20                  25                  30
Pro Ile Pro Thr Asn Ile Ser Phe Ile Met Asp Gly Asn Arg Arg Phe
        35                  40                  45
Ala Lys Lys His Asn Leu Ile Gly Leu Asp Ala Gly His Arg Ala Gly
    50                  55                  60
Phe Ile Ser Val Lys Tyr Ile Leu Gln Tyr Cys Lys Glu Ile Gly Val
65                  70                  75                  80
Pro Tyr Val Thr Leu His Ala Phe Gly Met Asp Asn Phe Lys Arg Gly
            85                  90                  95
Pro Glu Glu Val Lys Cys Val Met Asp Leu Met Leu Glu Lys Val Glu
        100                 105                 110
Leu Ala Ile Asp Gln Ala Val Ser Gly Asn Met Asn Gly Val Arg Ile
    115                 120                 125
Ile Phe Ala Gly Asp Leu Asp Ser Leu Asn Glu His Phe Arg Ala Ala
130                 135                 140
Thr Lys Lys Leu Met Glu Leu Thr Glu Glu Asn Arg Asp Leu Ile Val
145                 150                 155                 160
Val Val Cys Val Ala Tyr Ser Thr Ser Leu Glu Ile Val His Ala Val
            165                 170                 175
Arg Lys Ser Cys Val Arg Lys Cys Thr Asn Gly Asp Asp Leu Val Leu
        180                 185                 190
Leu Glu Leu Ser Asp Val Glu Glu Cys Met Tyr Thr Ser Ile Val Pro
    195                 200                 205
Val Pro Asp Leu Val Ile Arg Thr Gly Gly Gly Asp Arg Leu Ser Asn
        210                 215                 220
Phe Met Thr Trp Gln Thr Ser Arg Ser Leu Leu His Arg Thr Glu Ala
225                 230                 235                 240
Leu Trp Pro Glu Leu Gly Leu Trp His Leu Val Trp Ala Ile Leu Lys
            245                 250                 255
Phe Gln Arg Met Gln Asp Tyr Leu Thr Lys Lys Lys Leu Asp
        260                 265                 270
```

<210> SEQ ID NO 23
<211> LENGTH: 1248
<212> TYPE: DNA
<213> ORGANISM: Arabidopsis thaliana

<400> SEQUENCE: 23

```
gatcttcaaa agtgtctcac tttttctaac ctcgcctcca agattcttc ctttccgat     60
tccgatgaaa aggaattttg ggttttagga aagttcgatt ggttggtttg gaaacatctc  120
cctaacacac gcagcaaaca ctttcgttgt ttacggagac agtcactttt tgtatatatg  180
gattcgaatc aatcgatgcg gctcctcagt gcttggattg gtcaaattgg tgatcttggt  240
cttaatttgc tatggcgttt tatacacatt gttgtgagct tatggtacat tgtctctggc  300
atatttgagg caatagaaag ctatgccata acgttaggat tgaataaaaa gtacggttcc  360
atcgatcttg agaaactccg gtgtctagct gttgtagtgg acatcgaagc agctcaagat  420
gttgccaatg ttgttgagct tttgcaatgg ctaaccacca ttgggggttaa caagttggt  480
ctatttgact ctcaaggttt attgaagaaa tccaaggatt tgatccttga aaccgttcca  540
```

```
ggttccatgt tgttagagga gattgaaaag gatgttgcgc ctgacggaaa gcgcattgca    600
ttagaattca tttcatcttc agacaataaa gaagctgtta tgaaagcagc caacatactt    660
cttcagagat acttgaaatc cagccatcct gaggacgaca aggggaaga ctttttaca     720 gagtctcatt tgaatgacgc attaagagtt gttggtgaga atgtgcatgt acccgatctg    780
ttactggttt atggacctat aaggagccac ctcggtttcc ctgcttggag acttcgatac    840
actgagatag tacatatggg aactttgaag tatatgagat atggttccct tttgaaggca    900
attcacaagt tcacaggagt ccaccaaaac tatggaactt aacggtgact agagagcaga    960
gtttcagaga tcgattttg gtttgtgatt cacatatttg caatgaattc taaaggagag    1020
attattggag agcttttgag tcagtgcagc cactactgtt cccaatttcc ggcaattcta    1080
tgtaccaaag caacatatgc attggcattg taggatta agtagtaaca agctggacct     1140
aaccaatccg gtttttccat aaagttccgg tttgcttggt tatcgtgtgt aaacaaaaat    1200
agaacacaac tttcagattt ttcagtaaaa aaataaacag tttagttt               1248
```

<210> SEQ ID NO 24
<211> LENGTH: 254
<212> TYPE: PRT
<213> ORGANISM: Arabidopsis thaliana

<400> SEQUENCE: 24

```
Met Asp Ser Asn Gln Ser Met Arg Leu Leu Ser Ala Trp Ile Gly Gln
1               5                   10                  15

Ile Gly Asp Leu Gly Leu Asn Leu Leu Trp Arg Phe Ile His Ile Val
            20                  25                  30

Val Ser Leu Trp Tyr Ile Val Ser Gly Ile Phe Glu Ala Ile Glu Ser
        35                  40                  45

Tyr Ala Ile Thr Leu Gly Leu Asn Lys Lys Tyr Gly Ser Ile Asp Leu
    50                  55                  60

Glu Lys Leu Arg Cys Leu Ala Val Val Asp Ile Glu Ala Ala Gln
65                  70                  75                  80

Asp Val Ala Asn Val Val Glu Leu Leu Gln Trp Leu Thr Thr Ile Gly
                85                  90                  95

Val Lys Gln Val Gly Leu Phe Asp Ser Gln Gly Leu Leu Lys Lys Ser
            100                 105                 110

Lys Asp Leu Ile Leu Glu Thr Val Pro Gly Ser Met Leu Leu Glu Glu
        115                 120                 125

Ile Glu Lys Asp Val Ala Pro Asp Gly Lys Arg Ile Ala Leu Glu Phe
    130                 135                 140

Ile Ser Ser Ser Asp Asn Lys Glu Ala Val Met Lys Ala Ala Asn Ile
145                 150                 155                 160

Leu Leu Gln Arg Tyr Leu Lys Ser Ser His Pro Glu Asp Asp Lys Gly
                165                 170                 175

Glu Asp Phe Phe Thr Glu Ser His Leu Asn Asp Ala Leu Arg Val Val
            180                 185                 190

Gly Glu Asn Val His Val Pro Asp Leu Leu Leu Val Tyr Gly Pro Ile
        195                 200                 205

Arg Ser His Leu Gly Phe Pro Ala Trp Arg Leu Arg Tyr Thr Glu Ile
    210                 215                 220

Val His Met Gly Thr Leu Lys Tyr Met Arg Tyr Gly Ser Leu Leu Lys
225                 230                 235                 240

Ala Ile His Lys Phe Thr Gly Val His Gln Asn Tyr Gly Thr
                245                 250
```

```
<210> SEQ ID NO 25
<211> LENGTH: 27
<212> TYPE: DNA
<213> ORGANISM: Artificial Sequence
<220> FEATURE:
<223> OTHER INFORMATION: PRIMER-9

<400> SEQUENCE: 25
tttctcgaga tggctgaaga cgaagac                                         27

<210> SEQ ID NO 26
<211> LENGTH: 28
<212> TYPE: DNA
<213> ORGANISM: Artificial Sequence
<220> FEATURE:
<223> OTHER INFORMATION: PRIMER-10

<400> SEQUENCE: 26
tttggatcct caattctctc cataaaac                                        28

<210> SEQ ID NO 27
<211> LENGTH: 417
<212> TYPE: DNA
<213> ORGANISM: Hevea brasiliensis

<400> SEQUENCE: 27
atggctgaag acgaagacaa ccaacaaggg caggggagg ggttaaaata tttgggtttt      60
gtgcaagacg cggcaactta tgctgtgact accttctcaa acgtctatct ttttgccaaa    120
gacaaatctg gtccactgca gcctggtgtc gatatcattg agggtccggt gaagaacgtg    180
gctgtacctc tctataatag gttcagttat attcccaatg gagctctcaa gtttgtagac    240
agcacggttg ttgcatctgt cactattata gatcgctctc ttcccccaat tgtcaaggac    300
gcatctatcc aagttgtttc agcaattcga gctgccccag aagctgctcg ttctctggct    360
tcttctttgc ctgggcagac caagatactt gctaaggtgt tttatggaga gaattga       417

<210> SEQ ID NO 28
<211> LENGTH: 138
<212> TYPE: PRT
<213> ORGANISM: Hevea brasiliensis

<400> SEQUENCE: 28

Met Ala Glu Asp Glu Asp Asn Gln Gln Gly Gln Gly Glu Gly Leu Lys
1               5                   10                  15

Tyr Leu Gly Phe Val Gln Asp Ala Ala Thr Tyr Ala Val Thr Thr Phe
            20                  25                  30

Ser Asn Val Tyr Leu Phe Ala Lys Asp Lys Ser Gly Pro Leu Gln Pro
        35                  40                  45

Gly Val Asp Ile Ile Glu Gly Pro Val Lys Asn Val Ala Val Pro Leu
    50                  55                  60

Tyr Asn Arg Phe Ser Tyr Ile Pro Asn Gly Ala Leu Lys Phe Val Asp
65                  70                  75                  80

Ser Thr Val Val Ala Ser Val Thr Ile Ile Asp Arg Ser Leu Pro Pro
                85                  90                  95

Ile Val Lys Asp Ala Ser Ile Gln Val Val Ser Ala Ile Arg Ala Ala
            100                 105                 110

Pro Glu Ala Ala Arg Ser Leu Ala Ser Ser Leu Pro Gly Gln Thr Lys
        115                 120                 125

Ile Leu Ala Lys Val Phe Tyr Gly Glu Asn
    130                 135
```

<210> SEQ ID NO 29
<211> LENGTH: 34
<212> TYPE: DNA
<213> ORGANISM: Artificial Sequence
<220> FEATURE:
<223> OTHER INFORMATION: PRIMER-11

<400> SEQUENCE: 29
tttggatccg atggaattat acaacggtga gagg          34

<210> SEQ ID NO 30
<211> LENGTH: 39
<212> TYPE: DNA
<213> ORGANISM: Artificial Sequence
<220> FEATURE:
<223> OTHER INFORMATION: PRIMER-12

<400> SEQUENCE: 30
tttgcggccg cttattttaa gtattcctta tgtttctcc    39

<210> SEQ ID NO 31
<211> LENGTH: 855
<212> TYPE: DNA
<213> ORGANISM: Hevea brasiliensis

<400> SEQUENCE: 31
atggaattat acaacggtga gaggccaagt gtgttcagac ttttagggaa gtatatgaga     60
aaagggttat atagcatcct aacccagggt cccatcccta ctcatattgc cttcatattg    120
gatggaaacg ggaggtttgc taagaagcat aaactgccag aaggaggtgg tcataaggct    180
ggattttttag ctcttctgaa cgtactaact tattgctatg agttaggagt gaaatatgcg    240
actatctatg cctttagcat cgataatttt cgaaggaaac ctcatgaggt tcagtacgta    300
atgaatctaa tgctggagaa gattgaaggg atgatcatgg aagaaagtat catcaatgca    360
tatgatattt gcgtgcgttt tgttggtaat ctgaagcttt tagatgagcc actcaagacc    420
gcagcagata agataatgag ggctactgcc aaaaattcca aatttgtgct tctccttgct    480
gtatgctaca cttcaactga tgagatcgtg catgctgttg aagaatcctc taaggataaa    540
ttgaaatccg atgaaatttg caacgatgga acggagatt gtgtgattaa aattgaggag    600
atggagccat attctgaaat aaaacttgta gagcttgaga gaaacactta cataaatcct    660
tatcctgatg tcttgattcg aacttctggg gagacccgtc tgagcaacta cctactttgg    720
cagactacta attgcatact gtattctcct catgcactgt ggccagagat tggtcttcga    780
cacgtggtgt gggcagtaat taactgccaa cgtcattatt cttacttgga gaaacataag    840
gaatacttaa aataa                                                     855

<210> SEQ ID NO 32
<211> LENGTH: 284
<212> TYPE: PRT
<213> ORGANISM: Hevea brasiliensis

<400> SEQUENCE: 32

Met Glu Leu Tyr Asn Gly Glu Arg Pro Ser Val Phe Arg Leu Leu Gly
1               5                   10                  15

Lys Tyr Met Arg Lys Gly Leu Tyr Ser Ile Leu Thr Gln Gly Pro Ile
            20                  25                  30

Pro Thr His Ile Ala Phe Ile Leu Asp Gly Asn Gly Arg Phe Ala Lys
        35                  40                  45

```
Lys His Lys Leu Pro Glu Gly Gly His Lys Ala Gly Phe Leu Ala
 50                  55                  60

Leu Leu Asn Val Leu Thr Tyr Cys Tyr Glu Leu Gly Val Lys Tyr Ala
 65                  70                  75                  80

Thr Ile Tyr Ala Phe Ser Ile Asp Asn Phe Arg Arg Lys Pro His Glu
                 85                  90                  95

Val Gln Tyr Val Met Asn Leu Met Leu Glu Lys Ile Glu Gly Met Ile
            100                 105                 110

Met Glu Glu Ser Ile Ile Asn Ala Tyr Asp Ile Cys Val Arg Phe Val
            115                 120                 125

Gly Asn Leu Lys Leu Leu Asp Glu Pro Leu Lys Thr Ala Ala Asp Lys
130                 135                 140

Ile Met Arg Ala Thr Ala Lys Asn Ser Lys Phe Val Leu Leu Leu Ala
145                 150                 155                 160

Val Cys Tyr Thr Ser Thr Asp Glu Ile Val His Ala Val Glu Glu Ser
                165                 170                 175

Ser Lys Asp Lys Leu Lys Ser Asp Glu Ile Cys Asn Asp Gly Asn Gly
            180                 185                 190

Asp Cys Val Ile Lys Ile Glu Glu Met Glu Pro Tyr Ser Glu Ile Lys
            195                 200                 205

Leu Val Glu Leu Glu Arg Asn Thr Tyr Ile Asn Pro Tyr Pro Asp Val
210                 215                 220

Leu Ile Arg Thr Ser Gly Glu Thr Arg Leu Ser Asn Tyr Leu Leu Trp
225                 230                 235                 240

Gln Thr Thr Asn Cys Ile Leu Tyr Ser Pro His Ala Leu Trp Pro Glu
                245                 250                 255

Ile Gly Leu Arg His Val Val Trp Ala Val Ile Asn Cys Gln Arg His
            260                 265                 270

Tyr Ser Tyr Leu Glu Lys His Lys Glu Tyr Leu Lys
            275                 280

<210> SEQ ID NO 33
<211> LENGTH: 23
<212> TYPE: DNA
<213> ORGANISM: Artificial Sequence
<220> FEATURE:
<223> OTHER INFORMATION: PRIMER-13

<400> SEQUENCE: 33
atacccggga tggaaatata tac                                              23

<210> SEQ ID NO 34
<211> LENGTH: 24
<212> TYPE: DNA
<213> ORGANISM: Artificial Sequence
<220> FEATURE:
<223> OTHER INFORMATION: PRIMER-14

<400> SEQUENCE: 34
actcccgggt tattttaaat attc                                             24

<210> SEQ ID NO 35
<211> LENGTH: 891
<212> TYPE: DNA
<213> ORGANISM: Hevea brasiliensis
```

<400> SEQUENCE: 35

```
atggaaatat atacgggtca gaggccaagt gtgtttaaac ttttttgggaa atttatgaga    60
aaagggttat atcgcatcct aacccaaggt cccattccta ctcatcttgc cttcatattg   120
gatggaaacc ggaggtttgc taagaagcat aaaatgaacg aagcagaagg ttataaggca   180
ggatatttag ctcttctgaa aacactaact tattgctatg agttgggagt gaggtacgta   240
accatttatg cctttagcat tgataatttt cgaaggcaac ctcaggaggt tcagtgcgta   300
atgaatctta tgatggagaa gattgaagag attattgtgg aagaaagtat catgaatgca   360
tatgatgttg gcgtacgtat tgtgggtaac ctgaagcttt tagatgagcc aatcaggatc   420
gcagcagaaa aaattatgag ggctactgcc aataattcca ggtttgtgct tctcattgct   480
gtagcctata gttcaactga tgagatcgtg catgctgttg aagaatcctc taaagacaaa   540
ttgaactcca atgaagtttg caacaatggg attgaagctg aacaagaatt taaggaggca   600
aacggaactg gaaacagtgt gattccagtt cagaagacgg agtcatattc tggaataaat   660
cttgcagacc ttgagaaaaa cacctacgta aatcctcatc ctgatgtctt gattcgaact   720
tctgggttga gccgtctaag taactaccta ctttggcaga ctagtaattg catactgtat   780
tctccttttg cactgtggcc agagattggt ctcaggcact ggtatgtgac agtaatgaac   840
ttccaacgtc atcattctta tttggagaag cataaggaat atttaaaata a           891
```

<210> SEQ ID NO 36
<211> LENGTH: 296
<212> TYPE: PRT
<213> ORGANISM: Hevea brasiliensis

<400> SEQUENCE: 36

```
Met Glu Ile Tyr Thr Gly Gln Arg Pro Ser Val Phe Lys Leu Phe Gly
1               5                   10                  15

Lys Phe Met Arg Lys Gly Leu Tyr Arg Ile Leu Thr Gln Gly Pro Ile
            20                  25                  30

Pro Thr His Leu Ala Phe Ile Leu Asp Gly Asn Arg Arg Phe Ala Lys
        35                  40                  45

Lys His Lys Met Asn Glu Ala Glu Gly Tyr Lys Ala Gly Tyr Leu Ala
    50                  55                  60

Leu Leu Lys Thr Leu Thr Tyr Cys Tyr Glu Leu Gly Val Arg Tyr Val
65                  70                  75                  80

Thr Ile Tyr Ala Phe Ser Ile Asp Asn Phe Arg Arg Gln Pro Gln Glu
                85                  90                  95

Val Gln Cys Val Met Asn Leu Met Met Glu Lys Ile Glu Glu Ile Ile
            100                 105                 110

Val Glu Glu Ser Ile Met Asn Ala Tyr Asp Val Gly Val Arg Ile Val
        115                 120                 125

Gly Asn Leu Lys Leu Leu Asp Glu Pro Ile Arg Ile Ala Ala Glu Lys
    130                 135                 140

Ile Met Arg Ala Thr Ala Asn Asn Ser Arg Phe Val Leu Leu Ile Ala
145                 150                 155                 160

Ile Ala Tyr Ser Ser Thr Asp Glu Ile Val His Ala Val Glu Glu Ser
                165                 170                 175

Ser Lys Asp Lys Leu Asn Ser Asn Glu Val Cys Asn Asn Gly Ile Glu
            180                 185                 190

Ala Glu Gln Glu Phe Lys Glu Ala Asn Gly Thr Gly Asn Ser Val Ile
        195                 200                 205
```

Pro Val Gln Lys Thr Glu Ser Tyr Ser Gly Ile Asn Leu Val Asp Leu
    210                 215                 220

Glu Lys Asn Thr Tyr Val Asn Pro Tyr Pro Asp Val Leu Ile Arg Thr
225                 230                 235                 240

Ser Gly Leu Ser Arg Leu Ser Asn Tyr Leu Leu Trp Gln Thr Ser Asn
            245                 250                 255

Cys Ile Leu Tyr Ser Pro Phe Ala Leu Trp Pro Glu Ile Gly Leu Gly
            260                 265                 270

His Leu Val Trp Thr Val Met Asp Phe Gln Arg His His Ser Tyr Leu
            275                 280                 285

Lys Lys His Lys Glu Tyr Leu Lys
            290                 295

<210> SEQ ID NO 37
<211> LENGTH: 373
<212> TYPE: PRT
<213> ORGANISM: Hevea brasiliensis

<400> SEQUENCE: 37

Met Glu Lys His Ser Ser Arg Val Ser Glu Leu Phe Gly Asn Leu
1               5                   10                  15

Gly Ser Phe Ile Arg Ile Cys Ile Phe Arg Val Leu Ser Met Gly Pro
                20                  25                  30

Ile Pro Asn His Phe Ala Phe Ile Met Asp Gly Asn Arg Arg Tyr Ala
                35                  40                  45

Lys Lys Glu Asn Met Lys Lys Gly Ala Gly His Arg Ala Gly Phe Leu
    50                  55                  60

Ala Leu Ile Ser Ile Leu Lys Tyr Cys Tyr Glu Leu Gly Val Lys Tyr
65                  70                  75                  80

Val Thr Ile Tyr Ala Phe Ser Ile His Asn Phe Lys Arg Ser Pro Asp
                85                  90                  95

Glu Val Lys Asp Leu Met Asp Leu Met Leu Glu Lys Ile Glu Asp Leu
                100                 105                 110

Leu Arg Asp Glu Ser Ile Val Asn Gln Tyr Gly Ile Arg Val Tyr Phe
            115                 120                 125

Ile Gly Asn Leu Lys Leu Leu Ser Glu Thr Val Arg Ile Ala Ala Glu
    130                 135                 140

Lys Val Met Lys Ala Thr Ala Lys Asn Thr Asn Cys Thr Leu Leu Ile
145                 150                 155                 160

Cys Val Ala Tyr Thr Ser Arg Asp Glu Ile Val His Ala Val Gln Val
                165                 170                 175

Ser Cys Lys Asn Lys Gln Glu Ile Gln Pro Leu Ser Phe Cys Lys
            180                 185                 190

Ala Asn Asn Asp Ala Ile Glu Val Glu Asp Asn Lys Lys Val Asn
            195                 200                 205

Gly Val Ile Pro Phe Val Phe Leu Glu Ser Gln Lys Asp Glu Ala Gly
    210                 215                 220

Lys Ser Gln Ala Thr Met Ala Ser Val Thr Cys Ser Cys Leu Ala Arg
225                 230                 235                 240

Gly Val Glu Gly Gly Asn Lys Asn Ser Met Val Val Arg Ala Val
            245                 250                 255

Arg Gly Ser Tyr Glu Asp Lys Trp Asp Asn Cys Gln Ala Met Met Glu
            260                 265                 270

Asn Arg Thr Gly Asn Gly Val Thr Ser Ser Glu Glu Ser Glu Asn Leu
            275                 280                 285

```
        Gln Gly Glu Cys Ser Ile Ile Lys Leu Val Asp Ile Glu Lys Gln Met
            290                 295                 300

Tyr Met Ala Val Ala Pro Glu Pro Asp Ile Leu Ile Arg Ser Ser Gly
        305                 310                 315                 320

Glu Ser Arg Leu Ser Asn Phe Leu Leu Trp Gln Thr Ser Glu Cys Gln
                        325                 330                 335

Leu Tyr Ser Pro Asp Ala Leu Trp Pro Glu Ile Gly Leu Trp His Leu
                    340                 345                 350

Val Trp Ala Val Leu Asn Phe Gln Arg Asn His Ala Tyr Leu Glu Lys
                355                 360                 365

Lys Lys His Gln Leu
            370

<210> SEQ ID NO 38
<211> LENGTH: 18
<212> TYPE: DNA
<213> ORGANISM: Artificial Sequence
<220> FEATURE:
<223> OTHER INFORMATION: PRIMER-15

<400> SEQUENCE: 38
tatcccggga tggaaata                                                  18

<210> SEQ ID NO 39
<211> LENGTH: 19
<212> TYPE: DNA
<213> ORGANISM: Artificial Sequence
<220> FEATURE:
<223> OTHER INFORMATION: PRIMER-16

<400> SEQUENCE: 39
atacccgggt tacaactgc                                                 19

<210> SEQ ID NO 40
<211> LENGTH: 1107
<212> TYPE: DNA
<213> ORGANISM: Hevea brasiliensis

<400> SEQUENCE: 40
atggaaatat ttgaggctgg taggccaagc gtgcttgcaa gtttggggag atttatcaga      60
aaatgcatat ttcgcattct atcaataggt cccatcccaa gtcatgttgc cttcataatg     120
gatggaaacc ggaggtttgc taagaaggag aaactggaag aaggatctgg tcacagggct     180
ggatctttag ctctaatgtc cacgcttaag tactgctatg agttgggagt gaagtatgtg     240
actatatatg ccttcagcat tgataatttt agaaggcgac ctgatgaggt tcagctcata     300
atggatctaa tactggagaa gattgagggg ctgctcaggg acgaaaatgt tgtcaatgca     360
tatggcatca gagtacgatt tgtaggtacc ttgaagcttc taagtgagcc agtcagggtc     420
gcagcagaaa aagtcgccag ggctagtgcc aagaatacca agtttgtgct tgtcatttgt     480
atagcctatt cttcaactga tgagattgtg catgctgttc aagaatcttg taaatataaa     540
ttgaacaaaa ttgagccatc taactccaac agggcttgca atgatgcgaa tgaacaagta     600
gaagaaaatg gtaagaagat agatagtacc atcacacatg gtgttcaaga atcctgcaaa     660
gatgaaacag ataaatctcg cacaataaac gcaaagccaa tgtataatgg tgtgaccaaa     720
gaagctggag ggactgacaa tgctaatact gtgatagtaa attccatcgg agacaagtgg     780
gatgatgctc acgaactggg ggcaactaga actggcaatg gtgtgatttc agtagaagaa     840
attgataaga tgctgtcaca ttctagcata aagttggtag acattgagaa aaaattgcac     900
```

-continued

```
atggctgtag cccctgatcc tgatatcttg gttcgaactt ctggagagag ccgtctgagc    960
aacttcctac tttggcagac tagtaactgt tcactgtatt ctccaaaggc actgtggccg   1020
gagattggcc tacgccactt ggtgtgggca gtaataacct tccaacgtaa tcattcttat   1080
ttggagaaga aaagaagca gttgtaa                                        1107
```

<210> SEQ ID NO 41
<211> LENGTH: 368
<212> TYPE: PRT
<213> ORGANISM: Hevea brasiliensis

<400> SEQUENCE: 41

```
Met Glu Ile Phe Glu Ala Gly Arg Pro Ser Val Leu Ala Ser Leu Gly
1               5                   10                  15

Arg Phe Ile Arg Lys Cys Ile Phe Arg Ile Leu Ser Ile Gly Pro Ile
            20                  25                  30

Pro Ser His Val Ala Phe Ile Met Asp Gly Asn Arg Arg Phe Ala Lys
        35                  40                  45

Lys Glu Lys Leu Glu Glu Gly Ser Gly His Arg Ala Gly Ser Leu Ala
    50                  55                  60

Leu Met Ser Thr Leu Lys Tyr Cys Tyr Glu Leu Gly Val Lys Tyr Val
65                  70                  75                  80

Thr Ile Tyr Ala Phe Ser Ile Asp Asn Phe Arg Arg Pro Asp Glu
            85                  90                  95

Val Gln Leu Ile Met Asp Leu Ile Leu Glu Lys Ile Glu Gly Leu Leu
            100                 105                 110

Arg Asp Glu Asn Val Val Asn Ala Tyr Gly Ile Arg Val Arg Phe Val
            115                 120                 125

Gly Thr Leu Lys Leu Leu Ser Glu Pro Val Arg Val Ala Ala Glu Lys
130                 135                 140

Val Ala Arg Ala Ser Ala Lys Asn Thr Lys Phe Val Leu Val Ile Cys
145                 150                 155                 160

Ile Ala Tyr Ser Ser Thr Asp Glu Ile Val His Ala Val Gln Glu Ser
                165                 170                 175

Cys Lys Tyr Lys Leu Asn Lys Ile Glu Pro Ser Asn Ser Asn Arg Ala
            180                 185                 190

Cys Asn Asp Ala Asn Glu Gln Val Glu Glu Asn Gly Lys Lys Ile Asp
        195                 200                 205

Ser Thr Ile Thr His Gly Val Gln Glu Ser Cys Lys Asp Glu Thr Asp
    210                 215                 220

Lys Ser Arg Thr Ile Asn Ala Lys Pro Met Tyr Asn Gly Val Thr Lys
225                 230                 235                 240

Glu Ala Gly Gly Thr Asp Asn Ala Asn Thr Val Ile Val Asn Ser Ile
                245                 250                 255

Gly Asp Lys Trp Asp Asp Ala His Glu Leu Gly Ala Thr Arg Thr Gly
            260                 265                 270

Asn Gly Val Ile Ser Val Glu Glu Ile Asp Lys Met Leu Ser His Ser
        275                 280                 285

Ser Ile Lys Leu Val Asp Ile Glu Lys Lys Leu His Met Ala Val Ala
    290                 295                 300

Pro Asp Pro Asp Ile Leu Val Arg Thr Ser Gly Glu Ser Arg Leu Ser
305                 310                 315                 320

Asn Phe Leu Leu Trp Gln Thr Ser Asn Cys Ser Leu Tyr Ser Pro Lys
                325                 330                 335
```

```
Ala Leu Trp Pro Glu Ile Gly Leu Arg His Leu Val Trp Ala Val Ile
            340                 345                 350

Thr Phe Gln Arg Asn His Ser Tyr Leu Glu Lys Lys Lys Gln Leu
        355                 360                 365

<210> SEQ ID NO 42
<211> LENGTH: 927
<212> TYPE: DNA
<213> ORGANISM: Taraxacum brevicorniculatum

<400> SEQUENCE: 42
atgcaagtga atccaatcat tactacagat agttcactga aactagtgga agaagaaaga      60
tcaaatggta ggatcggcaa tttcttagga ggcttaaacg ccaccttaag aaaactcgtg     120
tttcgtgtca ttgcttctcg ccctatccca gaacacatcg ccttcatcct cgatggaaac     180
cgaaggttcg ccaggaaatg gaacctcaca gaaggcacag gccacaaaac cggcttccta     240
gcactcatgt cggtcctcaa atactgctac gagatcggag tcaagtacgt caccatctac     300
gccttcagcc tcgacaattt caatcgacgc cctgatgaag tccaatacgt catggatttg     360
atgcaagaca agatcgaagg cttttctgaaa gaagttagta ttataaacca atatggcgtt     420
agagtcttgt tcatcggtga tctcgatagg ttatatgagc ccgtaaggat tgctgctgag     480
aaggccatgg aagccaccgc taaaaattca accacgtatc tcctcgtatg tgttgcttac     540
acttcttccc atgaaatccc acgtgccatc cacgaagctt gtgaagaaaa gagtggcgcc     600
atggccaata gcatacgggt catgaacgga aacgggtttt tcaatggaaa tggatatacc     660
aacgtgaatc atggaagtca ggcggtgatc aaagtggtgg atcttgataa gcatatgtac     720
atgggggtgg caccggatcc tgatatttta gtacggagct ccggcgagac aaggctgagc     780
aactttctgc tgtggcaaac caccaactgt tgttgtatt ccccgaaagc tttgtggccg     840
gagatggggt tctggcaggt ggtttgggga atcttggagt ttcagaacaa ttataattac     900
ttggagaaga agaagaagca ggcataa                                          927

<210> SEQ ID NO 43
<211> LENGTH: 308
<212> TYPE: PRT
<213> ORGANISM: Taraxacum brevicorniculatum

<400> SEQUENCE: 43

Met Gln Val Asn Pro Ile Ile Thr Thr Asp Ser Ser Leu Lys Leu Val
1               5                   10                  15

Glu Glu Glu Arg Ser Asn Gly Arg Ile Gly Asn Phe Leu Gly Gly Leu
            20                  25                  30

Asn Ala Thr Leu Arg Lys Leu Val Phe Arg Val Ile Ala Ser Arg Pro
        35                  40                  45

Ile Pro Glu His Ile Ala Phe Ile Leu Asp Gly Asn Arg Arg Phe Ala
    50                  55                  60

Arg Lys Trp Asn Leu Thr Glu Gly Thr Gly His Lys Thr Gly Phe Leu
65                  70                  75                  80

Ala Leu Met Ser Val Leu Lys Tyr Cys Tyr Glu Ile Gly Val Lys Tyr
                85                  90                  95

Val Thr Ile Tyr Ala Phe Ser Leu Asp Asn Phe Asn Arg Arg Pro Asp
            100                 105                 110

Glu Val Gln Tyr Val Met Asp Leu Met Gln Asp Lys Ile Glu Gly Phe
        115                 120                 125
```

```
Leu Lys Glu Val Ser Ile Ile Asn Gln Tyr Gly Val Arg Val Leu Phe
130                 135                 140

Ile Gly Asp Leu Asp Arg Leu Tyr Glu Pro Val Arg Ile Ala Ala Glu
145                 150                 155                 160

Lys Ala Met Glu Ala Thr Ala Lys Asn Ser Thr Thr Tyr Leu Leu Val
                165                 170                 175

Cys Val Ala Tyr Thr Ser Ser His Glu Ile Pro Arg Ala Ile His Glu
                180                 185                 190

Ala Cys Glu Glu Lys Ser Gly Ala Met Ala Asn Ser Ile Arg Val Met
                195                 200                 205

Asn Gly Asn Gly Phe Phe Asn Gly Asn Gly Tyr Thr Asn Val Asn His
210                 215                 220

Gly Ser Gln Ala Val Ile Lys Val Val Asp Leu Asp Lys His Met Tyr
225                 230                 235                 240

Met Gly Val Ala Pro Asp Pro Asp Ile Leu Val Arg Ser Ser Gly Glu
                245                 250                 255

Thr Arg Leu Ser Asn Phe Leu Leu Trp Gln Thr Thr Asn Cys Leu Leu
                260                 265                 270

Tyr Ser Pro Lys Ala Leu Trp Pro Glu Met Gly Phe Trp Gln Val Val
                275                 280                 285

Trp Gly Ile Leu Glu Phe Gln Asn Asn Tyr Asn Tyr Leu Glu Lys Lys
290                 295                 300

Lys Lys Gln Ala
305

<210> SEQ ID NO 44
<211> LENGTH: 302
<212> TYPE: PRT
<213> ORGANISM: Arabidopsis thaliana

<400> SEQUENCE: 44

Met Leu Ser Ile Leu Ser Ser Leu Leu Ser Leu Leu Phe Leu Phe Ile
1               5                   10                  15

Ile Ser Cys Phe Phe Ile Thr Ser His Phe Trp Phe Pro Leu Ser Leu
                20                  25                  30

Pro Lys Ile Leu Gly Phe Ile Lys Ile Thr Ser Ser Arg Asp Asp Tyr
                35                  40                  45

Asp Asn Glu Gln Arg Asp Glu Gly Thr Tyr Val Val Gly Val Glu Glu
50                  55                  60

Leu Gln Arg Glu Leu Met Pro Arg His Val Ala Val Ile Met Asp Gly
65                  70                  75                  80

Asn Arg Arg Trp Ala Lys Arg Ala Gly Leu Leu Thr Ser Gln Gly His
                85                  90                  95

Glu Ala Gly Ala Lys Arg Leu Ile Glu Phe Ser Glu Leu Cys Phe Lys
                100                 105                 110

Leu Gly Ile His Thr Val Ser Ala Phe Ala Phe Ser Thr Glu Asn Trp
                115                 120                 125

Gly Arg His Lys Ile Glu Val Lys Cys Leu Met Ser Leu Ile Gln His
                130                 135                 140

Tyr Leu Lys Ser Lys Ile Gln Tyr Phe Gln Arg Glu Glu Thr Arg Val
145                 150                 155                 160

Ser Val Ile Gly Asn Leu Thr Lys Ile Pro Glu Ser Leu Leu Arg Thr
                165                 170                 175

Val Gln Glu Ile Glu Glu Ala Thr Arg Ser Tyr Lys Lys Lys His Leu
                180                 185                 190
```

```
Ile Leu Ala Ile Asp Tyr Ser Gly Arg Leu Asp Ile Leu Arg Ala Cys
            195                 200                 205

Lys Ser Ile Val Lys Ser Glu Lys Gly Leu Ile Arg Glu Glu Asp
210                 215                 220

Val Asp Glu Ala Leu Ile Glu Arg Glu Leu Leu Thr Asn Cys Thr Glu
225                 230                 235                 240

Phe Pro Ser Pro Asp Leu Leu Ile Arg Thr Ser Gly Glu Gln Arg Ile
                245                 250                 255

Ser Asn Phe Phe Leu Trp Gln Leu Ala Tyr Thr Glu Leu Phe Phe Ser
                260                 265                 270

Pro Val Leu Trp Pro Asp Phe Asp Lys Asp Lys Leu Leu Glu Ala Leu
                275                 280                 285

Val Ser Tyr Gln Arg Arg Glu Arg Arg Phe Gly Cys Arg Val
                290                 295                 300

<210> SEQ ID NO 45
<211> LENGTH: 252
<212> TYPE: PRT
<213> ORGANISM: Escherichia coli

<400> SEQUENCE: 45

Met Leu Ser Ala Thr Gln Pro Leu Ser Glu Lys Leu Pro Ala His Gly
1               5                   10                  15

Cys Arg His Val Ala Ile Ile Met Asp Gly Asn Gly Arg Trp Ala Lys
                20                  25                  30

Lys Gln Gly Lys Ile Arg Ala Phe Gly His Lys Ala Gly Ala Lys Ser
            35                  40                  45

Val Arg Arg Ala Val Ser Phe Ala Ala Asn Asn Gly Ile Glu Ala Leu
50                  55                  60

Thr Leu Tyr Ala Phe Ser Ser Glu Asn Trp Asn Arg Pro Ala Gln Glu
65                  70                  75                  80

Val Ser Ala Leu Met Glu Leu Phe Val Trp Ala Leu Asp Ser Glu Val
                85                  90                  95

Lys Ser Leu His Arg His Asn Val Arg Leu Arg Ile Ile Gly Asp Thr
            100                 105                 110

Ser Arg Phe Asn Ser Arg Leu Gln Glu Arg Ile Arg Lys Ser Glu Ala
        115                 120                 125

Leu Thr Ala Gly Asn Ser Gly Leu Thr Leu Asn Ile Ala Ala Asn Tyr
    130                 135                 140

Gly Gly Arg Trp Asp Ile Val Gln Gly Val Arg Gln Leu Ala Glu Lys
145                 150                 155                 160

Val Gln Gln Gly Asn Leu Gln Pro Asp Gln Ile Asp Glu Glu Met Leu
                165                 170                 175

Asn Gln His Val Cys Met His Glu Leu Ala Pro Val Asp Leu Val Ile
            180                 185                 190

Arg Thr Gly Gly Glu His Arg Ile Ser Asn Phe Leu Leu Trp Gln Ile
        195                 200                 205

Ala Tyr Ala Glu Leu Tyr Phe Thr Asp Val Leu Trp Pro Asp Phe Asp
    210                 215                 220

Glu Gln Asp Phe Lys Gly Ala Leu Asn Ala Phe Ala Asn Arg Glu Arg
225                 230                 235                 240

Arg Phe Gly Gly Thr Glu Pro Gly Asp Glu Thr Ala
                245                 250
```

<210> SEQ ID NO 46
<211> LENGTH: 249
<212> TYPE: PRT
<213> ORGANISM: Micrococcus luteus

<400> SEQUENCE: 46

Met Phe Pro Ile Lys Lys Arg Lys Ala Ile Lys Asn Asn Asn Ile Asn
1               5                   10                  15

Ala Ala Gln Ile Pro Lys His Ile Ala Ile Met Asp Gly Asn Gly
            20                  25                  30

Arg Trp Ala Lys Gln Lys Lys Met Pro Arg Ile Lys Gly His Tyr Glu
        35                  40                  45

Gly Met Gln Thr Val Lys Lys Ile Thr Arg Tyr Ala Ser Asp Leu Gly
    50                  55                  60

Val Lys Tyr Leu Thr Leu Tyr Ala Phe Ser Thr Glu Asn Trp Ser Arg
65                  70                  75                  80

Pro Lys Asp Glu Val Asn Tyr Leu Met Lys Leu Pro Gly Asp Phe Leu
                85                  90                  95

Asn Thr Phe Leu Pro Glu Leu Ile Glu Lys Asn Val Lys Val Glu Thr
            100                 105                 110

Ile Gly Phe Ile Asp Asp Leu Pro Asp His Thr Lys Lys Ala Val Leu
        115                 120                 125

Glu Ala Lys Glu Lys Thr Lys His Asn Thr Gly Leu Thr Leu Val Phe
    130                 135                 140

Ala Leu Asn Tyr Gly Gly Arg Lys Glu Ile Ile Ser Ala Val Gln Leu
145                 150                 155                 160

Ile Ala Glu Arg Tyr Lys Ser Gly Glu Ile Ser Leu Asp Glu Ile Ser
                165                 170                 175

Glu Thr His Phe Asn Glu Tyr Leu Phe Thr Ala Asn Met Pro Asp Pro
            180                 185                 190

Glu Leu Leu Ile Arg Thr Ser Gly Glu Glu Arg Leu Ser Asn Phe Leu
        195                 200                 205

Ile Trp Gln Cys Ser Tyr Ser Glu Phe Val Phe Ile Asp Glu Phe Trp
    210                 215                 220

Pro Asp Phe Asn Glu Glu Ser Leu Ala Gln Cys Ile Ser Ile Tyr Gln
225                 230                 235                 240

Asn Arg His Arg Arg Phe Gly Gly Leu
                245

<210> SEQ ID NO 47
<211> LENGTH: 343
<212> TYPE: PRT
<213> ORGANISM: Saccharomyces cerevisiae

<400> SEQUENCE: 47

Met Lys Met Pro Ser Ile Ile Gln Ile Gln Phe Val Ala Leu Lys Arg
1               5                   10                  15

Leu Leu Val Glu Thr Lys Glu Gln Met Cys Phe Ala Val Lys Ser Ile
            20                  25                  30

Phe Gln Arg Val Phe Ala Trp Val Met Ser Leu Ser Leu Phe Ser Trp
        35                  40                  45

Phe Tyr Val Asn Leu Gln Asn Ile Leu Ile Lys Ala Leu Arg Val Gly
    50                  55                  60

Pro Val Pro Glu His Val Ser Phe Ile Met Asp Gly Asn Arg Arg Tyr
65                  70                  75                  80

```
Ala Lys Ser Arg Arg Leu Pro Val Lys Lys Gly His Glu Ala Gly Gly
                 85                  90                  95

Leu Thr Leu Leu Thr Leu Leu Tyr Ile Cys Lys Arg Leu Gly Val Lys
            100                 105                 110

Cys Val Ser Ala Tyr Ala Phe Ser Ile Glu Asn Phe Asn Arg Pro Lys
            115                 120                 125

Glu Glu Val Asp Thr Leu Met Asn Leu Phe Thr Val Lys Leu Asp Glu
            130                 135                 140

Phe Ala Lys Arg Ala Lys Asp Tyr Lys Asp Pro Leu Tyr Gly Ser Lys
145                 150                 155                 160

Ile Arg Ile Val Gly Asp Gln Ser Leu Leu Ser Pro Glu Met Arg Lys
                165                 170                 175

Lys Ile Lys Lys Val Glu Glu Ile Thr Gln Asp Gly Asp Asp Phe Thr
            180                 185                 190

Leu Phe Ile Cys Phe Pro Tyr Thr Ser Arg Asn Asp Met Leu His Thr
            195                 200                 205

Ile Arg Asp Ser Val Glu Asp His Leu Glu Asn Lys Ser Pro Arg Ile
            210                 215                 220

Asn Ile Arg Lys Phe Thr Asn Lys Met Tyr Met Gly Phe His Ser Asn
225                 230                 235                 240

Lys Cys Glu Leu Leu Ile Arg Thr Ser Gly His Arg Arg Leu Ser Asp
                245                 250                 255

Tyr Met Leu Trp Gln Val His Glu Asn Ala Thr Ile Glu Phe Ser Asp
            260                 265                 270

Thr Leu Trp Pro Asn Phe Ser Phe Phe Ala Met Tyr Leu Met Ile Leu
            275                 280                 285

Lys Trp Ser Phe Phe Ser Thr Ile Gln Lys Tyr Asn Glu Lys Asn His
            290                 295                 300

Ser Leu Phe Glu Lys Ile His Glu Ser Val Pro Ser Ile Phe Lys Lys
305                 310                 315                 320

Lys Lys Thr Ala Met Ser Leu Tyr Asn Phe Pro Asn Pro Pro Ile Ser
                325                 330                 335

Val Ser Val Thr Gly Asp Glu
            340

<210> SEQ ID NO 48
<211> LENGTH: 286
<212> TYPE: PRT
<213> ORGANISM: Nicotiana sylvestris

<400> SEQUENCE: 48

Met Leu Lys Ser Met Asp Gly Leu Ala Glu Lys Leu Phe Trp Ser Ser
1                5                  10                  15

Leu Leu Tyr Met Leu Lys Pro Leu Phe Arg Ile Leu Ser Val Gly Pro
            20                  25                  30

Ile Pro Asn His Val Ala Phe Ile Leu Asp Gly Asn Arg Arg Tyr Ala
            35                  40                  45

Lys Lys Arg Asn Met Ala Val Ser Asn Gly Tyr Arg Ala Gly Phe Met
            50                  55                  60

Ala Ile Met Ser Met Leu Lys Tyr Cys Tyr Val Leu Gly Val Lys Tyr
65                  70                  75                  80

Met Thr Ile Tyr Ala Phe Ser Ile Asp Asn Phe Lys Arg Arg Pro Glu
                85                  90                  95

Glu Val Gln Tyr Leu Met Asp Leu Met Leu Glu Lys Ile Glu Gly Leu
            100                 105                 110
```

```
Leu His Lys Glu Ser Val Val Asn Gln Tyr Gly Val Arg Val His Phe
            115                 120                 125

Val Gly Asn Leu Lys Leu Leu Ser Glu Pro Val Arg Val Ala Ala Glu
    130                 135                 140

Lys Ala Met Gln Ala Thr Ala Asn Asn Thr Asn Ser Thr Leu Leu Ile
145                 150                 155                 160

Cys Val Ala Tyr Ser Ser Thr Asp Glu Ile Val His Ala Val Gln Ser
                165                 170                 175

Ser Cys Gln Glu Lys Trp Asn Glu Ile Gln Glu Leu Asn Ala Asn Gln
            180                 185                 190

Pro Gln Asn Val Glu Val Thr Lys Glu Ile Gln Glu Leu Asn Gln Ile
        195                 200                 205

Ile Gln Leu Val Asp Ile Glu Arg His Met Tyr Met Arg Leu Ala His
    210                 215                 220

Asn Pro Asp Met Leu Ile Arg Thr Ser Gly Glu Thr Arg Leu Ser Asn
225                 230                 235                 240

Phe Leu Leu Trp Gln Thr Thr Asn Cys Leu Tyr Ser Pro Lys Val
                245                 250                 255

Leu Phe Pro Glu Ile Gly Leu Arg His Leu Ile Trp Ala Val Leu His
            260                 265                 270

Phe Gln Arg Leu Tyr Pro His Leu Glu Lys Arg Lys Gln Leu
        275                 280                 285

<210> SEQ ID NO 49
<211> LENGTH: 333
<212> TYPE: PRT
<213> ORGANISM: Mus musculus

<400> SEQUENCE: 49

Met Ser Trp Ile Lys Glu Gly Glu Leu Ser Leu Trp Glu Arg Phe Cys
1               5                   10                  15

Ala Asn Ile Ile Lys Ala Gly Pro Val Pro Lys His Ile Ala Phe Ile
            20                  25                  30

Met Asp Gly Asn Arg Arg Tyr Ala Lys Lys Cys Gln Val Glu Arg Gln
        35                  40                  45

Glu Gly His Thr Gln Gly Phe Asn Lys Leu Ala Glu Thr Leu Arg Trp
    50                  55                  60

Cys Leu Asn Leu Gly Ile Leu Glu Val Thr Val Tyr Ala Phe Ser Ile
65                  70                  75                  80

Glu Asn Phe Lys Arg Ser Lys Ser Glu Val Asp Gly Leu Leu Asp Leu
                85                  90                  95

Ala Arg Gln Lys Phe Ser Cys Leu Met Glu Glu Gln Glu Lys Leu Gln
            100                 105                 110

Lys His Gly Val Cys Ile Arg Val Leu Gly Asp Leu His Leu Leu Pro
        115                 120                 125

Leu Asp Leu Gln Glu Lys Ile Ala His Ala Ile Gln Ala Thr Lys Asn
    130                 135                 140

Tyr Asn Lys Cys Phe Leu Asn Val Cys Phe Ala Tyr Thr Ser Arg His
145                 150                 155                 160

Glu Ile Ala Asn Ala Val Arg Glu Met Ala Trp Gly Val Glu Gln Gly
                165                 170                 175

Leu Leu Glu Pro Ser Asp Val Ser Glu Ser Leu Leu Asp Lys Cys Leu
            180                 185                 190

Tyr Ser Asn His Ser Pro His Pro Asp Ile Leu Ile Arg Thr Ser Gly
        195                 200                 205
```

```
Glu Val Arg Leu Ser Asp Phe Leu Leu Trp Gln Thr Ser His Ser Cys
210                 215                 220

Leu Val Phe Gln Pro Val Leu Trp Pro Glu Tyr Thr Phe Trp Asn Leu
225                 230                 235                 240

Cys Glu Ala Ile Leu Gln Phe Gln Arg Asn His Gly Ala Leu Gln Lys
                245                 250                 255

Ala Arg Asp Met Tyr Ala Glu Arg Lys Arg Gln Leu Glu Arg
            260                 265                 270

Asp Gln Ala Ala Val Thr Glu Leu Leu Arg Glu Gly Leu Gln Ala
            275                 280                 285

Ser Gly Asp Ala Gln Leu Arg Arg Thr Arg Leu His Lys Leu Ser Thr
290                 295                 300

Lys Arg Glu Glu Arg Val Gln Gly Phe Leu Lys Ala Leu Glu Leu Lys
305                 310                 315                 320

Arg Ala Asn Trp Leu Ala Leu Trp Gly Thr Ala Ser Ala
                325                 330

<210> SEQ ID NO 50
<211> LENGTH: 333
<212> TYPE: PRT
<213> ORGANISM: Homo sapiens

<400> SEQUENCE: 50

Met Ser Trp Ile Lys Glu Gly Glu Leu Ser Leu Trp Glu Arg Phe Cys
1               5                   10                  15

Ala Asn Ile Ile Lys Ala Gly Pro Met Pro Lys His Ile Ala Phe Ile
                20                  25                  30

Met Asp Gly Asn Arg Arg Tyr Ala Lys Lys Cys Gln Val Glu Arg Gln
            35                  40                  45

Glu Gly His Ser Gln Gly Phe Asn Lys Leu Ala Glu Thr Leu Arg Trp
        50                  55                  60

Cys Leu Asn Leu Gly Ile Leu Glu Val Thr Val Tyr Ala Phe Ser Ile
65                  70                  75                  80

Glu Asn Phe Lys Arg Ser Lys Ser Glu Val Asp Gly Leu Met Asp Leu
                85                  90                  95

Ala Arg Gln Lys Phe Ser Arg Leu Met Glu Glu Lys Glu Lys Leu Gln
            100                 105                 110

Lys His Gly Val Cys Ile Arg Val Leu Gly Asp Leu His Leu Leu Pro
        115                 120                 125

Leu Asp Leu Gln Glu Leu Ile Ala Gln Ala Val Gln Ala Thr Lys Asn
130                 135                 140

Tyr Asn Lys Cys Phe Leu Asn Val Cys Phe Ala Tyr Thr Ser Arg His
145                 150                 155                 160

Glu Ile Ser Asn Ala Val Arg Glu Met Ala Trp Gly Val Glu Gln Gly
                165                 170                 175

Leu Leu Asp Pro Ser Asp Ile Ser Glu Ser Leu Leu Asp Lys Cys Leu
            180                 185                 190

Tyr Thr Asn Arg Ser Pro His Pro Asp Ile Leu Ile Arg Thr Ser Gly
        195                 200                 205

Glu Val Arg Leu Ser Asp Phe Leu Leu Trp Gln Thr Ser His Ser Cys
210                 215                 220

Leu Val Phe Gln Pro Val Leu Trp Pro Glu Tyr Thr Phe Trp Asn Leu
225                 230                 235                 240
```

```
Phe Glu Ala Ile Leu Gln Phe Gln Met Asn His Ser Val Leu Gln Lys
                245                 250                 255
Ala Arg Asp Met Tyr Ala Glu Glu Arg Lys Arg Gln Gln Leu Glu Arg
            260                 265                 270
Asp Gln Ala Thr Val Thr Glu Gln Leu Leu Arg Glu Gly Leu Gln Ala
        275                 280                 285
Ser Gly Asp Ala Gln Leu Arg Arg Thr Arg Leu His Lys Leu Ser Ala
    290                 295                 300
Arg Arg Glu Glu Arg Val Gln Gly Phe Leu Gln Ala Leu Glu Leu Lys
305                 310                 315                 320
Arg Ala Asp Trp Leu Ala Arg Leu Gly Thr Ala Ser Ala
                325                 330

<210> SEQ ID NO 51
<211> LENGTH: 9
<212> TYPE: PRT
<213> ORGANISM: Hevea brasiliensis

<400> SEQUENCE: 51

Asp Gly Asn Arg Arg Phe Ala Lys Lys
1               5

<210> SEQ ID NO 52
<211> LENGTH: 17
<212> TYPE: PRT
<213> ORGANISM: Hevea brasiliensis

<400> SEQUENCE: 52

Thr Ile Tyr Ala Phe Ser Ile Asp Asn Phe Arg Arg Lys Pro His Glu
1               5                   10                  15

Val

<210> SEQ ID NO 53
<211> LENGTH: 26
<212> TYPE: DNA
<213> ORGANISM: Artificial Sequence
<220> FEATURE:
<223> OTHER INFORMATION: PRIMER-17

<400> SEQUENCE: 53
ttaggatcca tggaattata caacgg                                    26

<210> SEQ ID NO 54
<211> LENGTH: 27
<212> TYPE: DNA
<213> ORGANISM: Artificial Sequence
<220> FEATURE:
<223> OTHER INFORMATION: PRIMER-18

<400> SEQUENCE: 54
aacggatcct tttaagtatt ccttatg                                   27

<210> SEQ ID NO 55
<211> LENGTH: 31
<212> TYPE: DNA
<213> ORGANISM: Artificial Sequence
<220> FEATURE:
<223> OTHER INFORMATION: PRIMER-19

<400> SEQUENCE: 55
tttctcgaga tggatttgaa acctggagct g                              31
```

<210> SEQ ID NO 56
<211> LENGTH: 33
<212> TYPE: DNA
<213> ORGANISM: Artificial Sequence
<220> FEATURE:
<223> OTHER INFORMATION: PRIMER-20

<400> SEQUENCE: 56
tttctcgagt catgtaccat aattttgctg cac                          33

<210> SEQ ID NO 57
<211> LENGTH: 24
<212> TYPE: DNA
<213> ORGANISM: Artificial Sequence
<220> FEATURE:
<223> OTHER INFORMATION: PRIMER-21

<400> SEQUENCE: 57
gtcgacatgg attcgaatca atcg                                    24

<210> SEQ ID NO 58
<211> LENGTH: 25
<212> TYPE: DNA
<213> ORGANISM: Artificial Sequence
<220> FEATURE:
<223> OTHER INFORMATION: PRIMER-22

<400> SEQUENCE: 58
ggatccttaa gttccatagt tttgg                                   25

<210> SEQ ID NO 59
<211> LENGTH: 18
<212> TYPE: DNA
<213> ORGANISM: Artificial Sequence
<220> FEATURE:
<223> OTHER INFORMATION: PRIMER-23

<400> SEQUENCE: 59
tatcccggga tgaatacc                                           18

<210> SEQ ID NO 60
<211> LENGTH: 25
<212> TYPE: DNA
<213> ORGANISM: Artificial Sequence
<220> FEATURE:
<223> OTHER INFORMATION: PRIMER-24

<400> SEQUENCE: 60
tgaactagtc taatcgagct ttttc                                   25

<210> SEQ ID NO 61
<211> LENGTH: 16
<212> TYPE: DNA
<213> ORGANISM: Artificial Sequence
<220> FEATURE:
<223> OTHER INFORMATION: PRIMER-25

<400> SEQUENCE: 61
acccgggatg gattcg                                             16

<210> SEQ ID NO 62
<211> LENGTH: 24
<212> TYPE: DNA
<213> ORGANISM: Artificial Sequence
<220> FEATURE:
<223> OTHER INFORMATION: PRIMER-26

<400> SEQUENCE: 62
cgcggactag tttaagttcc atag                                              24

<210> SEQ ID NO 63
<211> LENGTH: 1032
<212> TYPE: DNA
<213> ORGANISM: Saccharomyces cerevisiae

<400> SEQUENCE: 63
atgaaaatgc ccagtattat tcagattcag tttgtagccc taaaaaggct tttggtagaa       60
accaaagaac agatgtgctt cgcagtgaaa agtatatttc agagagtatt tgcgtgggtt      120
atgtcattaa gcttgttttc atggttttat gtaaatcttc agaatatttt gataaaagca      180
ttaagggtag ggccagtgcc tgaacatgtc tcctttatca tggatggtaa ccggagatat      240
gccaagtcaa gaaggctacc agtaaaaaaa ggccatgaag ctggtgggtt aacgttacta      300
acactactgt atatctgcaa agattgggt gtaaatgtg tttccgccta tgcatttct        360 attgaaaatt ttaatagacc aaaagaagaa gtagatacgc taatgaattt gtttacggta      420
aagcttgatg aattcgcaaa agagccaag gactataagg atcccttata cggatctaaa       480
ataagaatag taggtgatca atctttacta tctccagaaa tgagaaaaaa aattaaaaaa      540
gtggaagaaa tcacacagga tggagacgat ttcacttat ttatatgttt tccttacact       600
tcaagaaatg atatgttaca tactattcgt gattcagttg aagaccattt ggaaaataaa      660
tcaccaagga ttaatataag aaaatttact aataaaatgt acatgggttt ccattccaat      720
aaatgtgaat tattaatcag aacaagtggg cataggaggc tctcagacta tatgctatgg      780
caagtacatg aaaatgccac cattgaattt agtgatacgt tgtggccaaa ttttagcttc      840
tttgctatgt acctgatgat tctcaaatgg tccttctttt ccaccattca aaatataat      900 gagaagaatc actcattgtt tgaaaaaata catgaaagcg ttccttcaat atttaaaaaa      960
aagaaaacag ctatgtcttt gtacaacttt ccaaaccccc ccatttcagt ttcggttaca     1020
ggagatgaat aa                                                         1032

<210> SEQ ID NO 64
<211> LENGTH: 1037
<212> TYPE: DNA
<213> ORGANISM: Homo sapiens

<400> SEQUENCE: 64 ggaaagatc tatgtcatgg atcaaggaag gagagctgtc actttgggag cggttctgtg        60
ccaacatcat aaaggcaggc ccaatgccga acacattgc attcataatg gacgggaacc       120
gtcgctatgc caagaagtgc caggtggagc ggcaggaagg ccactcacag gcttcaaca       180 agctagctga gactctgcgg tggtgtttga acctgggcat cctagaggtg acagtctacg      240
cattcagcat tgagaacttc aaacgctcca gagtgaggt agacgggctt atggatctgg       300
cccggcagaa gttcagccgc ttgatggaag aaaaggagaa actgcagaag catggggtgt      360
gtatccgggt cctgggcgat ctgcacttgt tgcccttgga tctccaggag ctgattgcac      420
aagctgtaca ggccacgaag aactacaaca gtgtttcct gaatgtctgt tttgcataca      480
catcccgtca tgagatcagc aatgctgtga gagagatggc ctgggggtg gagcaaggcc      540 tgttggatcc cagtgatatc tctgagtctc tgcttgataa gtgcctctat accaaccgct      600
ctcctcatcc tgcatcttg atacggactt ctggagaagt gcggctgagt gacttcttgc       660
tatggcagac ctctcactcc tgcctggtgt tccaacccgt tctgtggcca gagtatacat      720

-continued

```
tttggaacct cttcgaggcc atcctgcagt tccagatgaa ccatagcgtg cttcagaagg    780
cccgagacat gtatgcagag gagcggaaga ggcagcagct ggagagggac caggctacag    840
tgacagagca gctgctgcga gaggggctcc aagccagtgg ggacgcccag ctccgaagga    900
cacgcttgca caaactctcg gccagacggg aagagcgagt ccaaggcttc ctgcaggcct    960
tggaactcaa gcgagctgac tggctggccc gtctgggcac tgcatcagcc tgaatgaggc   1020
tgtcgacctg ccacttt                                                  1037
```